(12) United States Patent
Kirn et al.

(10) Patent No.: US 11,524,081 B2
(45) Date of Patent: *Dec. 13, 2022

(54) CODON OPTIMIZED REP1 GENES AND USES THEREOF

(71) Applicant: 4D MOLECULAR THERAPEUTICS INC., Emeryville, CA (US)

(72) Inventors: David H. Kirn, Emeryville, CA (US); Melissa A. Kotterman, Emeryville, CA (US); Peter Francis, Emeryville, CA (US)

(73) Assignee: 4D Molecular Therapeutics Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/740,045

(22) Filed: May 9, 2022

(65) Prior Publication Data

US 2022/0265860 A1 Aug. 25, 2022

Related U.S. Application Data

(63) Continuation of application No. 17/463,262, filed on Aug. 31, 2021, now Pat. No. 11,357,870.

(60) Provisional application No. 63/073,837, filed on Sep. 2, 2020.

(51) Int. Cl.
*A61K 48/00* (2006.01)
*C12N 9/10* (2006.01)
*C12N 15/86* (2006.01)
*A61P 27/02* (2006.01)

(52) U.S. Cl.
CPC .......... *A61K 48/0058* (2013.01); *A61P 27/02* (2018.01); *C12N 9/1085* (2013.01); *C12N 15/86* (2013.01); *C12Y 205/01059* (2013.01); *C12N 2750/14143* (2013.01)

(58) Field of Classification Search
None
See application file for complete search history.

*Primary Examiner* — Christopher M Babic
*Assistant Examiner* — Kimberly A Aron
(74) *Attorney, Agent, or Firm* — Christopher M. Cabral; Much Shelist, PC

(57) ABSTRACT

The present disclosure provides codon optimized nucleotide sequences encoding human REP1, vectors, and host cells comprising codon optimized REP1 sequences, and methods of treating retinal disorders such as choroideremia comprising administering to the subject a codon optimized sequence encoding human REP1.

20 Claims, 22 Drawing Sheets

Specification includes a Sequence Listing.

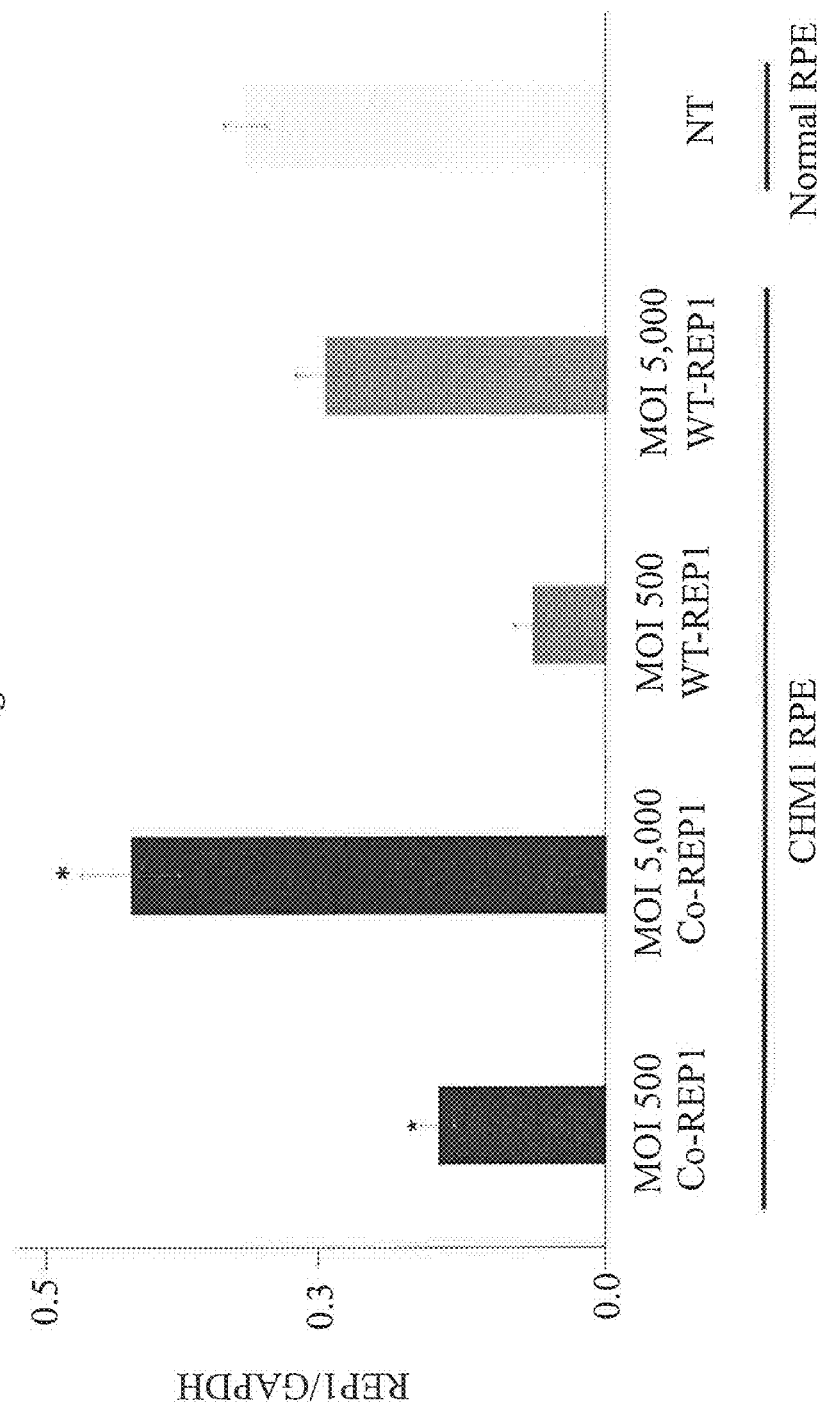

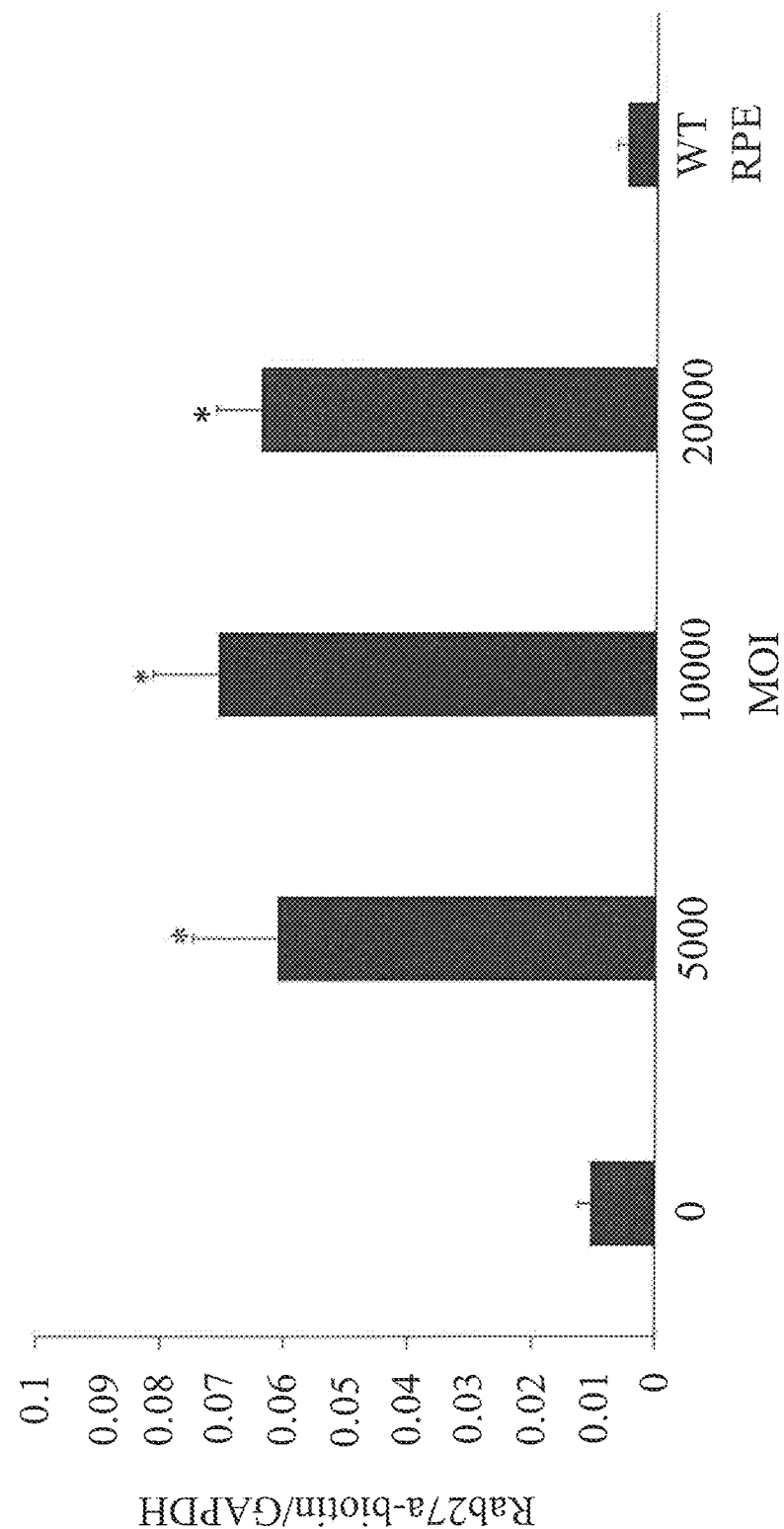

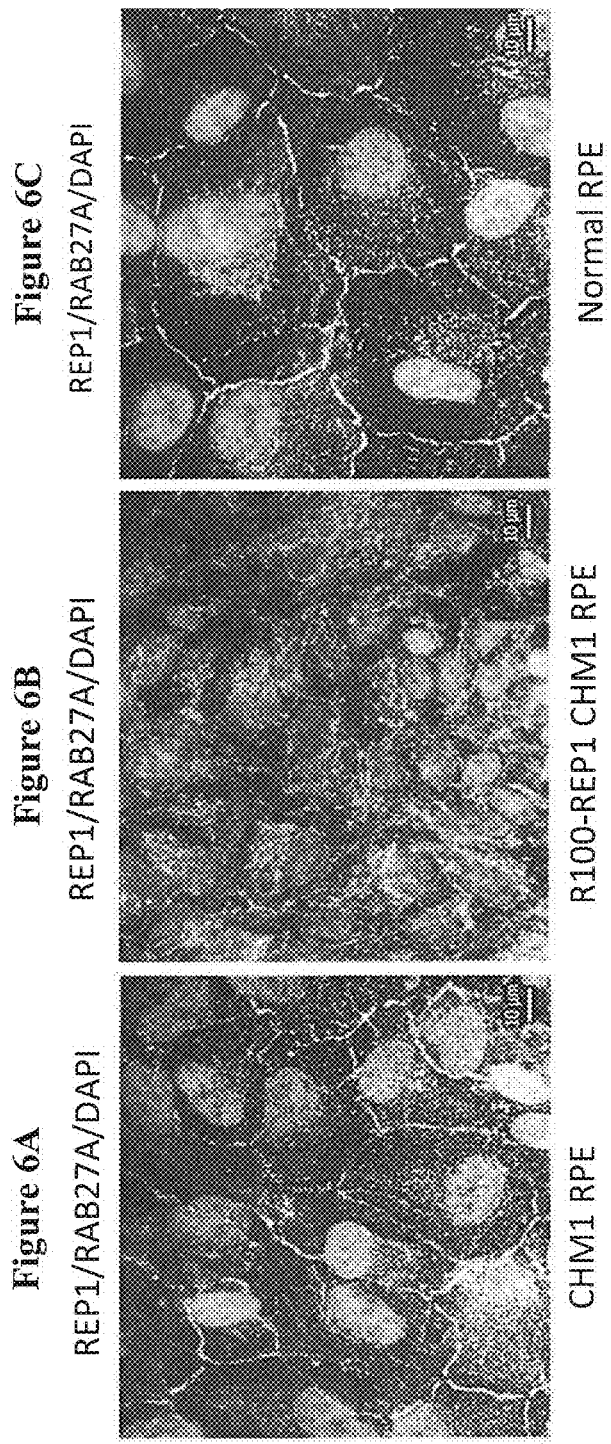

Figure 7

```
Optimized 1863 ATGGTGATACACTGCTTCGAGTTTGATGGATCGTGATTGGAACTGGACTGCCTGAG
Original  1863 ATGGCGGATACTCTCCTTCGAGTTTGATGGATCGTAATAGGGACGGGTTGCCTGAA Optimized 1923 AGTATTATTGCTGCTGCTTGTGTAGAAGCGGCGGAGAGTGCTGCATGTGACAGCAGA
Original  1923 TCCATCATTGCAGCTGCATGTCAAGAAGTGGTCGGAGAGTTCTGCATGTTGATTGAAGA Optimized 1983 TCCTACTATGGAGTAACTGGGCCTCTTTCAGCTTTTCGGCCTTCTGAGTGGTTGAAG
Original  1983 AGCTACTATGGAGGAAACTGGCCAGTTTTAGTTTTTCAGGACTATGTCCTGGCTAAAG Optimized 2043 GAGTACCAGGAGAACTCGACAGCGGGTCTAGAGCCCGTGTGGCAGGACCAGATCCTG
Original  2043 GAATACCAGGAAAACAGTGACATTGTAAGTGACAGTCCAGTGTGCAAGACCAGATCCTT Optimized 2103 GAGAATGGCGAGGCCATGGTTCTGTCCAGGAAGTATAAGACATTCAGCACGTGGAGGTG
Original  2103 GAAAATGAACAACCCATTCCTCTAGCACGAAGGACAAAACTATTCAACATGTGCAAGTA Optimized 2163 TTTTGGTATGGCAGTCAGGACTTGGACGAAGATGTGGAGAAGGCAGGGCGCTGCAGAAG
Original  2163 TTTTGTTATGCCAGTCAGGATTTGCATGAAGATGTCGAAGAAGCTGGTGCACTGCAGAAA Optimized 2223 AATCACGTTCTGTGACTTCGCCAATTCTACAGAGCCCGCGATTCTGCTTTCTGCCT
Original  2223 AATCATGCTCTTGTGACATCTGCAAACTCCACAGAAGCTGCAGATTCTGCTTCCTGCCT Optimized 2283 ACGGAGGATGAGTTCCTGTTTACAATGCTTGTGAGATCCTGACGGAGCAGAACCTAGC
Original  2283 ACGGAGGATGAGTCATTAAGCACTAGGAGTTGTGAAATCCTCACAGAACAAATCCAAGC Optimized 2343 TCTGATCCAGAGAACGGGCTGAGTCAATGGGCGAGGTGACTGCGAGAAGGAGAAC
Original  2343 AGTGATCCAGAGAATGTCTAGAAGTAAATGGTCTGAAGTGACAGGGGAAAAAGAAAAC Optimized 2403 CACTGTGACGATAAGACTTGGTGCAAGGACATCGCCGAGGACATGTGCGAGAACGTG
Original  2403 CATTGTGATGATAAAACTTGTGTGCATCAACTTCAGCAGAAGCATGATGAAAATGTG Optimized 2463 CCTATCGCTGAGGATACCACAGAGCATCCAAGGAAGATGCGAGTCGCTACAGCCGAGC
Original  2463 CCTATAGCAGAAGATACCACAGAGCAACCAAGAAAAACAGAATTACTTACTCACAAATT Optimized 2523 ATCAAGGAGGGCAGGGCTCTTAATATGGACTGGCTGCTAAGCTGCTGTACAGCCGGGC
Original  2523 ATTAAAGAAGGCAGGAGATTTAATATTGATTAGTATCAAAGCTGCTGTATTCTGAGGA Optimized 2583 CTGCTGATCGATCTGCTGATCAAGAGCAATGTGGCCGAGATGCGAGGTCAAGAATATC
Original  2583 TTACTAATTGATCTGCTAATCAAATCTAATGTTAGTGATATGCAGAGTTAAAAATATT Optimized 2643 ACCAGAATCCTGGCTTTCGGAAGGAAGAGTGGAACAGGTGCCTGTGTTCAGAGCAGATC
Original  2643 ACCAGGATTCTTGCATTCGAGAAGGACGAGTGAACAGGTTCCGTGTTCAGAGCAGAT Optimized 2703 GTGTTCAACTCCAAGCAGCTGACAATGGTGCAGAAGAGGATGCTGATGAAGTTCCTGACA
Original  2703 GTCTTTAATAGCAAACAACTTACTATGGTAGAAAAGCGAATGCTAATGAAATTCTTACA Optimized 2763 TTTTGTATGGAGTACGAGAAGTATCCAGATGAGTACAAGGTATGGGAGATCACCTTT
Original  2763 TTTTGTATGGAATATGAGAAATATCCTGATGAATATAAGGATATGAAGAGATCACATTT Optimized 2823 TACGAGTATCTGAAGACCCAGAAGCTGACAGCCCAATCTGCAGTAGATCGTGATGCACTGC
Original  2823 TATGAATATTTAAAGACTCAAAAATTAACTGCCAACCTCCAATATATTGTGATGCATTCA Optimized 2883 ATGGCCATGACGTTGAGACAGCCTCTAGCACTATGACGGCTGAAGGCACAAAAGAAC
Original  2883 ATTGCAATGACATCAGAGACAGCCAGCAGCACCATAGATGGTCTCAAAGCTACCAAAAAC Optimized 2943 TTCCTCCACGCTGTGCCGCTGTAGCAATACACCTTCCTGTTCCTCTGTATGGCCAG
Original  2943 TTCTTCACTGCTGCGCTGTATGCAACACTCCATTTTGTTCCTTATATGGCCAA Optimized 3003 GGGGAGCTCCCCAGTGCTTCTGTAGAAGTGCGCGTGTTTGCGGATATTCCTG
Original  3003 GGAGAACTCCCCAGTTTCTGCAGGATCTGTCGTGTTTGCTGGAATTTATTGTCTT Optimized 3063 AGCCACTCTCGTGCAGTGGCGTGTGGGAACAGAAGCCGGAGCGTAAGGCCATCATC
```

Figure 7 (continued)

```
Original   3063  CGCCATTCAGTACAGTGCCTTGTAGTGGACAAACAATCCAGAAAATGTAAACAATTATA Optimized  3123  GATCAGTTTGGCCAGCGAATAATCTCTGAGCACTTCCTGGTGGAGGACAGCTACTTTCCT
Original   3123  GATCAGTTTGGTCAGAGAATAATCTCTGAGCATTCCTCGTGGAGGACAGTTACTTTCCT Optimized  3183  GAGAACATCGTGCTCCAGCGTGCAGTACCGCCAGATCAGCCAGGCAGCGTGATCACCGAT
Original   3183  GAGAACATCGTGCTCCACGTGTCCAATACAGGCAGATCTCCAGGCAGCGTGATTACAGAT Optimized  3243  AGATCCGTGCTGAACACAGACACCGATCAGCAGATCAGCATCCTGACCGTGCAGCAGAG
Original   3243  AGATCTGTCCTAAAAACAGATTCAGATCAACAGATTCCATTTTGACAGTGCAGCAGAG Optimized  3303  GAGCCAGCCACCTTCCGGTGAGAGTGATCGAGCTGTGCTCCTCTACCAGGACATGTATG
Original   3303  GAACCAGGAACTTTTGCTGTTCGGGTCATTGAGTTATGTTCTTCAACGATGACATGCATG Optimized  3363  AAGGCGACCTACTTGGTCACCTGACCTGCACAAGCTCAAGACACCCGGGAGACTTG
Original   3363  AAAGGCACCTATTTGGTCATTTGACTTGCACATCTTCTAAACAGCAAGAGAAGATTTA Optimized  3423  GAGAGCCGCGCAGAAGCTGTTCGTCCCCTACACCAGATGGAGATCGAGAGCAAGGAG
Original   3423  GAATCAGTTGTCCAGAAATTGTTCGTCCATATACCGAAATGGAGATAGGAAATGAACAA Optimized  3483  GTGGAGAAGCTAGAATCTGTGGGCTCTGTACTTCAACATGAGATACTCTAGCGATATC
Original   3483  GTAGAAAAGCCAAGAATTCTGTGGCTCTTACTTCAATATGAGAGATTCGTCAGACATC Optimized  3543  TGTAGGAGCTGTTACAACGATCTGCCCTAAGCTGTACCTGTGCAGCGGACCTGACTGT
Original   3543  AGCAGGAGCTGTTATAATCATTTACCATCAAGCTTATCTGCTCTGGCCAGATGT Optimized  3603  GCCCTGGAAACGATAATGCCGTGAAGCAGGCCGAGACATGTTCCAGGAGATTTGCCCT
Original   3603  GGTTTAAGAAATGATAATGCAGTGAAGCAGCTGAACACTTTCCAGGAAATCTGCCCC Optimized  3663  AACGAGGACTTTGTCCCCCTCCACCAAGCGAGAGATATCATCCGAGCCGAGTTCC
Original   3663  AATGAAGATTCTGTCCCCCTCCACCAAAACCTGAAGACATTATCCTTGATGGAGACAGT Optimized  3723  CTGCAGCCAGAGCCCTGTGAGTCCTTGCCATCCCGAGCCCAATACCGAAACATTCAAA
Original   3723  TTACAGCCAGAGGCTTCAGAATCCAGTGCCATACCAGAGCTAACTGGAGACTTCAAG Optimized  3783  GAAAGCACAAATCGGGAAACCTGAAGAAAGTAGCGACTAA
Original   3783  GAAAGCACAAACCTTGGAAACCTAGAGGAGTCCTGAATAA
```

CODON OPTIMIZED REP1 GENES AND USES THEREOF

CROSS-REFERENCE TO RELATED APPLICATIONS

This application is a continuation of U.S. patent application Ser. No. 17/463,262, filed Aug. 31, 2021, which claims the benefit of U.S. Provisional Patent Application Ser. No. 63/073,837, filed Sep. 2, 2020, the full disclosure of each of which is incorporated herein by reference.

SEQUENCE LISTING SUBMISSION VIA EFS-WEB

A computer readable text file, entitled "090400-5011-US-Sequence-Listing" created on or about Aug. 31, 2021, with a file size of about 27 KB contains the sequence listing for this application and is hereby incorporated by reference in its entirety.

BACKGROUND OF THE INVENTION

Choroideremia is a rare, X-linked recessive form of hereditary retinal degeneration that affects roughly 1 in 50,000 males. The disease causes a gradual loss of vision, starting with childhood night blindness, followed by peripheral vision loss and progressing to loss of central vision later in life. Progression continues throughout the individual's life, but both the rate of change and the degree of visual loss are variable among those affected, even within the same family.

Choroideremia is caused by a loss-of-function mutation in the CHM gene which encodes Rab escort protein-1 (REP1), a protein involved in lipid modification of Rab proteins. While the complete mechanism of disease is not fully understood, the lack of a functional protein in the retina results in cell death and the gradual deterioration of the retinal pigment epithelium (RPE), photoreceptors and the choroid.

Although there are currently no approved treatments for choroideremia, several preclinical studies support the use of wild type cDNA of CHM to rescue the choroideremia disease phenotype. However, suboptimal expression level of the wild type sequence in human photoreceptors and RPE are challenges to gene therapy approaches to treat choroideremia.

SUMMARY OF THE INVENTION

Disclosed are codon optimized nucleic acid molecules encoding a human Rab escort protein-1 (REP1) protein. In one aspect, the disclosure provides a nucleic acid comprising the nucleotide sequence of SEQ ID NO:1 or a nucleic acid comprising a nucleotide sequence at least 90%, at least 95%, at least 96%, at least 97%, at least 98%, or at least 99% identical to the nucleotide sequence of SEQ ID NO:1 and which encodes a human REP1 polypeptide having the amino acid sequence of SEQ ID NO:2. In some embodiments, a nucleic acid comprising or consisting of the nucleotide sequence of SEQ ID NO:1 is provided. In related embodiments, the nucleic acid is expressed at a higher level compared with the level of expression of a wild type CHM nucleic acid sequence (e.g. SEQ ID NO:3) in an otherwise identical cell.

In some aspects, a codon optimized nucleic acid molecule as herein described has a human codon adaptation index that is increased relative to that of the wild type CHM cDNA (GenBank Accession No. NM_000390.4; SEQ ID NO:3). In some embodiments, the codon optimized nucleic acid molecule has a human codon adaptation index of at least about 0.9, at least about 0.92, or at least about 0.94.

In certain embodiments, the nucleic acid contains a higher percentage of G/C nucleotides compared to the percentage of G/C nucleotides in SEQ ID NO:3. In other embodiments, the nucleic acid contains a percentage of G/C nucleotides that is at least about 55%, at least about 57.5%, at least about 60% or at least about 61%. In some aspects, the nucleic acid contains a percentage of G/C nucleotides that is from about 55% to about 70%, from about 57.5% to about 70% or from about 61% to about 70%.

In other embodiments, the nucleic acid comprises one or more optimized parameters relative to SEQ ID NO:3: frequency of optimal codons; reduction in maximum length of direct repeat sequences; removal of restriction enzymes, including without limitation, removal of Bglll(AGATCT); removal of CIS-acting elements, including without limitation, and removal of destabilizing (ATTTA) elements.

In another embodiment, the nucleic acid is operatively linked to at least one transcription control sequence, preferably a transcription control sequence that is heterologous to the nucleic acid. In some aspects, the transcription control sequence is a cell- or tissue-specific promoter that results in cell-specific expression of the nucleic acid e.g. in photoreceptor cells such as vitelliform macular dystrophy 2 promoter which is selectively expressed in the RPE. In other aspects, the transcription control sequence is a constitutive promoter that results in similar expression level of the nucleic acid in many cell types (e.g. a CAG, CBA (chicken beta actin), CMV, or PGK promoter). In preferred embodiments, the transcription control sequence comprises a CAG promoter comprising (i) the cytomegalovirus (CMV) early enhancer element, (ii) the promoter, first exon and first intron of chicken beta-actin gene and (iii) the splice acceptor of the rabbit beta-globin gene as described in Miyazaki et al., Gene 79(2):269-77 (1989). In a particularly preferred embodiment, the CAG promoter comprises the sequence of SEQ ID NO:4 or comprises a sequence at least 95%, at least 96%, at least 97%, at least 98% or at least 99% identical thereto:

```
                                              (SEQ ID NO: 4)
ACTAGTTATTAATAGTAATCAATTACGGGGTCATTAGTTCATAGCCCAT

ATATGGAGTTCCGCGTTACATAACTTACGGTAAATGGCCCGCCTGGCTG

ACCGCCCAACGACCCCCGCCCATTGACGTCAATAATGACGTATGTTCCC

ATAGTAACGCCAATAGGGACTTTCCATTGACGTCAATGGGTGGAGTATT

TACGGTAAACTGCCCAGTTGGCAGTACATCAAGTGTATCATATGCCAAG

TACGCCCCCTATTGACGTCAATGACGGTAAATGGCCCGCCTGGCATTAT

GCCCAGTACATGACCTTATGGGACTTTCCTACTTGGCAGTACATCTACG

TATTAGTCATCGCTATTACCATGGTCGAGGTGAGCCGCACGTTCTGCTT

CACTCTCCCCATCTCCCCCCCCTCCCCACCCCCAATTTTGTATTTATTT

ATTTTTTAATTATTTTGTGCAGCGATGGGGCGGGGGGGGGGGGGGGC

GCGCGCCAGGCGGGGCGGGGCGGGGCGAGGGCGGGGCGGGGCGAGGCG

GAGAGGTGCGGCGGCAGCCAATCAGAGCGGCGCGCTCCGAAAGTTTCCT

TTTATGGCGAGGCGGCGGCGGCGGCGGCCCTATAAAAAGCGAAGCGCGC
```

-continued

```
GGCGGGCGGGGAGTCGCTGCGACGCTGCCTTCGCCCCGTGCCCCGCTCC

GCCGCCGCCTCGCGCCGCCCGCCCCGGCTCTGACTGACCGCGTTACTCC

CACAGGTGAGCGGGCGGGACGGCCCTTCTCCTCCGGGCTGTAATTAGCG

CTTGGTTTAATGACGGCTTGTTTCTTTTCTGTGGCTGCGTGAAAGCCTT

GAGGGGCTCCGGGAGGGCCCTTTGTGCGGGGGGAGCGGCTCGGGGGGTG

CGTGCGTGTGTGTGCGTGGGGAGCGCCGCGTGCGGCTCCGCGCTGCC

CGGCGGCTGTGAGCGCTGCGGGCGCGGCGCGGGGCTTTGTGCGCTCCGC

AGTGTGCGCGAGGGGAGCGCGGCCGGGGGCGGTGCCCCGCGGTGCGGGG

GGGGCTGCGAGGGGAACAAAGGCTGCGTGCGGGTGTGTGCGTGGGGGG

GTGAGCAGGOGGTGTGGGCGCGTCGGTGGGGCTGCAACCCCCCCTGCAC

CCCCCTCCCCGAGTTGCTGAGCACGGCCCGGCTTCGGGTGCGGGGCTCC

GTACGGGGCGTGGCGCGGGGCTCGCCGTGCCGGGCGGGGGGTGGCGGCA

GGTGGGGGTGCCGGGCGGGGCGGGGCCGCCTCGGGCCGGGGAGGGCTCG

GGGGAGGGGCGGGGCGGCCCCCGGAGGGCCGGCGGCTGTCGAGGCGCGG

CGAGCCGCAGCCATTGCCTTTTATGGTAATCGTGCGAGAGGGCGCAGGG

ACTTCCTTTGTCCCAAATCTGTGCGGAGCCGAAATCTGGGAGGCGCCGC

CGCACGCCCTGTAGCGGGCGCGGGGCGAAGCGGTGCGGCGCCGGCAGGA

AGGAAATGGGCGGGGAGGGCCTTCGTGCGTCGCCGCGCCGCCGTCCCCT

TCTCCCTCTCCAGCCTCGGGGCTGTCCGCGGGGGGACGGCTGCCTTCGG

GGGGACGGGGCAGGGCGGGGTTCGGCTTCTGGCGTGTGACCGGCGGCT

CTAGAGCCTCTGCTAACCATGTTCATGGCTTCTTCTTTTTCCTACAG
```

The transcription control sequence may also comprise one or more elements downstream of the REP1 coding sequence such as a Woodchuck hepatitis virus posttranscriptional regulatory element (WPRE), which has been shown to enhance AAV transgene expression in the retina. In related embodiments, provided herein is an expression cassette comprising a nucleic acid comprising the nucleotide sequence of SEQ ID NO:1, or a nucleotide sequence at least 90% identical thereto, operably linked to an expression control sequence.

In related embodiments, provided herein is a vector comprising a nucleic acid comprising the nucleotide sequence of SEQ ID NO:1, or a nucleotide sequence at least 90% identical thereto. In preferred embodiments, the vector is a recombinant adeno-associated (rAAV) expression vector. In some embodiments, the rAAV vector comprises a native capsid (e.g. a capsid of AAV serotype 2, AAV serotype 4, AAV serotype 5 or AAV serotype 8). In other embodiments, the rAAV vector comprises a capsid that is modified (e.g. comprises one or more peptide insertions and/or one or more amino acid substitutions (e.g. tyrosine to phenylalanine) and/or amino acid insertions or amino acid deletions) relative to a native AAV capsid (e.g. comprising one or more modifications relative to an AAV capsid of serotype 2, 4, 5 or 8).

In another embodiment, provided herein is a host cell comprising a nucleic acid comprising the nucleotide sequence of SEQ ID NO:1, or a nucleotide sequence at least 90% identical thereto. In some aspects, the host cell is a mammalian cell, including without limitation, a CHO cell, an HEK293 cell, a HeLa cell, a BHK21 cell, a Vero cell or a V27 cell. In related aspects, the host cell is selected from a CHO cell, an HEK293 cell, an HEK293T cell, a HeLa cell, a BHK21 cell and a Vero cell. In other aspects, the host cell is a photoreceptor cell (e.g. rods; cones), a retinal ganglion cell (RGC), a glial cell (e.g. a Muller glial cell, a microglial cell), a bipolar cell, an amacrine cell, a horizontal cell, or a retinal pigmented epithelium (RPE) cell. In related embodiments, the disclosure provides a method of increasing expression of a polypeptide of SEQ ID NO: 2 comprising culturing the host cell under conditions whereby a polypeptide of SEQ ID NO: 2 is expressed by the nucleic acid molecule, wherein the expression of the polypeptide is increased relative to a host cell cultured under the same conditions comprising a reference nucleic acid comprising the nucleotide sequence of SEQ ID NO:3 (comparator sequence).

In another embodiment, the disclosure provides a method of increasing expression of a polypeptide of SEQ ID NO: 2 in a human subject comprising administering to the subject an isolated nucleic acid molecule comprising a nucleotide sequence at least 85%, at least 90%, at least 95%, at least 96%, at least 97%, at least 98%, at least 99% identical, or 100% identical to the nucleotide sequence of SEQ ID NO:1 and which encodes a polypeptide having the amino acid sequence of SEQ ID NO:2 or a vector comprising such a nucleotide sequence, wherein the expression of the polypeptide is increased relative to a reference nucleic acid molecule comprising the nucleotide sequence of SEQ ID NO:3 (comparator sequence) or a vector comprising the reference nucleic acid molecule.

In some embodiments, the disclosure provides a method of treating an ocular disorder associated with insufficient REP1 activity in a human subject comprising administering to the subject a nucleic acid molecule or a vector disclosed herein. In some embodiments, the retinal disorder is choroideremia.

DESCRIPTION OF THE DRAWINGS

FIGS. 1C and 1D illustrate representative images of CHM1 (FIG. 1C) and CHM2 (FIG. 1D) cultures randomly differentiated into ectodermal, mesodermal and endodermal cell lineages as indicted by expression of TUJ1, α-smooth muscle actin (ASMA) and Hepatocyte Nuclear Factor 4 Alpha (HNF4A).

FIG. 2C is a graph illustrating that CHM1 RPE and CHM2 RPE phagocytose at similar levels to wild type (WT) RPE. In addition, phagocytosis occurs through the known mechanism in vivo, αVβ5 integrin binding, as seen by a decrease in phagocytosis following αVβ5 inhibition. n=3 for quantitative measurements; Error bars±S.D.; *$p<0.05$, compared to the "No ROS" condition; two-tailed t-test.

FIGS. 3A-B FIG. 3A: Western blot images are shown illustrating REP1 and housekeeping protein GADPH levels in CHM1 RPE or normal iPSC-derived RPE cells following transduction with recombinant AAV virions carrying the codon optimized REP1 gene or carrying the unmodified REP1 gene, in each case driven by a CAG promoter. The codon optimized REP1 showed significantly higher levels of protein expression. FIG. 3B: band intensity was quantified and graphed as a ratio over GAPDH. n=3 for quantitative measurements; Error bars±S.D.; *p<0.05, compared to the WT-REP1; two-tailed t-test.

FIGS. 5A-5D Transduction of CHM1 and CHM2 RPE with rAAV virions comprising codon optimized REP1 of SEQ ID NO:1 under the control of a CAG promoter restored prenylation of Rab27a GTPase. FIGS. 5A and 5B: Gel images illustrating the level of REP1 protein by Western blot analysis and incorporation of a biotinylated prenyl donor as a measure of prenylation in cell lysates, in transduced and untransduced CHM1 (FIG. 5A) and CHM2 (FIG. 5B) RPE cells (compared to normal iPSC-derived RPE cells). FIGS. 5C and 5D: Band intensity was quantified and depicted in bar graphs as biotinylated Rab27a GTPase relative to the housekeeping protein GADPH, in CHM1 (FIG. 5C) and CHM2 (FIG. 5D) RPE cells. n=3 for quantitative measurements; Error bars±S.D.; *p<0.05, compared to the untreated CHM RPE; two-tailed t-test.

FIGS. 6A-6C FIG. 6A: Immunostaining of CHM1 RPE with anti-REP1 and anti-RAB27A antibodies illustrates that CHM1 RPE lacked proper membrane localization of Rab27a GTPase. FIGS. 6B and 6C: Delivery of codon optimized REP1 of SEQ ID NO:1 by rAAV vector, corrected Rab27 GTPase membrane trafficking in CHM1 RPE (FIG. 6B), and restored localization to a control RPE phenotype (FIG. 6C).

FIG. 7 DNA alignment of the optimized region of SEQ ID NO:1 with native REP1 of SEQ ID NO:3.

DETAILED DESCRIPTION OF THE INVENTION

Definitions

Figure 1A:
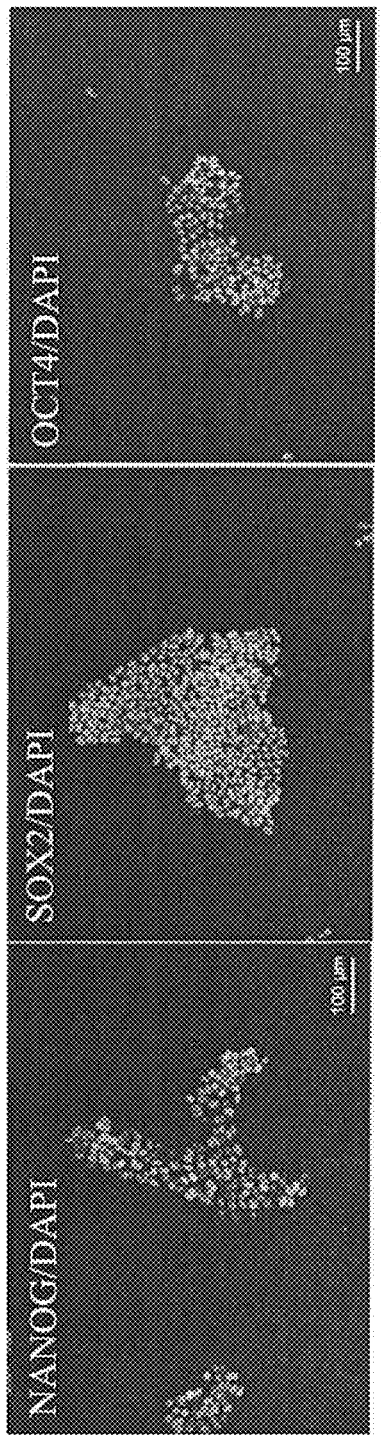
FIGS. 1A-D FIGS. 1A and 1B illustrate immunocytochemical analysis of iPSCs derived from choroideremia patients CHM1 (FIG. 1A) and CHM2 (FIG. 1B) using antibodies against pluripotent transcription factors NANOG, OCT4 and SOX2.

A "codon adaptation index," as used herein, refers to a measure of codon usage bias. A codon adaptation index (CAI) measures the deviation of a given protein coding gene sequence with respect to a reference set of genes (Sharp P M and Li W H, Nucleic Acids Res. 15(3):1281-95 (1987)). CAI is calculated by determining the geometric mean of the weight associated to each codon over the length of the gene sequence (measured in codons):

$$CAI = \exp\left(1/L \sum_{l=1}^{L} \ln(w_1(l))\right), \quad (I)$$

For each amino acid, the weight of each of its codons, in CAI, is computed as the ratio between the observed frequency of the codon (fi) and the frequency of the synonymous codon (fj) for that amino acid:

$$w_i = \frac{f_i}{\max(f_j)} \quad ij \in [\text{synonymous codons for amino acid}] \quad (II)$$

The term "isolated" designates a biological material (cell, nucleic acid or protein) that has been removed from its original environment (the environment in which it is naturally present). For example, a polynucleotide present in the natural state in a plant or an animal is not isolated, however the same polynucleotide separated from the adjacent nucleic acids in which it is naturally present, is considered "isolated."

The term "4D-110" refers to a recombinant AAV particle comprising (i) a capsid protein comprising the amino acid sequence of SEQ ID NO:9 and a heterologous nucleic acid comprising the nucleotide sequence of SEQ ID NO:5.

The term "R100" refers to a variant AAV capsid protein comprising the amino acid sequence of SEQ ID NO:9.

The term "having" as used herein is equivalent to the term "comprising" and is intended to be open-ended allowing additional elements.

As used herein, a "coding region" or "coding sequence" is a portion of polynucleotide which consists of codons translatable into amino acids. Although a "stop codon" (TAG, TGA, or TAA) is typically not translated into an amino acid, it can be considered to be part of a coding region, but any flanking sequences, for example promoters, ribosome binding sites, transcriptional terminators, introns, and the like, are not part of a coding region. The boundaries of a coding region are typically determined by a start codon at the 5' terminus, encoding the amino terminus of the resultant polypeptide, and a translation stop codon at the 3' terminus, encoding the carboxyl terminus of the resulting polypeptide. Two or more coding regions can be present in a single polynucleotide construct, e.g., on a single vector, or in separate polynucleotide constructs, e.g., on separate (different) vectors. It follows, then that a single vector can contain just a single coding region, or comprise two or more coding regions.

As used herein, the term "regulatory region" refers to nucleotide sequences located upstream (5' non-coding sequences), within, or downstream (3' non-coding sequences) of a coding region, and which influence the transcription, RNA processing, stability, or translation of the associated coding region. Regulatory regions can include promoters, translation leader sequences, introns, polyadenylation recognition sequences, RNA processing sites, effector binding sites and stem-loop structures. If a coding region is intended for expression in a eukaryotic cell, a polyadenylation signal and transcription termination sequence will usually be located 3' to the coding sequence.

As used herein, the term "nucleic acid" is interchangeable with "polynucleotide" or "nucleic acid molecule" and a polymer of nucleotides is intended.

A polynucleotide which encodes a gene product, e.g., a polypeptide, can include a promoter and/or other transcription or translation control elements operably associated with one or more coding regions. In an operable association a coding region for a gene product, e.g., a polypeptide, is associated with one or more regulatory regions in such a way as to place expression of the gene product under the influence or control of the regulatory region(s). For example, a coding region and a promoter are "operably associated" if induction of promoter function results in the transcription of mRNA encoding the gene product encoded by the coding region, and if the nature of the linkage between the promoter and the coding region does not interfere with the ability of the promoter to direct the expression of the gene product or interfere with the ability of the DNA template to be transcribed. Other transcription control elements, besides a promoter, for example enhancers, operators, repressors, and transcription termination signals, can also be operably associated with a coding region to direct gene product expression.

"Transcriptional control sequences" refer to DNA regulatory sequences, such as promoters, enhancers, terminators, and the like, that provide for the expression of a coding sequence in a host cell. A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit beta-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

The term "expression" as used herein refers to a process by which a polynucleotide produces a gene product, for example, an RNA or a polypeptide. It includes without limitation transcription of the polynucleotide into messenger RNA (mRNA), transfer RNA (tRNA), small hairpin RNA (shRNA), small interfering RNA (siRNA) or any other RNA product, and the translation of an mRNA into a polypeptide. Expression produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation or splicing, or polypeptides with post translational modifications, e.g., methylation, glycosylation, the addition of lipids, association with other protein subunits, or proteolytic cleavage.

A "vector" refers to any vehicle for the cloning of and/or transfer of a nucleic acid into a host cell. A vector can be a replicon to which another nucleic acid segment can be attached so as to bring about the replication of the attached segment. The term "vector" includes both viral and nonviral vehicles for introducing the nucleic acid into a cell in vitro, ex vivo or in vivo. A large number of vectors are known and used in the art including, for example, plasmids, modified eukaryotic viruses, or modified bacterial viruses. Insertion, of a polynucleotide into a suitable vector can be accomplished by ligating the appropriate polynucleotide fragments into a chosen vector that has complementary cohesive termini.

Vectors can be engineered to encode selectable markers or reporters that provide for the selection or identification of cells that have incorporated the vector. Expression of selectable markers or reporters allows identification and/or selection of host cells that incorporate and express other coding regions contained on the vector. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like. Examples of reporters known and used in the art include: luciferase (Luc), green fluorescent protein (GFP), chloramphenicol acetyltransferase (CAT), -galactosidase (LacZ), -glucuronidase (Gus), and the like. Selectable markers can also be considered to be reporters.

Eukaryotic viral vectors that can be used include, but are not limited to, adenovirus vectors, retrovirus vectors, adeno-associated virus vectors, poxvirus, e.g., vaccinia virus vectors, baculovirus vectors, or herpesvirus vectors. Non-viral vectors include plasmids, liposomes, electrically charged lipids (cytofectins), DNA-protein complexes, and biopolymers.

"Promoter" and "promoter sequence" are used interchangeably and refer to a DNA sequence capable of controlling the expression of a coding sequence or functional RNA. In general, a coding sequence is located 3' to a promoter sequence. Promoters can be derived in their entirety from a native gene, or be composed of different elements derived from different promoters found in nature, or even comprise synthetic DNA segments. It is understood by those skilled in the art that different promoters can direct the expression of a gene in different tissues or cell types, or at different stages of development, or in response to different environmental or physiological conditions. Promoters that cause a gene to be expressed in most cell types at most times are commonly referred to as "constitutive promoters." Promoters that cause a gene to be expressed in a specific cell type are commonly referred to as "cell-specific promoters" or "tissue-specific promoters." Promoters that cause a gene to be expressed at a specific stage of development or cell differentiation are commonly referred to as "developmentally-specific promoters" or "cell differentiation-specific promoters." Promoters that are induced and cause a gene to be expressed following exposure or treatment of the cell with an agent, biological molecule, chemical, ligand, light, or the like that induces the promoter are commonly referred to as "inducible promoters" or "regulatable promoters." It is further recognized that since in most cases the exact boundaries of regulatory sequences have not been completely defined, DNA fragments of different lengths can have identical promoter activity.

The term "plasmid" refers to an extra-chromosomal element often carrying a gene that is not part of the central metabolism of the cell, and usually in the form of circular double-stranded DNA molecules. Such elements can be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

A polynucleotide or polypeptide has a certain percent "sequence identity" to another polynucleotide or polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at ncbi.nlm.nih.gov/BLAST/. Another alignment algorithm is FASTA, available in the Genetics Computing Group (GCG) package, from Madison, Wis., USA. Other techniques for alignment are described in Methods in Enzymology, vol. 266: Computer Methods for Macromolecular Sequence Analysis (1996), ed. Doolittle, Academic Press, Inc. Of particular interest are alignment programs that permit gaps in the sequence. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. See J. Mol. Biol. 48: 443-453 (1970).

In one embodiment, the present invention provides a modified nucleic acid molecule comprising a nucleotide sequence that encodes a polypeptide of SEQ ID NO:2 (human REP1), wherein the nucleic acid sequence has been codon optimized. In another embodiment, the starting nucleic acid sequence that encodes a polypeptide of SEQ ID NO:2 and that is subject to codon optimization has the nucleotide sequence set forth as SEQ ID NO:3. In preferred embodiments, the sequence that encodes a polypeptide of SEQ ID NO:2 is codon optimized for human expression. SEQ ID NO:1 is a codon optimized version of SEQ ID NO:3, optimized for human expression:

(SEQ ID NO: 1)
ATGGCTGATACACTGCCTTCTGAGTTTGATGTGATCGTGATTGGAACTG

GACTGCCTGAGAGTATTATTGCTGCTGCTTGTAGTAGAAGCGGCCGGAG

AGTGCTGCACGTGGACAGCAGATCCTACTATGGCGGCAACTGGGCCTCT

TTCAGCTTTTCCGGCCTGCTGAGCTGGCTGAAGGAGTACCAGGAGAACT

CCGACATCGTGTCTGATAGCCCCGTGTGGCAGGACCAGATCCTGGAGAA

TGAGGAGGCCATCGCCCTGTCCAGGAAGGATAAGACCATCCAGCACGTG

GAGGTGTTCTGCTATGCCAGCCAGGACCTGCACGAGGATGTGGAGGAGG

CAGGCGCCGTGCAGAAGAACCACGGCCTGGTGACCTCCGCCAATTCTAC

AGAGGCCGCCGACTCCGCCTTTCTGCCTACCGAGGATGAGTCCCTGTCT

ACAATGTCTTGTGAGATGCTGACCGAGCAGACACCTAGCTCCGATCCAG

AGAACGCCCTGGAGGTCAATGGCGCCGAGGTGACCGGCGAGAAGGAGAA

CCACTGCGACGATAAGACCTGCGTGCCAAGCACATCCGCCGAGGACATG

TCCGAGAACGTGCCTATCGCCGAGGATACCACAGAGCAGCCAAAGAAGA

ATCGCATCACATACAGCCAGATCATCAAGGAGGGCAGGCGCTTCAATAT

CGACCTGGTGTCTAAGCTGCTGTACAGCCGGGGCCTGCTGATCGATCTG

CTGATCAAGAGCAACGTGTGCCGCTATGCCGAGTTCAAGAATATCACCA

GAATCCTGGCCTTTCGGGAGGGAAGAGTGGAGCAGGTGCCCTGCAGCAG

AGCCGACGTGTTCAACTCCAAGCAGCTGACAATGGTGGAGAAGAGGATG

CTGATGAAGTTCCTGACATTTTGTATGGAGTACGAGAAGTATCCAGATG

AGTACAAGGGCTATGAGGAGATCACCTTTTACGAGTATCTGAAGACCCA

GAAGCTGACACCCAATCTGCAGTACATCGTGATGCACTCCATCGCCATG

ACCTCTGAGACAGCCTCTAGCACCATCGACGGCCTGAAGGCCACAAAGA

ACTTCCTGCACTGCCTGGGCCGGTACGGCAATACACCCTTCCTGTTTCC

TCTGTATGGCCAGGGCGAGCTGCCCCAGTGCTTCTGTAGAATGTGCGCC

GTGTTTGGCGGCATCTATTGCCTGAOGCACTCTGTGCAGTGTCTGGTGG

TGGACAAGGAGAGCCGCAAGTGTAAGGCCATCATCGATCAGTTTGGCCA

GCGGATCATCTCTCAGCACTTCCTGGTGGAGGACAGCTACTTTCCTGAG

AACATGTGCTCGAGGGTGCAGTATCGCCAGATCAGCCGGGCGGTGCTGA

TCACCGATAGATCCGTGCTGAAGACAGACAGCGATCAGCAGATCAGCAT

CCTGACCGTGCGAGCAGAGGAGCCAGGCACCTTCGCCGTGAGAGTGATC

GAGCTGTGCTCCTCTACCATGACATGTATGAAGGGCACCTAGCTGGTGC

ACCTGACCTGCACAAGCTCCAAGACAGCGCGCGAGGACCTGGAGAGCGT

GGTGCAGAAGCTGTTCGTGCCCTACACCGAGATGGAGATCGAGAACGAG

CAGGTGGAGAAGCCTAGAATCCTGTGGGCCCTGTACTTCAACATGAGAG

ACTCTAGCGATATCTCTAGGAGCTGTTACAACGATCTGCCCTCTAACGT

GTACGTGTGCAGCGGACCTGACTGTGGCCTGGGAAAGGATAATGCCGTG

AAGCAGGCCGAGACACTGTTCCAGGAGATTTGCCCTAACGAGGACTTTT

GTCCCCCTCCACCCAATCCAGAQGATATCATCCTGGACGGCGATTCCCT

-continued

GCAGCCAGAGGCCTCTGAGTCCTCTGCCATCCCCGAGGCCAATAGCGAA

ACATTCAAAGAAAGCACAAATCTGGGAAACCTGGAAGAAAGTAGTGAGT

AA

In some embodiments, a codon-optimized sequence encoding human REP1 is provided lacking the TAA stop codon of SEQ ID NO:1 (i.e. consisting of nucleotides 1-1959 of SEQ ID NO:1).

In one aspect, the disclosure provides a polynucleotide comprising the nucleotide sequence of SEQ ID NO:1 or polynucleotide comprising a nucleotide sequence at least 90%, at least 95%, at least 96%, at least 97%, at least 98%, or at least 99% identical to the nucleotide sequence of SEQ ID NO:1 and which encodes a human REP1 polypeptide having the amino acid sequence of SEQ ID NO:2:

(SEQ ID NO: 2)
MADTLPSEFDVIVIGTGPLPESIIAAACSRSGRRVLHVDSRSYYGGNWA

SFSFSGLLSWLKEYQENSDIVSDSPVWQDQILENEEIALSRKDKTIQHV

EVFCYASQDLHEDVEEAGLQKNHALVTSANSTEAADSAFLPTEDESLST

MSCEMLTEQTPSSDPENALEVNGAEVTGEKENHCDDKTCVPSTSAEDMS

ENVPIAEDTTEQPKKNRITYSQIIKEGRRFNIDLVSKLLYSRGLLIDLL

IKSNVSRYAEFKNITRILAFREGRVEQVPCSRADVFNSKQLTMVEKRML

MKFLTFCMEYEKYPDEYKGYEEITFYEYLKTQKLTPNLQYIVMHSIAMT

SETASSTIDGLKATKNFLHCLGRYGNTPFLFPLYGQGELPQCFCRMCAV

FGGIYCLRHSVQCLVVDKESRKCKAIIDQFGQRIISEHFLVEDSYFPEN

MCSRVQYRQISRAVLITDRSVLKTDSDQQISILTVPAEEPGTFAVRVIE

LCSSTMTCMKGTYVHLTCTSSKTAREDLESVVQKLFVPYTEMEIENEQV

EKPRILWALYFNMRDSSDISRSCYNDLPSNVYVCSGPDCGLGNDNAVKQ

AETLFQEICPNEDFCPPPPNPEDIILDGDSLQPEASESSAIPEANSETF

KESTNLGNLEESSE

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA. Such optimization includes replacing at least one, or more than one, or a significant number, of codons with one or more codons that are more frequently used in the genes of that organism.

Deviations in the nucleotide sequence that comprises the codons encoding the amino acids of, any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 1. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

TABLE-US-00001 TABLE 1 The Standard Genetic Code T C A G T TTT Phe (F) TCT Ser (S) TAT Tyr (Y) TGT Cys (C) TTC Phe (F) TCC Ser (S) TAC Tyr (Y) TGC TTA Leu (L) TCA Ser (S) TAA Stop TGA Stop TTG Leu (L) TCG Ser (S) TAG Stop TGG Trp (W) C CTT Leu (L) CCT Pro (P) CAT His (H) CGT Arg (R) CTC Leu (L) CCC Pro (P) CAC His (H) CGC Arg (R) CTA Leu (L) CCA Pro (P) CAA Gln (Q) CGA Arg (R) CTG Leu (L) CCG Pro (P) CAG Gln (Q) CGG Arg (R) A ATT Ile (I) ACT Thr (T) AAT Asn (N) AGT Ser (S) ATC Ile (I) ACC Thr (T) AAC Asn (N) AGC Ser (S) ATA Ile (1) ACA Thr (T) AAA Lys (K) AGA Arg (R) ATG Met (M) ACG Thr (T) AAG Lys (K) AGG Arg (R) G GTT Val (V) GCT Ala (A) GAT Asp (D) GGT Gly (G) GTC Val (V) GCC Ala (A) GAC Asp (D) GGC Gly (G) GTA Val (V) GCA Ala (A) GAA Glu (E) GGA Gly (G) GTG Val (V) GCG Ala (A) GAG Glu (E) GGG Gly (G)

Many organisms display a bias for use of particular codons to code for insertion of a particular amino acid in a growing peptide chain. Codon preference, or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, the relative frequencies of codon usage have been calculated. Codon usage tables are available, for example, at the "Codon Usage Database" available on the world wide web at kazusa.or.jp/codon/(visited Jun. 18, 2012). See Nakamura, Y., et al. Nucl. Acids Res. 28:292 (2000).

Randomly assigning codons at an optimized frequency to encode a given polypeptide sequence can be done manually by calculating codon frequencies for each amino acid, and then assigning the codons to the polypeptide sequence randomly. Additionally, various algorithms and computer software programs can be used to calculate an optimal sequence.

Non-Viral Vectors

In some embodiments, a non-viral vector (e.g. an expression plasmid) comprising a modified nucleic acid as herein described is provided. Preferably, the non-viral vector is a plasmid comprising a nucleic acid sequence of SEQ ID NO: 1, or a sequence at least 90% identical thereto.

Viral Vectors

In preferred embodiments, a viral vector comprising a modified (codon optimized) nucleic acid as herein described is provided. Preferably, the viral vector comprises a nucleic acid sequence of SEQ ID NO: 1, or a sequence at least 90% identical thereto, operably linked to an expression control sequence. Examples of suitable viral vectors include but are not limited to adenoviral, retroviral, lentiviral, herpesvirus and adeno-associated virus (AAV) vectors.

In a preferred embodiment, the viral vector includes a portion of a parvovirus genome, such as an AAV genome with the rep and cap genes deleted and/or replaced by the modified REP1 gene sequence and its associated expression control sequences. The modified human REP1 gene sequence is typically inserted adjacent to one or two (i.e., is flanked by) AAV TRs or TR elements adequate for viral replication (Xiao et al., 1997, J. Virol. 71(2): 941-948), in place of the nucleic acid encoding viral rep and cap proteins.

Other regulatory sequences suitable for use in facilitating tissue-specific expression of the modified REP1 gene sequence in the target cell may also be included.

In some preferred embodiments, the AAV viral vector comprises a nucleic acid comprising from 5' to 3': (a) an AAV2 terminal repeat (b) a CAG promoter (c) a codon optimized REP1 gene as herein described (d) a polyadenylation sequence and (e) an AAV2 terminal repeat. In a particularly preferred embodiment, the AAV viral vector comprises a nucleic acid (transgene cassette) comprising the sequence of SEQ ID NO:5 or a sequence at least 90%, at least 95%, at least 98% or at least 99% identical thereto:

```
                                                                (SEQ ID NO: 5)
            TTGGCCACTC CCTCTCTGCG CGCTCGCTCG CTCACTGAGG CCGGGCGACC AAAGGTCGCC    60

CGACGCCCGG GCTTTGCCCG GGCGGCCTCA GTGAGCGAGC GAGCGCGCAG AGAGGGAGTG   120

GCCAACTCCA TCACTAGGGG TTCCTATCGA TTGAATTCCC CGGGGATCCA CTAGTTATTA   180

ATAGTAATCA ATTACGGGGT CATTAGTTCA TAGCCCATAT ATGGAGTTCC GCGTTACATA   240

ACTTACGGTA AATGGCCCGC CTGGCTGACC GCCCAACGAC CCCCGCCCAT TGACGTCAAT   300

AATGACGTAT GTTCCCATAG TAACGCCAAT AGGGACTTTC CATTGACGTC AATGGGTGGA   360

GTATTTACGG TAAACTGCCC ACTTGGCAGT ACATCAAGTG TATCATATGC CAAGTACGCC   420

CCCTATTGAC GTCAATGACG GTAAATGGCC CGCCTGGCAT TATGCCCAGT ACATGACCTT   480

ATGGGACTTT CCTACTTGGC AGTACATCTA CGTATTAGTC ATCGCTATTA CCATGGTCGA   540

GGTGAGCCCC ACGTTCTGCT TCACTCTCCC CATCTCCCCC CCTCCCCAC CCCCAATTTT   600

GTATTTATTT ATTTTTTAAT TATTTTGTGC AGCGATGGGG GCGGGGGGGG GGGGGGGCG   660

CGCGCCAGGC GGGGCGGGGC GGGGCGAGGG GCGGGGCGGG GCGAGGCGGA GAGGTGCGGC   720

GGCAGCCAAT CAGAGCGGCG CGCTCCGAAA GTTTCCTTTT ATGGCGAGGC GGCGGCGGCG   780

GCGGCCCTAT AAAAAGCGAA GCGCGCGGCG GGCGGGGAGT CGCTGCGACG CTGCCTTCGC   840

CCCGTGCCCC GCTCCGCCGC CGCCTCGCGC CGCCCGCCCC GGCTCTGACT GACCGCGTTA   900

CTCCCACAGG TGAGCGGGCG GGACGGCCCT TCTCCTCCGG GCTGTAATTA GCGCTTGGTT   960

TAATGACGGC TTGTTTCTTT TCTGTGGCTG CGTGAAAGCC TTGAGGGGCT CCGGGAGGGC  1020

CCTTTGTGCG GGGGGAGCGG CTCGGGGGGT GCGTGCGTGT GTGTGTGCGT GGGGAGCGCC  1080

GCGTGCGGCT CCGCGCTGCC CGGCGGCTGT GAGCGCTGCG GGCGCGGCGC GGGGCTTTGT  1140

GCGCTCCGCA GTGTGCGCGA GGGGAGCGCG GCCGGGGCG GTGCCCCGCG GTGCGGGGG  1200

GGCTGCGAGG GGAACAAAGG CTGCGTGCGG GGTGTGTGCG TGGGGGGGTG AGCAGGGGGT  1260

GTGGGCGCGT CGGTCGGGCT GCAACCCCCC CTGCACCCCC CTCCCCGAGT TGCTGAGCAC  1320

GGCCCGGCTT CGGGTGCGGG GCTCCGTACG GGGCGTGGCG CGGGGCTCGC CGTGCCGGGC  1380

GGGGGGTGGC GGCAGGTGGG GGTGCCGGGC GGGGCGGGGC CGCCTCGGGC CGGGGAGGGC  1440

TCGGGGAGG GGCGCGGCGG CCCCCGGAGC GCCGGCGGCT GTCGAGGCGC GGCGAGCCGC  1500

AGCCATTGCC TTTTATGGTA ATCGTGCGAG AGGGCGCAGG GACTTCCTTT GTCCCAAATC  1560

TGTGCGGAGC CGAAATCTGG GAGGCGCCGC CGCACCCCCT CTAGCGGGCG CGGGGCGAAG  1620

CGGTGCGGCG CCGGCAGGAA GGAAATGGGC GGGGAGGGCC TTCGTGCGTC GCCGCGCCGC  1680

CGTCCCCTTC TCCCTCTCCA GCCTCGGGGC TGTCCGCGGG GGACGGCTG CCTTCGGGGG  1740

GGACGGGCA GGGCGGGGTT CGGCTTCTGG CGTGTGACCG GCGGCTCTAG AGCCTCTGCT  1800

AACCATGTTC ATGCCTTCTT CTTTTTCCTA CAGTCTAGAG TCGACCTGCA GAAGCTTCCA  1860

CCATGGCTGA TACACTGCCT TCTGAGTTTG ATGTGATCGT GATTGGAACT GGACTGCCTG  1920
```

```
AGAGTATTAT TGCTGCTGCT TGTAGTAGAA GCGGCCGGAG AGTGCTGCAC GTGGACAGCA    1980

GATCCTACTA TGGCGGCAAC TGGGCCTCTT TCAGCTTTTC CGGCCTGCTG AGCTGGCTGA    2040

AGGAGTACCA GGAGAACTCC GACATCGTGT CTGATAGCCC CGTGTGGCAG GACCAGATCC    2100

TGGAGAATGA GGAGGCCATC GCCCTGTCCA GGAAGGATAA GACCATCCAG CACGTGGAGG    2160

TGTTCTGCTA TGCCAGCCAG GACCTGCACG AGGATGTGGA GGAGGCAGGC GCCCTGCAGA    2220

AGAACCACGC CCTGGTGACC TCCGCCAATT CTACAGAGGC CGCCGACTCC GCCTTTCTGC    2280

CTACCGAGGA TGAGTCCCTG TCTACAATGT CTTGTGAGAT GCTGACCGAG CAGACACCTA    2340

GCTCCGATCC AGAGAACGCC CTGGAGGTCA ATGGCGCCGA GGTGACCGGC GAGAAGGAGA    2400

ACCACTGCGA CGATAAGACC TGCGTGCCAA GCACATCCGC CGAGGACATG TCCGAGAACG    2460

TGCCTATCGC CGAGGATACC ACAGAGCAGC CAAAGAAGAA TCGCATCACA TACAGCCAGA    2520

TCATCAAGGA GGGCAGGCGC TTCAATATCG ACCTGGTGTC TAAGCTGCTG TACAGCCGGG    2580

GCCTGCTGAT CGATCTGCTG ATCAAGAGCA ACGTGTCCCG CTATGCCGAG TTCAAGAATA    2640

TCACCAGAAT CCTGGCCTTT CGGGAGGGAA GAGTGGAGCA GGTGCCCTGC AGCAGAGCCG    2700

ACGTGTTCAA CTCCAAGCAG CTGACAATGG TGGAGAAGAG GATGCTGATG AAGTTCCTGA    2760

CATTTTGTAT GGAGTACGAG AAGTATCCAG ATGAGTACAA GGGCTATGAG GAGATCACCT    2820

TTTACGAGTA TCTGAAGACC CAGAAGCTGA CACCCAATCT GCAGTACATC GTGATGCACT    2880

CCATCGCCAT GACCTCTGAG ACAGCCTCTA GCACCATCGA CGGCCTGAAG GCCACAAAGA    2940

ACTTCCTGCA CTGCCTGGGC CGGTACGGCA ATACACCCTT CCTGTTTCCT CTGTATGGCC    3000

AGGGCGAGCT GCCCCAGTGC TTCTGTAGAA TGTGCGCCGT GTTTGGCGGC ATCTATTGCC    3060

TGAGGCACTC TGTGCAGTGT CTGGTGGTGG ACAAGGAGAG CCGCAAGTGT AAGGCCATCA    3120

TCGATCAGTT TGGCCAGCGG ATCATCTCTG AGCACTTCCT GGTGGAGGAC AGCTACTTTC    3180

CTGAGAACAT GTGCTCCAGG GTGCAGTATC GCCAGATCAG CCGGGCCGTG CTGATCACCG    3240

ATAGATCCGT GCTGAAGACA GACAGCGATC AGCAGATCAG CATCCTGACC GTGCCAGCAG    3300

AGGAGCCAGG CACCTTCGCC GTGAGAGTGA TCGAGCTGTG CTCCTCTACC ATGACATGTA    3360

TGAAGGGCAC CTACCTGGTG CACCTGACCT GCACAAGCTC CAAGACAGCC CGCGAGGACC    3420

TGGAGAGCGT GGTGCAGAAG CTGTTCGTGC CCTACACCGA TGGAGATC GAGAACGAGC    3480

AGGTGGAGAA GCCTAGAATC CTGTGGGCCC TGTACTTCAA CATGAGAGAC TCTAGCGATA    3540

TCTCTAGGAG CTGTTACAAC GATCTGCCCT CTAACGTGTA CGTGTGCAGC GGACCTGACT    3600

GTGGCCTGGG AAACGATAAT GCCGTGAAGC AGGCCGAGAC ACTGTTCCAG GAGATTTGCC    3660

CTAACGAGGA CTTTTGTCCC CCTCCACCCA ATCCAGAGGA TATCATCCTG GACGGCGATT    3720

CCCTGCAGCC AGAGGCCTCT GAGTCCTCTG CCATCCCCGA GGCCAATAGC GAAACATTCA    3780

AGAAAGCAC AAATCTGGGA AACCTGGAAG AAAGTAGTGA GTAAGCCTCG AGCAGCGCTG    3840

CTCGAGAGAT CTGCGGCCGC GAGCTCGGGG ATCCAGACAT GATAAGATAC ATTGATGAGT    3900

TTGGACAAAC CACAACTAGA ATGCAGTGAA AAAAATGCTT TATTTGTGAA ATTTGTGATG    3960

CTATTGCTTT ATTTGTAACC ATTATAAGCT GCAATAAACA AGTTAACAAC AACAATTGCA    4020

TTCATTTTAT GTTTCAGGTT CAGGGGGAGG TGTGGGAGGT TTTTTAAAGC AAGTAAAACC    4080

TCTACAAATG TGGTATGGCT GATTATGATC AATGCATCCT AGCCGGAGGA ACCCCTAGTG    4140

ATGGAGTTGG CCACTCCCTC TCTGCGCGCT CGCTCGCTCA CTGAGGCCGC CCGGGCAAAG    4200

CCCGGGCGTC GGGCGACCTT TGGTCGCCCG GCCTCAGTGA GCGAGCGAGC GCGCAGAGAG    4260

GGAGTGGCCA A                                                       4271
```

The components of the transgene cassette of SEQ ID NO:5 and their respective locations are identified in Table 2 below:

TABLE 2

| Location (bp) | Component | Length (bp) |
|---|---|---|
| 1-145 | 5' ITR | 145 |
| 170-1833 | CAG promoter | 1664 |
| 1863-3824 | Codon-optimized hREP1 cDNA | 1962 |
| 3867-4111 | SV40 PolyA | 245 |
| 4127-4271 | 3' ITR | 145 |

The 5' ITR has the following sequence:

(SEQ ID NO: 6)
TTGGCCACTCCCTCTCTGCGCGCTCGCTCGCTCACTGAGGCCGGGCGAC
CAAAGGTCGCCCGACGCCCGGGCTTTGCCCGGGCGGCCTCAGTGAGCGA
GCGAGCGCGCAGAGAGGGAGTGGCCAACTCCATCACTAGGGGTTCCT

The 3' ITR has the following sequence:

(SEQ ID NO: 7)
AGCCGGAGGAACCCCTAGTGATGGAGTTGGCCACTCCCTCTCTGCGCGC

TCGCTCGCTCACTGAGGCCGCCCGGGCAAAGCCCGGGCGTCGGGCGACC

TTTGGTCGCCCGGCCTCAGTGAGCGAGCGAGCGCGCAGAGAGGGAGTGG

CCAA

The SV40 polyadenylation sequence has the following sequence:

(SEQ ID NO: 8)
GAGCTCGGGGATCCAGACATGATAAGATACATTGATGAGTTTGGACAAA

CCACAACTAGAATGCAGTGAAAAAAATGCTTTATTTGTGAAATTTGTGA

TGCTATTGCTTTATTTGTAACCATTATAAGCTGCAATAAACAAGTTAAC

AACAACAATTGCATTCATTTTATGTTTCAGGTTCAGGGGGAGGTGTGGG

AGGTTTTTTAAAGCAAGTAAAACCTCTACAAATGTGGTATGGCTGATTA

TGATCAATGCATCCT

Those skilled in the art will appreciate that an AAV vector comprising a transgene and lacking virus proteins needed for viral replication (e.g., cap and rep), cannot replicate since such proteins are necessary for virus replication and packaging. Helper viruses include, typically, adenovirus or herpes simplex virus. Alternatively, as discussed below, the helper functions (E1a, E1b, E2a, E4, and VA RNA) can be provided to a packaging cell including by transfecting the cell with one or more nucleic acids encoding the various helper elements and/or the cell can comprise the nucleic acid encoding the helper protein. For instance, HEK 293 were generated by transforming human cells with adenovirus 5 DNA and now express a number of adenoviral genes, including, but not limited to E1 and E3 (see, e.g., Graham et al., 1977, J. Gen. Virol. 36:59-72). Thus, those helper functions can be provided by the HEK 293 packaging cell without the need of supplying them to the cell by, e.g., a plasmid encoding them.

The viral vector may be any suitable nucleic acid construct, such as a DNA or RNA construct and may be single stranded, double stranded, or duplexed (i.e., self complementary as described in WO 2001/92551).

The viral capsid component of the packaged viral vectors may be a parvovirus capsid. AAV Cap and chimeric capsids are preferred. For example, the viral capsid may be an AAV capsid (e.g., AAV1, AAV2, AAV3, AAV4, AAV5, AAV6, AAV7 AAV8, AAV9, AAV10, AAV11, AAV12, AAV1.1, AAV2.5, AAV6.1, AAV6.3.1, AAV9.45, AAVrh10, AAVrh74, RHM4-1, AAV2-TT, AAV2-TT-S312N, AAV3B-S312N, AAV-LK03, snake AAV, avian AAV, bovine AAV, canine AAV, equine AAV, ovine AAV, goat AAV, shrimp AAV, and any other AAV now known or later discovered. see, e.g., Fields et al., VIROLOGY, volume 2, chapter 69 (4.sup.th ed., Lippincott-Raven Publishers).

In some embodiments, the viral capsid component of the packaged viral vector is a variant of a native AAV capsid (i.e. comprises one or more modifications relative to a native AAV capsid). In some embodiments, the capsid is a variant of an AAV2, AAV5 or AAV8 capsid. In preferred embodiments, the capsid is a variant of an AAV2 capsid, such as those described in U.S. Patent Application Publication Number 2019/0255192A1 (e.g. comprising the amino acid sequence of any of SEQ ID NOs: 42-59). In a particularly preferred embodiment, the capsid comprises a capsid protein having the following amino acid sequence:

(SEQ ID NO: 9)
MAADGYLPDWLEDTLSEGIRQWWKLKPGPPPPKAAERHKDDSRGLVLPGY

KYLGPFNGLDKGEPVNEADAAALEHDKAYDRQLDSGDNPYLKYNHADAEF

QERLKEDTSFGGNLGRAVFQAKKRVLEPLGLVEEPVKTAPGKKRPVEHSP

VEPDSSSGTGKAGQQPARKRLNFGQTGDADSVPDPQPLGQPPAAPSGLGT

NTMATGSGAPMADNNEGADGVGNSSGNWHCDSTWMGDRVITTSTRTWALP

TYNNHLYKQISSQSGASNDNHYFGYSTPWGYFDFNRFHCHFSPRDWQRLI

NNNWGFRPKRLNFKLFNIQVKEVTQNDGTTTIANNLTSTVQVFTDSEYQL

PYVLGSAHQGCLPPFPADVFMVPQYGYLTLNNGSQAVGRSSFYCLEYFPS

QMLRTGNNFTFSYTFEDVPFHSSYAHSQSLDRLMNPLIDQYLYYLSRTNT

PSGTTTQSRLQFSQAGASDIRDQSRNWLPGPCYRQQRVSKTSADNNNSEY

SWTGATKYHLNGRDSLVNPGPAMASHKDDEEKFFPQSGVLIFGKQGSEKT

NVDIEKVMITDEEEIRTTNPVATEQYGSVSTNLQRGNLAISDQTKHARQA

ATADVNTQGVLPGMVWQDRDVYLQGPIWAKIPHTDGHFHPSPLMGGFGLK

HPPPQILIKNTPVPANPSTTFSAAKFASFITQYSTGQVSVEIEWELQKEN

SKRWNPEIQYTSNYNKSVNVDFTVDTNGVYSEPRPIGTRYLTRNL

The variant AAV capsid protein of SEQ ID NO:9 contains the following modifications relative to native AAV2 capsid: (i) a proline (P) to alanine (A) mutation at amino acid position 34, which is located inside the assembled capsid (VP1 protein only), and (ii) an insertion of 10 amino acids (leucine-alanine-isoleucine-serine-aspartic acid-glutamine-threonine-lysine-histidine-alanine/LAISDQTKHA) at amino acid position 588, which is present in VP1, VP2, and VP3.

A full complement of AAV Cap proteins includes VP1, VP2, and VP3. The ORF comprising nucleotide sequences encoding AAV VP capsid proteins may comprise less than a full complement AAV Cap proteins or the full complement of AAV Cap proteins may be provided.

In yet another embodiment the present invention provides for the use of ancestral AAV vectors for use in therapeutic in vivo gene therapy. Specifically, in silico-derived sequences were synthesized de novo and characterized for biological activities. This effort led to the generation of nine functional putative ancestral AAVs and the identification of Anc80, the predicted ancestor of AAV serotypes 1, 2, 8 and 9 (Zinn et al., 2015, Cell Reports 12:1056-1068). Predicting and synthesis of such ancestral sequences in addition to assembling into a virus particle may be accomplished by using the methods described in WO 2015/054653, the contents of which are incorporated by reference herein. Notably, the use of the virus particles assembled from ancestral viral sequences may exhibit reduced susceptibility to pre-existing immunity in current day human population than do contemporary viruses or portions thereof.

The invention includes packaging cells, which are encompassed by "host cells," which may be cultured to produce packaged viral vectors of the invention. The packaging cells of the invention generally include cells with heterologous (1) viral vector function(s), (2) packaging function(s), and (3) helper function(s). Each of these component functions is discussed in the ensuing sections.

Initially, the vectors can be made by several methods known to skilled artisans (see, e.g., WO 2013/063379). A preferred method is described in Grieger, et al. 2015, Molecular Therapy 24(2):287-297, the contents of which are incorporated by reference herein for all purposes. Briefly, efficient transfection of HEK293 cells is used as a starting point, wherein an adherent HEK293 cell line from a qualified clinical master cell bank is used to grow in animal component-free suspension conditions in shaker flasks and WAVE bioreactors that allow for rapid and scalable rAAV production. Using the triple transfection method (e.g., WO 96/40240), the suspension HEK293 cell line generates greater than $10^5$ vector genome containing particles (vg)/cell or greater than $10^{14}$ vg/L of cell culture when harvested 48 hours post-transfection. More specifically, triple transfection refers to the fact that the packaging cell is transfected with three plasmids: one plasmid encodes the AAV rep and cap genes, another plasmid encodes various helper functions (e.g., adenovirus or HSV proteins such as E1a, E1b, E2a, E4, and VA RNA, and another plasmid encodes the transgene and its various control elements (e.g., modified REP1 gene and CAG promoter).

To achieve the desired yields, a number of variables are optimized such as selection of a compatible serum-free suspension media that supports both growth and transfection, selection of a transfection reagent, transfection conditions and cell density. A universal purification strategy, based on ion exchange chromatography methods, was also developed that resulted in high purity vector preps of AAV serotypes 1-6, 8, 9 and various chimeric capsids. This user-friendly process can be completed within one week, results in high full to empty particle ratios (>90% full particles), provides post-purification yields (>$10^{13}$ vg/L) and purity suitable for clinical applications and is universal with respect to all serotypes and chimeric particles. This scalable manufacturing technology has been utilized to manufacture GMP Phase I clinical AAV vectors for retinal neovascularization (AAV2), Hemophilia B (scAAV8), Giant Axonal Neuropathy (scAAV9) and Retinitis Pigmentosa (AAV2), which have been administered into patients. In addition, a minimum of a 5-fold increase in overall vector production by implementing a perfusion method that entails harvesting rAAV from the culture media at numerous time-points post-transfection.

The packaging cells include viral vector functions, along with packaging and vector functions. The viral vector functions typically include a portion of a parvovirus genome, such as an AAV genome, with rep and cap deleted and replaced by the modified REP1 sequence and its associated expression control sequences. The viral vector functions include sufficient expression control sequences to result in replication of the viral vector for packaging. Typically, the viral vector includes a portion of a parvovirus genome, such as an AAV genome with rep and cap deleted and replaced by the transgene and its associated expression control sequences. The transgene is typically flanked by two AAV TRs, in place of the deleted viral rep and cap ORFs. Appropriate expression control sequences are included, such as a tissue-specific promoter and other regulatory sequences suitable for use in facilitating tissue-specific expression of the transgene in the target cell. The transgene is typically a nucleic acid sequence that can be expressed to produce a therapeutic polypeptide or a marker polypeptide.

The terminal repeats (TR(s)) (resolvable and non-resolvable) selected for use in the viral vectors are preferably AAV sequences, with serotypes 1, 2, 3, 4, 5 and 6 being preferred. Resolvable AAV TRs need not have a wild-type TR sequence (e.g., a wild-type sequence may be altered by insertion, deletion, truncation or missense mutations), as long as the TR mediates the desired functions, e.g., virus packaging, integration, and/or provirus rescue, and the like. The TRs may be synthetic sequences that function as AAV inverted terminal repeats, such as the "double-D sequence" as described in U.S. Pat. No. 5,478,745 to Samulski et al., the entire disclosure of which is incorporated in its entirety herein by reference. Typically, but not necessarily, the TRs are from the same parvovirus, e.g., both TR sequences are from AAV2.

The packaging functions include capsid components. The capsid components are preferably from a parvoviral capsid, such as an AAV capsid or a chimeric AAV capsid function. Examples of suitable parvovirus viral capsid components are capsid components from the family Parvoviridae, such as an autonomous parvovirus or a Dependovirus. For example, the capsid components may be selected from AAV capsids, e.g., AAV1, AAV2, AAV3, AAV4, AAV5, AAV6, AAV7, AAV8, AAV9, AAV10, AAV11, AAV12, AAVrh10, AAVrh74, RHM4-1, RHM15-1, RHM15-2, RHM15-3/RHM15-5, RHM15-4, RHM15-6, AAV Hu.26, AAV1.1, AAV2.5, AAV6.1, AAV6.3.1, AAV9.45, AAV2i8, AAV2G9, AAV2i8G9, AAV2-TT, AAV2-TT-S312N, AAV3B-S312N, and AAV-LK03, and other novel capsids as yet unidentified or from non-human primate sources. Capsid components may include components from two or more AAV capsids.

The packaged viral vector generally includes the modified REP1 gene sequence and expression control sequences flanked by TR elements, referred to herein as the "transgene" or "transgene expression cassette," sufficient to result in packaging of the vector DNA and subsequent expression of the modified REP1 gene sequence in the transduced cell. The viral vector functions may, for example, be supplied to the cell as a component of a plasmid or an amplicon. The viral vector functions may exist extrachromosomally within the cell line and/or may be integrated into the cell's chromosomal DNA.

Any method of introducing the nucleotide sequence carrying the viral vector functions into a cellular host for replication and packaging may be employed, including but not limited to, electroporation, calcium phosphate precipitation, microinjection, cationic or anionic liposomes, and liposomes in combination with a nuclear localization signal. In embodiments wherein the viral vector functions are provided by transfection using a virus vector; standard methods for producing viral infection may be used.

The packaging functions include genes for viral vector replication and packaging. Thus, for example, the packaging functions may include, as needed, functions necessary for viral gene expression, viral vector replication, rescue of the viral vector from the integrated state, viral gene expression, and packaging of the viral vector into a viral particle. The packaging functions may be supplied together or separately to the packaging cell using a genetic construct such as a plasmid or an amplicon, a Baculovirus, or HSV helper construct. The packaging functions may exist extrachromosomally within the packaging cell, but are preferably integrated into the cell's chromosomal DNA. Examples include genes encoding AAV Rep and Cap proteins.

The helper functions include helper virus elements needed for establishing active infection of the packaging cell, which is required to initiate packaging of the viral vector. Examples include functions derived from adenovirus, baculovirus and/or herpes virus sufficient to result in packaging of the viral vector. For example, adenovirus helper functions will typically include adenovirus components E1a, E1 b, E2a, E4, and VA RNA. The packaging functions may be supplied by infection of the packaging cell with the required virus. The packaging functions may be supplied together or separately to the packaging cell using a genetic construct such as a plasmid or an amplicon. See, e.g., pXR helper plasmids as described in Rabinowitz et al., 2002, J. Virol. 76:791, and pDG plasmids described in Grimm et al., 1998, Human Gene Therapy 9:2745-2760. The packaging functions may exist extrachromosomally within the packaging cell, but are preferably integrated into the cell's chromosomal DNA (e.g., E1 or E3 in HEK 293 cells).

Any suitable helper virus functions may be employed. For example, where the packaging cells are insect cells, baculovirus may serve as a helper virus. Herpes virus may also be used as a helper virus in AAV packaging methods. Hybrid herpes viruses encoding the AAV Rep protein(s) may advantageously facilitate for more scalable AAV vector production schemes.

Any method of introducing the nucleotide sequence carrying the helper functions into a cellular host for replication and packaging may be employed, including but not limited to, electroporation, calcium phosphate precipitation, microinjection, cationic or anionic liposomes, and liposomes in combination with a nuclear localization signal. In embodiments wherein the helper functions are provided by transfection using a virus vector or infection using a helper virus; standard methods for producing viral infection may be used.

Any suitable permissive or packaging cell known in the art may be employed in the production of the packaged viral vector. Mammalian cells or insect cells are preferred. Examples of cells useful for the production of packaging cells in the practice of the invention include, for example, human cell lines, such as VERO, W138, MRC5, A549, HEK 293 cells (which express functional adenoviral E1 under the control of a constitutive promoter), B-50 or any other HeLa cells, HepG2, Saos-2, HuH7, and HT1080 cell lines. In one aspect, the packaging cell is capable of growing in suspension culture, more preferably, the cell is capable of growing in serum-free culture. In one embodiment, the packaging cell is a HEK293 that grows in suspension in serum free medium. In another embodiment, the packaging cell is the HEK293 cell described in U.S. Pat. No. 9,441,206 and deposited as ATCC No. PTA 13274. Numerous rAAV packaging cell lines are known in the art, including, but not limited to, those disclosed in WO 2002/46359. In another aspect, the packaging cell is cultured in the form of a cell stack (e.g. 10-layer cell stack seeded with HEK293 cells).

Cell lines for use as packaging cells include insect cell lines. Any insect cell which allows for replication of AAV and which can be maintained in culture can be used in accordance with the present invention. Examples include *Spodoptera frugiperda*, such as the Sf9 or Sf21 cell lines, *Drosophila* spp. cell lines, or mosquito cell lines, e.g., *Aedes albopictus* derived cell lines. A preferred cell line is the *Spodoptera frugiperda* Sf9 cell line. The following references are incorporated herein for their teachings concerning use of insect cells for expression of heterologous polypeptides, methods of introducing nucleic acids into such cells, and methods of maintaining such cells in culture: Methods in Molecular Biology, ed. Richard, Humana Press, N J (1995); O'Reilly et al., Baculovirus Expression Vectors: A Laboratory Manual, Oxford Univ. Press (1994); Samulski et al., 1989, J. Virol. 63:3822-3828; Kajigaya et al., 1991, Proc. Nat'l. Acad. Sci. USA 88: 4646-4650; Ruffing et al., 1992, J. Virol. 66:6922-6930; Kimbauer et al., 1996, Virol. 219: 37-44; Zhao et al., 2000, Virol. 272:382-393; and Samulski et al., U.S. Pat. No. 6,204,059.

Virus capsids according to the invention can be produced using any method known in the art, e.g., by expression from a baculovirus (Brown et al., (1994) Virology 198:477-488). As a further alternative, the virus vectors of the invention can be produced in insect cells using baculovirus vectors to deliver the rep/cap genes and rAAV template as described, for example, by Urabe et al., 2002, Human Gene Therapy 13:1935-1943.

In another aspect, the present invention provides for a method of rAAV production in insect cells wherein a baculovirus packaging system or vectors may be constructed to carry the AAV Rep and Cap coding region by engineering these genes into the polyhedrin coding region of a baculovirus vector and producing viral recombinants by transfection into a host cell. Notably when using Baculavirus production for AAV, preferably the AAV DNA vector product is a self-complementary AAV like molecule without using mutation to the AAV ITR. This appears to be a by-product of inefficient AAV rep nicking in insect cells which results in a self-complementary DNA molecule by virtue of lack of functional Rep enzyme activity. The host cell is a baculovirus-infected cell or has introduced therein additional nucleic acid encoding baculovirus helper functions or includes these baculovirus helper functions therein. These baculovirus viruses can express the AAV components and subsequently facilitate the production of the capsids.

During production, the packaging cells generally include one or more viral vector functions along with helper functions and packaging functions sufficient to result in replication and packaging of the viral vector. These various functions may be supplied together or separately to the packaging cell using a genetic construct such as a plasmid or an amplicon, and they may exist extrachromosomally within the cell line or integrated into the cell's chromosomes.

The cells may be supplied with any one or more of the stated functions already incorporated, e.g., a cell line with one or more vector functions incorporated extrachromosomally or integrated into the cell's chromosomal DNA, a cell line with one or more packaging functions incorporated extrachromosomally or integrated into the cell's chromosomal DNA, or a cell line with helper functions incorporated extrachromosomally or integrated into the cell's chromosomal DNA.

The rAAV vector may be purified by methods standard in the art such as by column chromatography or cesium chloride gradients. Methods for purifying rAAV vectors are known in the art and include methods described in Clark et al., 1999, Human Gene Therapy 10(6):1031-1039; Schenpp and Clark, 2002, Methods Mol. Med. 69:427-443; U.S. Pat. No. 6,566,118 and WO 98/09657.

Treatment Methods

In certain embodiments, a method is provided for the treatment of choroideremia in a subject in need of such treatment by administering to the subject a therapeutically effective amount of a nucleic acid having a nucleotide sequence at least 90%, at least 95%, at least 98% identical, or 100% identical to the nucleotide sequence of SEQ ID NO:1 or a pharmaceutical composition comprising such a nucleic acid and at least one pharmaceutically acceptable excipient.

In related aspects, a nucleic acid comprising a nucleotide sequence at least 90%, at least 95%, at least 98% identical or 100% identical to the nucleotide sequence of SEQ ID NO:1 for use in the treatment of choroideremia is provided.

In other related aspects, the use of a nucleic acid comprising a nucleotide sequence at least 90%, at least 95%, at least 98% identical or 100% identical to the nucleotide sequence of SEQ ID NO:1 for the manufacture of a medicament is provided.

In other related aspects, the use of a nucleic acid comprising a nucleotide sequence at least 90%, at least 95%, at least 98% identical or 100% identical to the nucleotide sequence of SEQ ID NO:1 for the manufacture of a medicament for the treatment of choroideremia is provided.

In some aspects, the nucleotide sequence at least 90%, at least 95%, at least 98% identical or 100% identical to the nucleotide sequence of SEQ ID NO:1 is operably linked to an expression control sequence. In some embodiments, the nucleotide sequence of SEQ ID NO:1 is operably linked to a CAG promoter. In some preferred embodiments, the CAG promoter has the sequence of SEQ ID NO:4.

In some embodiments, the nucleotide sequence at least 90%, at least 95%, at least 98% identical or 100% identical to the nucleotide sequence of SEQ ID NO:1 forms part of an expression cassette. In some aspects, the expression cassette comprises from 5' to 3': (a) an AAV2 terminal repeat (b) a CAG promoter (c) codon optimized REP1 gene of SEQ ID NO:1 (d) an SV40 polyadenylation sequence and (e) an AAV2 terminal repeat. In preferred embodiments, the 5' AAV2 terminal repeat has the nucleotide sequence set forth as SEQ ID NO:6 and/or the CAG promoter has the nucleotide sequence set forth as SEQ ID NO:4 and/or the SV40 polyadenylation sequence has the nucleotide sequence set forth as SEQ ID NO:8 and/or the 3' AAV2 terminal repeat has the nucleotide sequence set forth as SEQ ID NO:7. In a particularly preferred embodiment, the expression cassette comprises a nucleic acid comprising the nucleotide sequence of SEQ ID NO:5 or a sequence at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identical thereto.

In further embodiments, a method is provided for the treatment of choroideremia in a subject in need of such treatment by administering to the subject a therapeutically effective amount of a recombinant AAV (rAAV) virion, or a pharmaceutical composition comprising same, the rAAV virion comprising (i) a nucleic acid having a nucleotide sequence at least 90%, at least 95%, at least 98% identical or 100% identical to the nucleotide sequence of SEQ ID NO:1 operably linked to an expression control sequence and (ii) an AAV capsid.

In related embodiments, provided is the use of a recombinant AAV (rAAV) virion comprising (i) a nucleic acid having a nucleotide sequence at least 90%, at least 95%, at least 98% identical or 100% identical to the nucleotide sequence of SEQ ID NO:1 operably linked to an expression control sequence and (ii) an AAV capsid for the treatment of choroideremia.

In other related embodiments, provided is the use of a recombinant AAV (rAAV) virion comprising (i) a nucleic acid having a nucleotide sequence at least 90%, at least 95%, at least 98% identical or 100% identical to the nucleotide sequence of SEQ ID NO:1 operably linked to an expression control sequence and (ii) an AAV capsid for the manufacture of a medicament for the treatment of choroideremia.

In some embodiments, the rAAV virion comprises a native AAV2, AAV4, AAV5 or AAV8 capsid. In other embodiments, the rAAV virion comprises a variant AAV capsid that comprises one or more modifications relative to AAV2, AAV4, AAV5 or AAV8. In a preferred embodiment, the AAV capsid comprises the sequence of SEQ ID NO:9.

In some embodiments, the rAAV virion comprises (i) a native AAV2 capsid or variant thereof and (ii) an expression cassette comprising from 5' to 3': (a) an AAV2 terminal repeat (b) a CAG promoter (c) codon optimized REP1 gene of SEQ ID NO:1 (d) an SV40 polyadenylation sequence and (e) an AAV2 terminal repeat. In preferred embodiments, the rAAV comprises (i) a capsid comprising a capsid protein of SEQ ID NO:9 and (ii) a nucleic acid comprising a 5' AAV2 terminal repeat of SEQ ID NO:6, a CAG promoter of SEQ ID NO:4, an SV40 polyadenylation sequence of SEQ ID NO:8 and a 3' AAV2 terminal repeat of SEQ ID NO:7. In a particularly preferred embodiment, the rAAV comprises (i) a capsid comprising a capsid protein of SEQ ID NO:9 and (ii) an expression cassette comprising the nucleotide sequence of SEQ ID NO:5.

In particularly preferred embodiments, the use of an rAAV in the treatment of choroideremia or for the manufacture of a medicament for the treatment of choroideremia is provided, wherein the rAAV comprises (i) a nucleic acid comprising a nucleotide sequence of SEQ ID NO:5 and (ii) a capsid comprising a capsid protein having the amino acid sequence of SEQ ID NO:9. In some aspects, the rAAV is administered by intravitreal injection.

In other particularly preferred embodiments, a method for the treatment of choroideremia is provided comprising administering to the subject an effective amount of an rAAV comprising (i) a nucleic acid comprising a nucleotide sequence of SEQ ID NO:5 and (ii) a capsid comprising a capsid protein having the amino acid sequence of SEQ ID NO:9. In some aspects, the rAAV is administered to the subject by intravitreal injection.

In other aspects, a pharmaceutical composition is provided comprising a nucleic acid having a nucleotide sequence at least 90%, at least 95% at least 98% identical or 100% identical to the nucleotide sequence of SEQ ID NO:1, optionally operably linked to an expression control sequence, and at least one pharmaceutically acceptable excipient.

In some embodiments, the pharmaceutical composition comprises a nucleic acid comprising the nucleotide sequence of SEQ ID NO:1 operably linked to a constitutive promoter, preferably a CAG promoter having a sequence at least 90%, at least 95% at least 98% identical or 100% identical to the nucleotide sequence of SEQ ID NO:4.

In other aspects, a pharmaceutical composition is provided comprising at least one pharmaceutically acceptable excipient and an infectious rAAV comprising (i) an AAV capsid and (ii) a nucleic acid comprising from 5' to 3': (a) an AAV2 terminal repeat (b) a CAG promoter (c) codon optimized REP1 gene of SEQ ID NO:1 (d) an SV40 polyadenylation sequence and (e) an AAV2 terminal repeat. In related embodiments, the pharmaceutical composition comprises between $10^9$ vg and $10^{14}$ vg, preferably between $10^{10}$ vg and $10^{13}$ vg of the rAAV, more preferably comprises about $3\times10^{11}$ vg or about $1\times10^{12}$ vg of the rAAV.

In preferred embodiments, the pharmaceutical composition comprises an rAAV comprising (i) a capsid comprising a capsid protein comprising or consisting of the sequence of SEQ ID NO:9 and (ii) a nucleic acid comprising codon optimized REP1 gene of SEQ ID NO:1, wherein the nucleic acid further comprises a 5' AAV2 terminal repeat of SEQ ID NO:6 and/or a CAG promoter of SEQ ID NO:4 and/or an SV40 polyadenylation sequence of SEQ ID NO:8 and/or an AAV2 terminal repeat of SEQ ID NO:7. In related embodiments, the pharmaceutical composition comprises between $10^9$ vg and $10^{14}$ vg, preferably between $10^{10}$ vg and $10^{11}$ vg of the rAAV, more preferably comprises about $3\times10^{11}$ vg or about $1\times10^{12}$ vg of the rAAV.

In some embodiments, a method for expressing REP1 in one or more retinal pigmented epithelial cells and one or more rod photoreceptor cells of a human subject is provided comprising administering to the human subject an effective amount of an infectious rAAV as herein described, wherein the REP1 is expressed in the one or more retinal pigmented epithelial cells and one or more rod photoreceptor cells. In some preferred embodiments, the effective amount of infectious rAAV is $10^9$ vg/eye to $10^{14}$ vg/eye and/or a single dose of the rAAV is intravitreally administered (bilaterally or unilaterally) to the human subject and/or the rAAV comprises a capsid of SEQ ID NO:9 and/or the rAAV comprises a heterologous nucleic acid comprising the nucleotide sequence of SEQ ID NO:5.

In a particularly preferred embodiment, a pharmaceutical composition is provided comprising at least one pharmaceutically acceptable excipient and an infectious rAAV comprising (i) a capsid comprising a capsid protein comprising or consisting of the sequence of SEQ ID NO:9 and (ii) a nucleic acid comprising or consisting of the nucleotide sequence of SEQ ID NO:5. In related embodiments, the pharmaceutical composition comprises $10^9$ vg and $10^{14}$ vg, preferably between $10^{10}$ vg and $10^{13}$ vg of the rAAV, more preferably comprises about $3\times10^{11}$ vg or about $1\times10^{12}$ vg of the rAAV.

In some embodiments, a nucleic acid or infectious rAAV as herein described is administered by periocular or intraocular (intravitreal, suprachoroidal or subretinal) injection to a human with choroideremia, whereby the choroideremia is treated in the subject. In other embodiments, a nucleic acid or infectious rAAV as herein described is administered subretinally or intravitreally to a human with choroideremia, whereby the choroideremia is treated in the subject. In preferred embodiments, a human subject with choroideremia is administered a single intravitreal injection (bilateral or unilateral) of an rAAV as herein described.

In related aspects, treatment of choroideremia in a treated subject comprises (i) an improvement (i.e. gain) in visual function or functional vision relative to a control (e.g. relative to a baseline measurement in the treated patient prior to treatment, relative to the untreated eye if the nucleic acid or rAAV is administered unilaterally, or relative to an untreated concurrent or historical control group of choroideremia patients) and/or (ii) a decrease in loss of visual function and/or retinal degeneration in a treated eye compared to a control (e.g. untreated eye in same patient or untreated control group) at e.g. 6 months, 12 months or 24 months after treatment. These improvements can be assessed by an appropriate ophthalmological test, including but not limited to visual acuity testing, microperimetry and other visual field testing, anatomical testing, such as optical coherence tomography scans and fundus autofluorescence imaging, retinal electrophysiology, and/or quality of life (QoL) assessments.

In some aspects, an effective amount of a nucleic acid or rAAV (or pharmaceutical composition comprising same) as herein described is an amount effective to treat choroideremia in a human patient. In related aspects, an effective amount of an rAAV as herein described is between $10^9$ and $10^{14}$ rAAV particles (or vector genomes (vg))/eye), preferably between $10^{10}$ and $10^{13}$ vg/eye, or between $1\times10^{11}$ vg/eye and $5\times10^{12}$ vg/eye, more preferably is about $3\times10^{11}$ vg/eye or about $1\times10^{12}$ vg/eye. In some preferred embodiments, a single dose of about $3\times10^{11}$ vg/eye or about $1\times10^{12}$ vg/eye is intravitreally administered to a human patient with choroideremia, whereby the choroideremia is treated.

Some embodiments of the invention are exemplified in the following items 1 to 41:

1. A nucleic acid encoding human Rab escort protein-1 (REP1) protein of SEQ ID NO:2 and codon optimized for expression in humans, the nucleic acid comprising the nucleotide sequence set forth as SEQ ID NO: 1 or comprising a nucleotide sequence at least 95% identical thereto, wherein the nucleic acid is expressed at a greater level compared with the level of expression of the wild type REP1 nucleotide sequence of SEQ ID NO: 3 in an otherwise identical cell.

2. The nucleic acid according to item 1, wherein the nucleotide sequence has a codon adaptation index of at least 0.94.

3. The nucleic acid according to item 1, comprising the nucleotide sequence set forth as SEQ ID NO: 1.

4. An expression cassette comprising the nucleic acid according to any one of items 1 to 3 and an expression control sequence operably linked and heterologous to the nucleic acid sequence.

5. The expression cassette of item 4, wherein the expression control sequence is a constitutive promoter, preferably a CAG promoter comprising the nucleotide sequence set forth as SEQ ID NO:4 or a sequence at least 90%, at least 95%, or at least 98% identical thereto.

6. The expression cassette of item 5, comprising from 5' to 3': (a) an AAV2 terminal repeat (b) a CAG promoter (c) codon optimized REP1 gene of SEQ ID NO:1 (d) an SV40 polyadenylation sequence and (e) an AAV2 terminal repeat.

7. The expression cassette of item 6, wherein the 5' AAV2 terminal repeat has the nucleotide sequence set forth as SEQ ID NO:6 and/or wherein the CAG promoter has the nucleotide sequence set forth as SEQ ID NO:4 and/or wherein the SV40 polyadenylation sequence has the nucleotide sequence set forth as SEQ ID NO:8 and/or wherein the 3' AAV2 terminal repeat has the nucleotide sequence set forth as SEQ ID NO:7.

8. The expression cassette of item 7, comprising or consisting of the nucleotide sequence of SEQ ID NO:5 or a sequence at least 90%, at least 95%, at least 98% identical thereto.

9. The expression cassette of item 3, wherein the expression control sequence is a promoter that directs preferential expression of the nucleic acid in rods and cones.

10. A vector comprising the nucleic acid according to any one of items 1 to 3 or an expression cassette according to any one of items 4 to 9.

11. The vector of item 10, wherein the vector is a recombinant adeno-associated (rAAV) vector.

12. The vector of item 11, wherein the rAAV vector comprises an AAV capsid of serotype 2, 4, 5 or 8 or a variant thereof.

13. The vector of item 12, wherein the rAAV vector comprises an AAV2 capsid or variant thereof.

14. The vector of item 13, wherein the rAAV vector comprises an AAV2 capsid variant comprising a capsid protein comprising or consisting of the sequence of SEQ ID NO:9.

15. The vector of any one of items 11-14, wherein the rAAV vector comprises a nucleic acid comprising from 5' to 3': (a) an AAV2 terminal repeat (b) a CAG promoter (c) codon optimized REP1 gene of SEQ ID NO:1 (d) an SV40 polyadenylation sequence and (e) an AAV2 terminal repeat.

16. The vector of item 15, wherein the 5' AAV2 terminal repeat has the nucleotide sequence set forth as SEQ ID NO:6 and/or wherein the CAG promoter has the nucleotide sequence set forth as SEQ ID NO:4 and/or wherein the SV40 polyadenylation sequence has the nucleotide sequence set forth as SEQ ID NO:8 and/or wherein the 3' AAV2 terminal repeat has the nucleotide sequence set forth as SEQ ID NO:7.

17. The vector of item 16, wherein the rAAV comprises a nucleic acid comprising the nucleotide sequence of SEQ ID NO:5 or a sequence at least 90%, at least 95% or at least 98% identical thereto.

18. The vector of item 17, wherein the rAAV comprises (i) a capsid comprising a capsid protein comprising or consisting of the sequence of SEQ ID NO:9 and (ii) a nucleic acid comprising or consisting of the nucleotide sequence of SEQ ID NO:5.

19. A host cell comprising the nucleic acid according to any one of items 1 to 3 or an expression cassette according to any one of items 4 to 9.

20. The host cell according to item 19, wherein the host cell is a mammalian cell.

21. The host cell of item 19 or 20, wherein the host cell is a CHO cell, an HEK293 cell, an HEK293T cell, a HeLa cell, a BHK21 cell or a Vero cell and/or wherein the host cell is grown in a suspension or cell stack culture and/or wherein the host cell is a photoreceptor cell, a retinal ganglion cell, a glial cell, a bipolar cell, an amacrine cell, a horizontal cell, or a retinal pigmented epithelium cell.

22. A method for treating choroideremia in a subject in need thereof, comprising administering to the subject a therapeutically effective amount of a nucleic acid according to any one of items 1-3, an expression cassette according to any one of items 4-9 or a vector according to any one of items 10-18.

23. A method for treating choroideremia in a subject in need thereof, comprising administering to the subject an infectious rAAV comprising (i) an AAV capsid and (ii) a nucleic acid comprising from 5' to 3': (a) an AAV2 terminal repeat (b) a CAG promoter (c) codon optimized REP1 gene of SEQ ID NO:1 (d) an SV40 polyadenylation sequence and (e) an AAV2 terminal repeat.

24. The method according to item 23, wherein the 5' AAV2 terminal repeat has the nucleotide sequence set forth as SEQ ID NO:6 and/or wherein the CAG promoter has the nucleotide sequence set forth as SEQ ID NO:4 and/or wherein the SV40 polyadenylation sequence has the nucleotide sequence set forth as SEQ ID NO:8 and/or wherein the 3' AAV2 terminal repeat has the nucleotide sequence set forth as SEQ ID NO:7.

25. The method according to item 23 or 24, wherein the rAAV comprises (i) a capsid comprising a capsid protein comprising or consisting of the sequence of SEQ ID NO:9 and (ii) a nucleic acid comprising or consisting of the nucleotide sequence of SEQ ID NO:5.

26. The method according to any one of items 22-25, wherein the nucleic acid or vector is administered to the subject by intravitreal or subretinal injection and/or wherein the vector is administered to the subject at a dosage from about $10^{10}$ vector genomes (vg)/eye to about $10^{13}$ vg/eye, preferably from about $1\times10^{11}$ vg/eye to about $5\times10^{12}$ vg/eye, more preferably at a dosage of about $3\times10^{11}$ vg/eye or at a dosage of about $1\times10^{12}$ vg/eye.

27. A nucleic acid according to any one of items 1-3, an expression cassette according to any one of items 4-9, or a vector according to any one of items 10-18 for use in the treatment of choroideremia.

28. A nucleic acid according to any one of items 1-3, an expression cassette according to any one of items 4-9, or a vector according to any one of items 10-18 for use in the manufacture of a medicament for the treatment of choroideremia.

29. The nucleic acid, expression cassette or vector for use according to item 27 or 28, wherein the nucleic acid or vector is administered by intravitreal or subretinal injection and/or wherein the vector is for administration at a dosage from about $10^{10}$ vector genomes (vg)/eye to about $10^{13}$ vg/eye, preferably from about $1\times10^{11}$ vg/eye to about $5\times10^{12}$ vg/eye, more preferably is for administration at a dosage of about $3\times10^{11}$ vg/eye or at a dosage of about $1\times10^{12}$ vg/eye.

30. An infectious rAAV comprising (i) an AAV capsid and (ii) a nucleic acid comprising from 5' to 3': (a) an AAV2 terminal repeat (b) a CAG promoter (c) codon optimized REP1 gene of SEQ ID NO:1 (d) an SV40 polyadenylation sequence and (e) an AAV2 terminal repeat, for use in the treatment of choroideremia.

31. An infectious rAAV comprising (i) an AAV capsid and (ii) a nucleic acid comprising from 5' to 3': (a) an AAV2 terminal repeat (b) a CAG promoter (c) codon optimized REP1 gene of SEQ ID NO:1 (d) an SV40 polyadenylation sequence and (e) an AAV2 terminal repeat, for use in the manufacture of a medicament for the treatment of choroideremia.

32 The infectious rAAV according to item 30 or 31, wherein the 5' AAV2 terminal repeat has the nucleotide sequence set forth as SEQ ID NO:6 and/or wherein the CAG promoter has the nucleotide sequence set forth as SEQ ID NO:4 and/or wherein the SV40 polyadenylation sequence has the nucleotide sequence set forth as SEQ ID NO:8 and/or wherein the 3' AAV2 terminal repeat has the nucleotide sequence set forth as SEQ ID NO:7.

33. The infectious rAAV according to item 32, wherein the rAAV comprises (i) a capsid comprising a capsid protein comprising or consisting of the sequence of SEQ ID NO:9 and (ii) a nucleic acid comprising or consisting of the nucleotide sequence of SEQ ID NO:5.

34. The infectious rAAV for use according to any one of items 30-33, wherein the rAAV is administered by intravitreal injection and/or wherein the vector is administered at a dosage from about $10^{10}$ vector genomes (vg)/eye to about $10^{13}$ vg/eye, preferably from about $1\times10^{11}$ vg/eye to about $5\times10^{12}$ vg/eye, more preferably is administered at a dosage of about $3\times10^{11}$ vg/eye or at a dosage of about $1\times10^{12}$ vg/eye.

35. A method for treating a disease or condition mediated by a decreased level of REP1 in a mammal, the method comprising administering a therapeutically effective amount of a nucleic acid according to any one of items 1-3, an expression cassette according to any one of items 4-9, or a vector according to any one of items 10-18.

36. A method for increasing the level of REP1 in a mammal, the method comprising administering to the mammal a nucleic acid according to any one of items 1-3, an expression cassette according to any one of items 4-9, or a vector according to any one of items 10-18.

37. A pharmaceutical composition comprising a nucleic acid according to any one of items 1-3, an expression cassette according to any one of items 4-9, or a vector according to any one of items 10-18, and at least one pharmaceutically acceptable excipient.

38. A pharmaceutical composition comprising an infectious rAAV comprising (i) an AAV capsid and (ii) a nucleic acid comprising from 5' to 3': (a) an AAV2 terminal repeat (b) a CAG promoter (c) codon optimized REP1 gene of SEQ ID NO:1 (d) an SV40 polyadenylation sequence and (e) an AAV2 terminal repeat.

39. The pharmaceutical composition according to item 38, wherein the 5' AAV2 terminal repeat has the nucleotide sequence set forth as SEQ ID NO:6 and/or wherein the CAG promoter has the nucleotide sequence set forth as SEQ ID NO:4 and/or wherein the SV40 polyadenylation sequence has the nucleotide sequence set forth as SEQ ID NO:8 and/or wherein the 3' AAV2 terminal repeat has the nucleotide sequence set forth as SEQ ID NO:7.

40. The pharmaceutical composition according to item 39, wherein the rAAV comprises (i) a capsid comprising a capsid protein comprising or consisting of the sequence of SEQ ID NO:9 and (ii) a nucleic acid comprising or consisting of the nucleotide sequence of SEQ ID NO:5.

41. The pharmaceutical composition according to any one of items 38-40, wherein the pharmaceutical composition comprises between $10^9$ vg and $10^{14}$ vg of the rAAV, preferably between $10^{10}$ vg and $10^{13}$ vg of the rAAV, more preferably comprises about $3 \times 10^{11}$ vg or about $1 \times 10^{12}$ vg of the rAAV.

EXAMPLES

The following examples illustrate preferred embodiments of the present invention and are not intended to limit the scope of the invention in any way. While this invention has been described in relation to its preferred embodiments, various modifications thereof will be apparent to one skilled in the art from reading this application.

Example 1—Odon Optimization of REP cDNA Sequence

The human REP1 open reading frame cDNA sequence (NCBI Reference Sequence NM_000390.4) was codon optimized for human expression. The optimization algorithm included parameters including, but not limited to, codon usage bias, GC content, CpG dinucleotides content, negative CpG islands, mRNA secondary structure, RNA instability motifs, cryptic splicing sites, premature polyadenylation sites, internal chi sites and ribosomal binding sites, and repeat sequences.

The native human REP1 gene employs tandem rare codons that can reduce the efficiency of translation or even disengage the translational machinery. The codon usage bias in humans was changed by upgrading the codon adaptation index (CAI) from 0.70 to 0.94. The average GC content was optimized from 54.24 in the native sequence to 61.22 in the optimized sequence to prolong the half-life of the mRNA. Stem-Loop structures, which impact ribosomal binding and stability of mRNA, were broken in the optimized sequence. In addition, negative cis-acting sites such as ATTTA (6 of which are deleted in the optimized sequence) were screened and deleted to optimize expression of the gene in human cells and several restriction enzyme sites were deleted (2 BglII(AGATCT), 1 EcoRI(GAATTC), 1 XhoI(CTCGAG) and 1 ARE sites were deleted).

The resulting codon optimized nucleotide sequence, set forth herein as SEQ ID NO:1, contains improved codon usage, altered GC content, better mRNA stability, and modification of negative cis acting elements relative to the native sequence of SEQ ID NO:3.

Example 2—(Odon Ontimized REP1 eDNA Seauegce is Expressed at Higher Levels in RPE Cell. From Patients with Choroideremia A human in vitro model system was generated to evaluate expression of codon optimized human REP1 nucleic acid having the nucleotide sequence of SEQ ID NO:1 in diseased human RPE cells derived from human choroideremia patients and functional correction of the CHM disease phenotype. This model system was chosen for in vitro pharmacology because a suitable non-human primate model of choroideremia (CHM) is lacking for pre-clinical studies. Two CHM patient fibroblast samples were reprogrammed to iPSCs, then differentiated into functional mature RPE cells. Lack of Rep1 protein in CHM patients has been shown to correlate with cellular defects in Rab27a trafficking and prenylation (see e.g. Strunnikova, N. V. et al., PLoS Biol. 4, e8402 (2009); Sergeev, Y. V. et al., Mutat. Res.-Fundam. Mol. Mech. Mutagen, 665, 44-50 (2009); Rak, A. et al., Cell 117, 749-760 (2004)).

Materials and Methods
Generation of Induced Pluripotent Stem Cell Lines from Choroideremia Patient Cells Cellular reprogramming of fibroblasts from two choroideremia patients (referred to herein as CHM1 and CHM2), was performed by Simplicon RNA reprogramming (EMD Millipore). At day 10, approximately $5 \times 10^4$-$1 \times 10^5$ reprogrammed cells were re-plated on growth factor reduced Matrigel (Corning) in mouse embryonic fibroblasts (MEF)-conditioned medium containing B18R protein (200 ng/mL) supplemented with human iPSC Reprogramming Boost Supplement II (EMD Millipore). At day 20, reprogrammed cells, recognized by altered morphology and ability to form small colonies, were transitioned to mTeSR-1 media (Stem Cell Technologies). Colonies of approximately 200 cells or larger were isolated manually and plated on growth factor reduced Matrigel coated plates in mTeSR-1 medium. CHM-iPSC lines were expanded from a single colony. The CHM-iPSC lines were cultured on Vitronectin XF (Stem Cell Technologies) in mTeSR-1 maintenance medium and subcultured using Gentle Cell Dissociation Reagent (Stem Cell Technologies), every 4-5 days at 70-80% confluence. To ensure random differentiation into all three germ layers, iPSC embryoid bodies (EBs) were formed in suspension culture for one week and then differentiated in adherent conditions for an additional four weeks in mTeSR-1 basal medium, plus 20% Knockout Serum Replacement (Thermo Fisher Scientific).

Generation of Human Choroideremia Retinal Pigmented Epithelial (RPE) Cells

RPE cells were generated by a directed differentiation protocol as previously described (Leach et al., *Investigative*

*ophthalmology & visual science* 56(2):1002-13 (2015)). Briefly, iPSCs were passaged directly onto Matrigel (BD Biosciences) in DMEM/F12 with 1×B27, 1×N2, and 1×NEAA (Invitrogen). From days 0 to 2, 50 ng/ml Noggin, 10 ng/ml Dkk1, 10 ng/ml IGF1 (R&D Systems Inc.), and 10 mM nicotinamide were added to the base medium. From days 2 to 4, 10 ng/ml Noggin, 10 ng/ml Dkk1, 10 ng/ml IGF1, and 5 ng/ml bFGF and 10 mM nicotinamide were added to the base medium. From days 4 to 6, 10 ng/ml Dkk1 and 10 ng/ml IGF1 and in 100 ng/ml Activin A (R&D Systems) were added to the base medium. From days 6 to 14, 100 ng/ml Activin A, 10 µM SU5402 (EMD Millipore), and 1 mM VIP (Sigma-Aldrich) were added to the base medium. At day 14, the cells were mechanically enriched by scraping away cells with non-RPE morphology. Subsequently, the remaining RPE were digested using TrypLE Express (Invitrogen) for ~5 minutes at 37° C. The cells were passed through a 30-µm single-cell strainer and seeded onto Matrigel-coated tissue culture plastic, transwell membranes (Corning Enterprises), or CC2-treated chambered slides in XVIVO-10 media (Lonza).

Functional Characterization of Human Choroideremia RPE Cells

CHM RPE cells were cultured using a formulated media to analyze rod outer segment (ROS) phagocytosis (Maminishkis, et al., *Investigative Ophthalmology and Visual Science*, 47(8):3612-24 (2006)). Cells were plated in quadruplicate at 1×10$^5$ cells per cm$^2$ on 0.1% gelatin-coated black-walled, clear bottom 96 well plates and cultured for 30 days. Photoreceptor ROSs were isolated from bovine eyes (Sierra for Medical Science) as previously described (Molday R S and Molday L L, *Journal of Cell Biology*, 105(6 Pt 1):2589-601 (1987)) and fluorescently labeled with fluorescein isothiocyanate (FITC) protein (Thermo Fisher Scientific). In some conditions, cultured cells were treated with 62.5 µg/ml αVβ5 integrin function-blocking antibody (Abcam) or IgG isotype control (Abcam) for 30 minutes at 37° C. Following the initial antibody incubation, cells were challenged with 1×10$^6$ FITC-ROSs per well for five hours at 37° C. and 5% CO2 (Buchholz et al., *STEM CELLS TRANSLATIONAL MEDICINE* 2(5):384-93 (2013)) (Rowland et al., *Journal of Tissue Engineering and Regenerative Medicine*, 7(8):642-53 (2013)). After ROS incubation, the wells were washed six times with PBS and 0.4% trypan blue was then added for 20 minutes to quench fluorescence from extracellular ROS. Each well was imaged using epifluorescent microscopy, and integrated pixel density of photomicrographs was determined with Image J software using a rolling pixel radius of 50 (National Institutes of Health).

Immunocytochemistry

Cells were fixed with 4% paraformaldehyde (PFA) (Santa Cruz Biotechnologies) for 15 minutes at 4° C. All antibody staining was done in a blocking solution of PBS with 0.2% Triton-X100 (Sigma-Aldrich), 2% bovine serum albumin (Calbiochem), and 5% goat serum (Thermo Fisher). Primary antibody incubations were done overnight at 4° C. Cells were then incubated with secondary antibodies for one hour at room temperature and then counterstained with DAPI (Sigma Aldrich) in PBS for five minutes at room temperature. Cells were imaged using a Zeiss Axio Observer.D1. Image processing was performed using Zeiss Zen 2 software and FIJI. A list of primary and secondary antibodies is provided below at Table 3:

TABLE 3

| Antibody | Host | Company-Catalog No. | Dilution |
|---|---|---|---|
| Primary Antibodies | | | |
| OCT4 | Mouse | Millipore-MAB4401 | 1:50 |
| Nanog | Rabbit | Abcam-ab21624 | 1:50 |
| SOX2 | Rabbit | Abcam-ab92494 | 1:50 |
| BEST1 | Rabbit | Abcam-ab14927 | 1:100 |
| TUJ-1 | Mouse | Promega-G7121 | 1:200 |
| HNF4-A | Rabbit | Santa Cruz-SC-8987 | 1:100 |
| ASMA | Mouse | Sigma Aldrich-A2547 | 1:500 |
| GFP | Chicken | Abcam-ab13970 | 1:200 |
| MITF | Mouse | Thermo Fisher-MA5-14146 | 1:100 |
| OTX2 | Mouse | R&D Systems-MAB1979 | 1:20 |
| RPE-65 | Rabbit | Sant Cruz-sc32896 | 1:10 |
| ZO-1 | Mouse | Thermo Fisher-33-9100 | 1:200 |
| Secondary Antibodies | | | |
| Alexa Fluor488 anti-rabbit | Goat | Invitrogen-A11078 | 1:250 |
| Alexa Fluor555 anti-rabbit | Goat | Invitrogen-A21428 | 1:250 |
| Alexa Fluor680 anti-rabbit | Goat | Invitrogen-A21109 | 1:250 |
| Alexa Fluor488 anti-mouse | Goat | Invitrogen-A11029 | 1:250 |
| Alexa Fluor555 anti-mouse | Goat | Invitrogen-A21422 | 1:250 |
| Alexa Fluor680 anti-mouse | Goat | Invitrogen-35518 | 1:250 |

SDS-PAGE and Western Blot

CHM RPE cell lysates were harvested using a standard RIPA Buffer (Thermo Fisher) with a Complete Protease Inhibitor Tablet (Millipore Sigma) and incubated on ice for 15 minutes. Samples were then centrifuged at 21×g for 15 minutes. Supernatants were collected, and protein concentrations were determined using a BCA protein assay (Thermo Fisher Scientific) normalized and adjusted to 2 µM DTT. Biorad 4× Sample Buffer was added and samples were heated at 70° C. for 10 minutes. An XT Criterion gel was run followed by gel transfer to a membrane. The membrane was then blocked and probed with REP1 and GADPH antibodies. Membranes were incubated with secondary antibodies conjugated to HRP and bands were visualized with ECL.

Prenylation Assay

The prenylation assay was performed using RPE cell lysates as described in Köhnke et al., *PLoS ONE* 8(12):1-11 (2013). Following a wash with PBS, cell lysates were prepared in cold Prenylation Buffer (500 µM HEPES pH 7.0, 50 µM NaCl, 2 µM MgCl2, 0.1 µM GDP, 0.5% NP-40, and a Complete Protease Inhibitor Tablet) and incubated on ice for 10-15 minutes. Protein concentrations were determined using a BCA protein assay (Thermo Fisher Scientific). Protein concentrations were normalized, and lysates adjusted to 2 µM DTT. Prenylation reactions were performed using 20 µL of lysate corresponding to 50-200 µg protein. The reaction for the functional complex was composed of 2 µM RabGGTase, 4 µM Rab27a and 4 µM BiotinGeranyl-PPi (Jena Bioscience). Reactions were incubated at 25° C. for 5 hours and stopped by adding 4× Sample Buffer (Biorad), DTT to 40 mM and heating at 70° C. for 10 minutes. Western blotting was carried out on XT Criterion gels according to manufacturer's protocols. Prenylation reactions were analyzed using streptavidin-HRP (Abcam).

Rab27A Trafficking Assay

RPE cells were seeded onto vitronectin coated eight chambered slides at 25,000 cells per cm$^2$ in XVIVO-10 media. Two days after seeding, the CHM RPE cells were transduced with recombinant AAV virions comprising (i) a transgene expression cassette having the sequence of SEQ ID NO:5 and (ii) a modified AAV2 capsid protein having the amino acid sequence of SEQ ID NO:9, at a multiplicity of infection (MOI) of 5000 vg/cell. Fourteen days post infection, cells were fixed and stained as described above.

Experimental Data

Figure 1B:
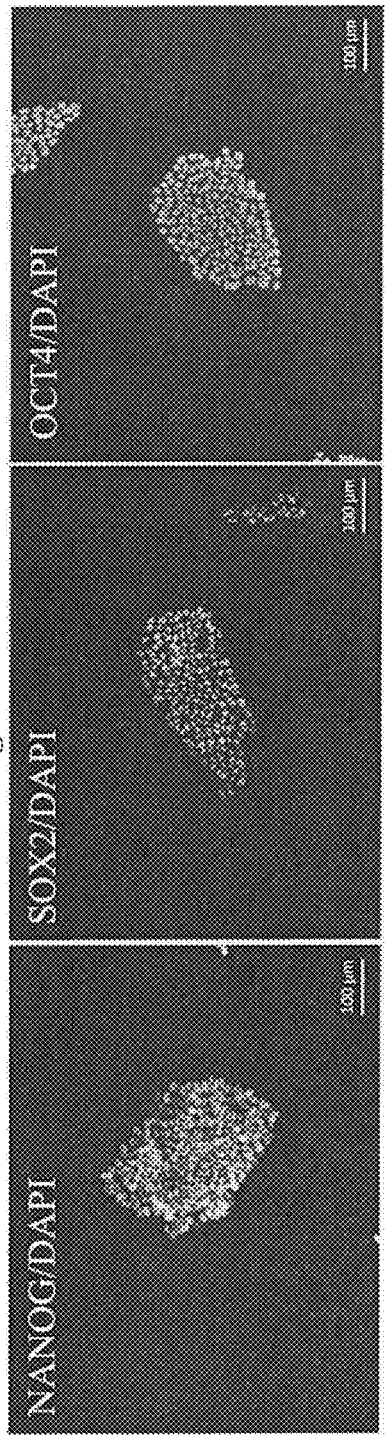
Figure 1C:
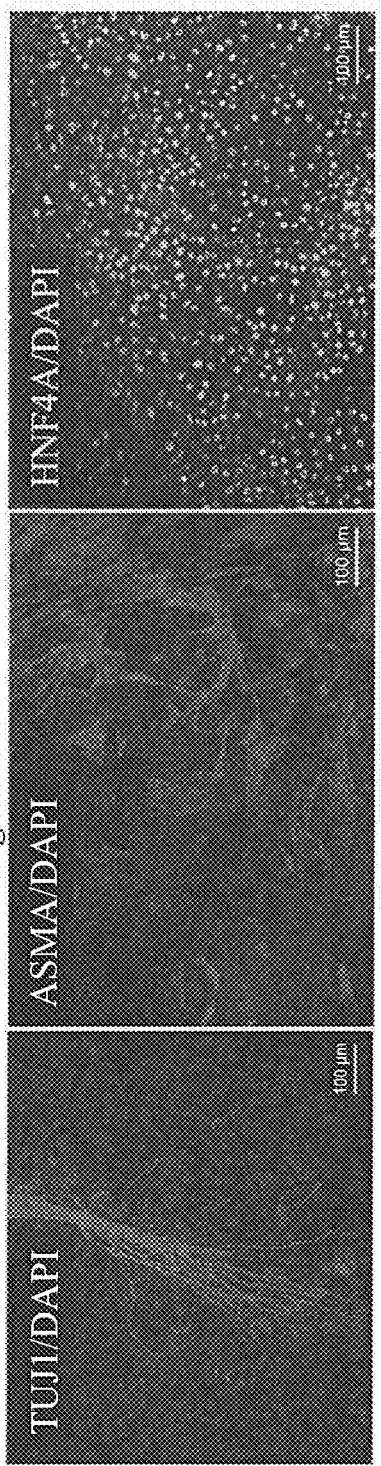
Figure 1D:
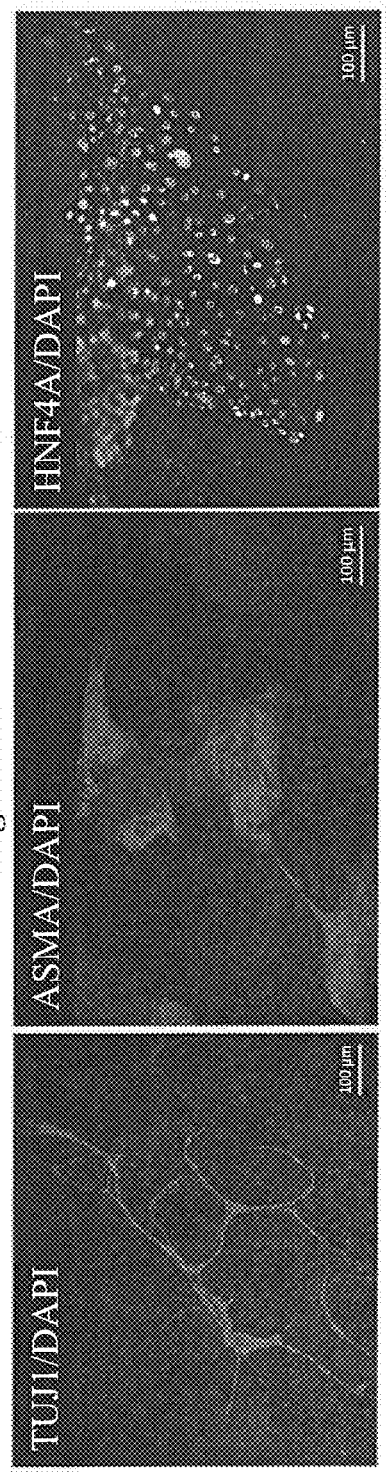
Figure 2A:
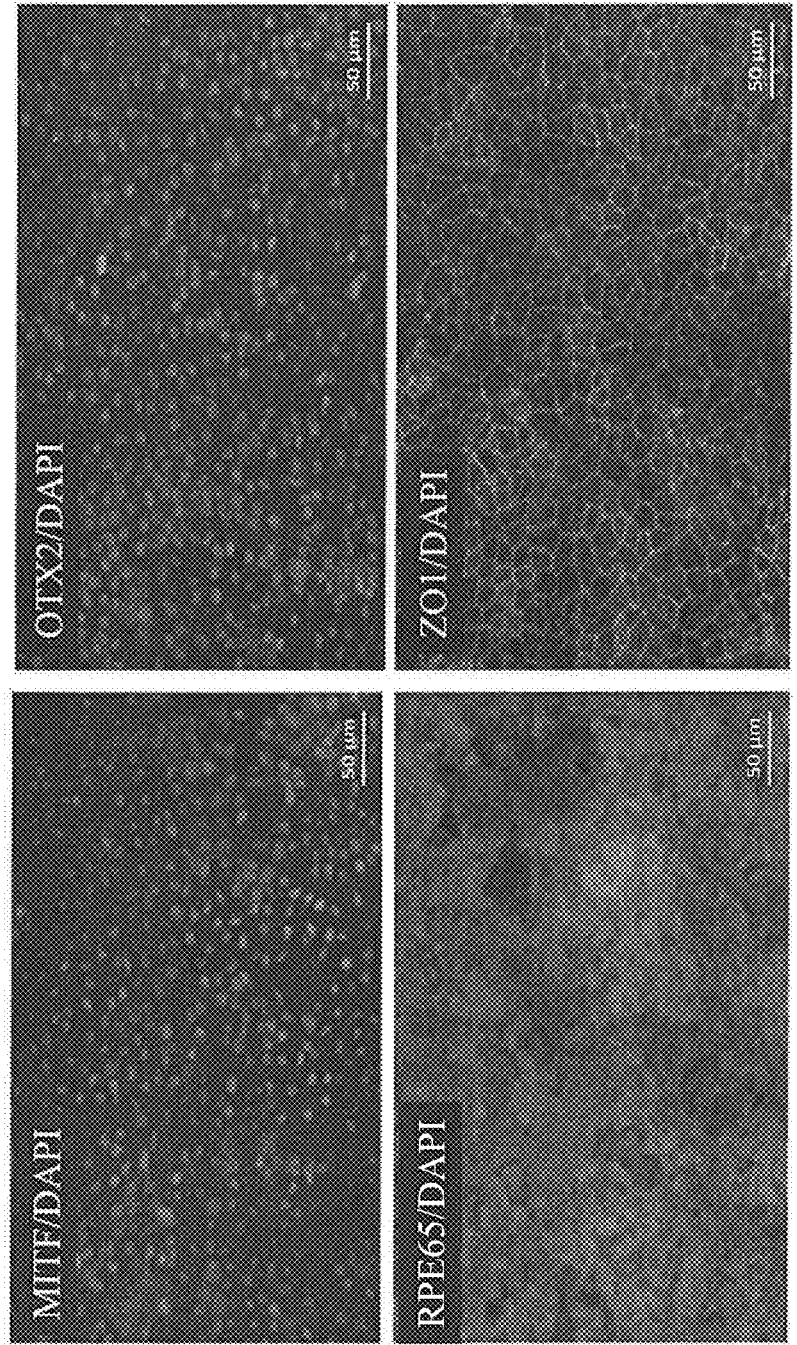
FIG. 2A-C FIGS. 2A and 2B illustrate immunocytochemical analysis of RPE cells derived from iPSCs derived from choroideremia patients CHM1 (FIG. 2A) and CHM2 (FIG. 2B). The RPE phenotype after 45 days of differentiation and maturation by ICC showed proper RPE transcriptional factor expression of Melanogenesis Associated Transcription Factor (MITF) and Orthodenticle Homeobox 2 (OTX2), expression of mature RPE cell marker RPE65, and expression of tight junction marker Zonula Occludens (ZO-1). The nuclei were counterstained with DAPI for CHM1 images. Scale bar=50 μm.
Figure 2B:
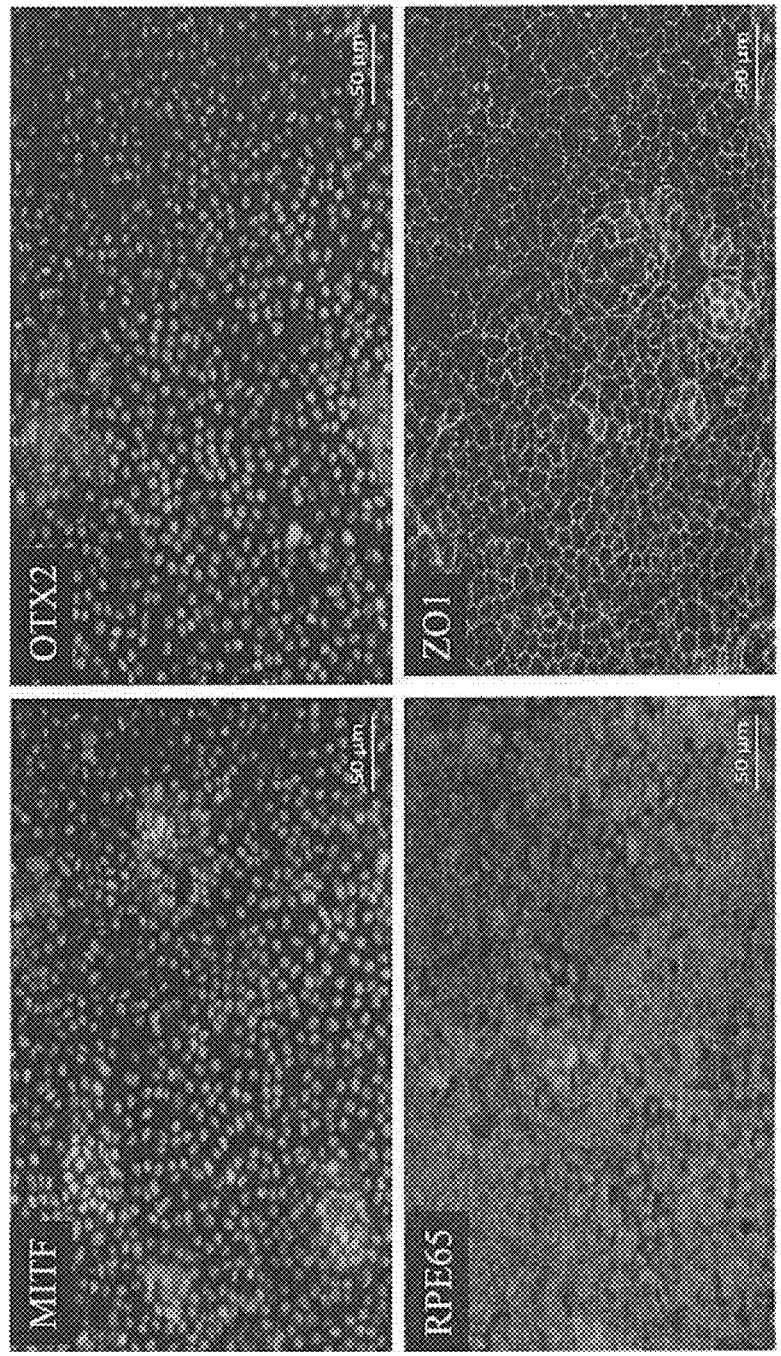
Figure 2C:
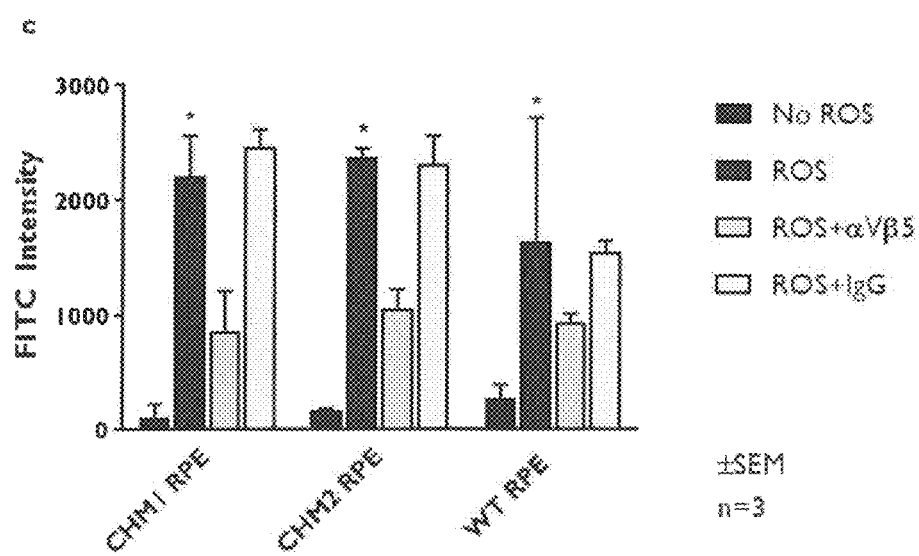

Two CHM patient fibroblast samples were obtained and reprogrammed to iPSCs followed by differentiation to RPE cells as described above. More specifically, cellular reprogramming of fibroblast cells (CHM1 and CHM2) was performed by Simplicon RNA reprogramming using synthetic in vitro transcribed RNA expressing four reprogramming factors (Oct4, Klf4, Sox2 and Glis1) in a polycistronic transcript that self-replicates for a limited number of cell divisions. Immunocytochemical analysis of human PSC markers NANOG, SOX2 and OCT4 was performed to confirm the pluripotency of both choroideremia iPSC lines, CHM1 and CHM2 (FIGS. 1a and 1b). To confirm pluripotency of the generated iPSC lines, cells were randomly differentiated in suspension culture as EBs and then differentiated in adherent conditions for four weeks and evaluated for the ability to differentiate into the ectodermal, mesodermal, and endodermal lineages. At that time, markers associated with neurons (TUJ1+), smooth muscle cells (ASMA+), and hepatocytes (HNF4A+) belonging to the ectoderm, mesoderm, and endoderm germ layers, respectively, were detected (FIGS. 1c and 1d). After confirmation of pluripotency, the iPSC lines generated from CHM1 and CHM2 patient cells were differentiated to RPE cells. RPE cells were allowed to mature for 30 days, followed by analysis for proper RPE cell marker expression and function. Protein expression and localization of Melanogenesis Associated Transcription Factor (MITF) and Orthodenticle Homeobox 2 (OTX2), RPE65 and zonula occludens (ZO-1) (FIGS. 2a and 2b) was normal. No changes in photoreceptor outer segment phagocytosis, a known function of RPE, (FIG. 2c) confirmed that CHM iPSC-derived RPE cells exhibit key physiological characteristics similar to those of native RPE.

Figure 3A:
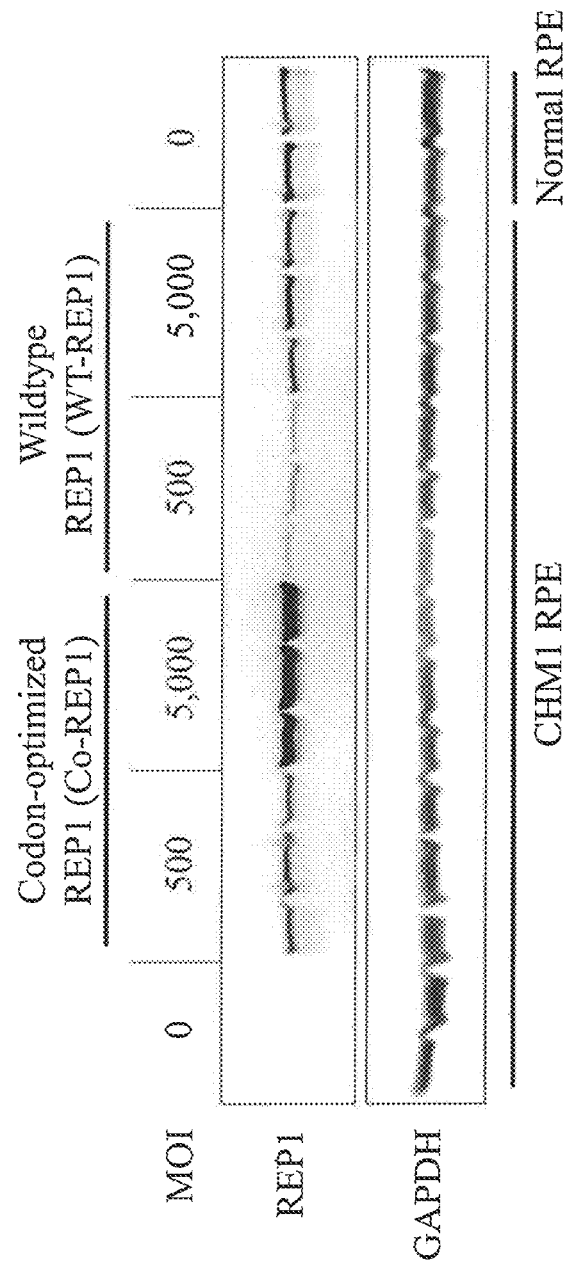

Expression levels of codon optimized REP1 transgene versus unmodified REP1 were assessed. To that end, recombinant AAV (rAAV) virions were isolated comprising (i) a modified AAV2 capsid protein having the amino acid sequence of SEQ ID NO:9 and (ii) a transgene expression cassette comprising either codon optimized REP1 of SEQ ID NO:1 or native REP1 of SEQ ID NO:3, each under the control of a CAG promoter of SEQ ID NO:4. Briefly, CHM RPE cells were transduced with the rAAV virions at two different MOIs, 500 or 5000 vg/cell. Cell lysates were collected 14 days post transduction and SDS-PAGE and Western blot analysis was carried out to evaluate REP1 expression levels. As illustrated in FIGS. 3A-B, codon optimized REP1 resulted in higher expression levels than unmodified REP1. Further, REP1 protein levels reached levels found in normal RPE at the lower dose (MOI 500 vg/cell).

Figure 4:
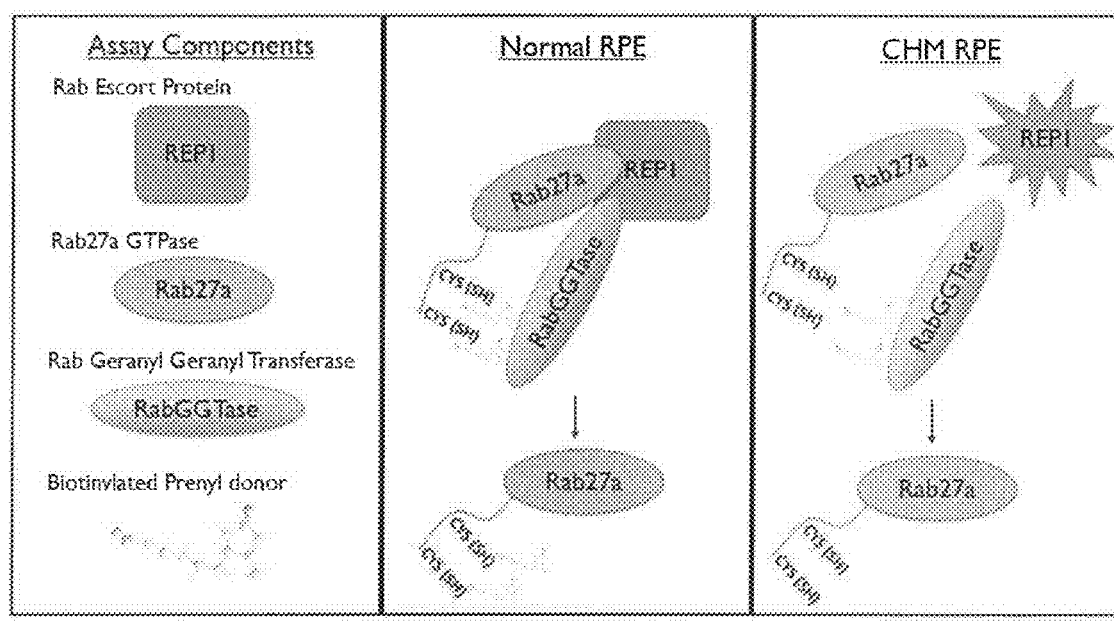
FIG. 4 Schematic illustration of the functional prenylation assay showing required components, including the biotinylated prenyl group serving as the readout of the biochemical assay. Normal RPE cells with functional REP1 protein successfully facilitate the prenylation of Rab27A GTPase, leading to the incorporation of the biotin groups. In CHM RPE, cells lack REP1 protein, causing accumulation of unprenylated Rab27a GTPase protein.
Figure 5A:
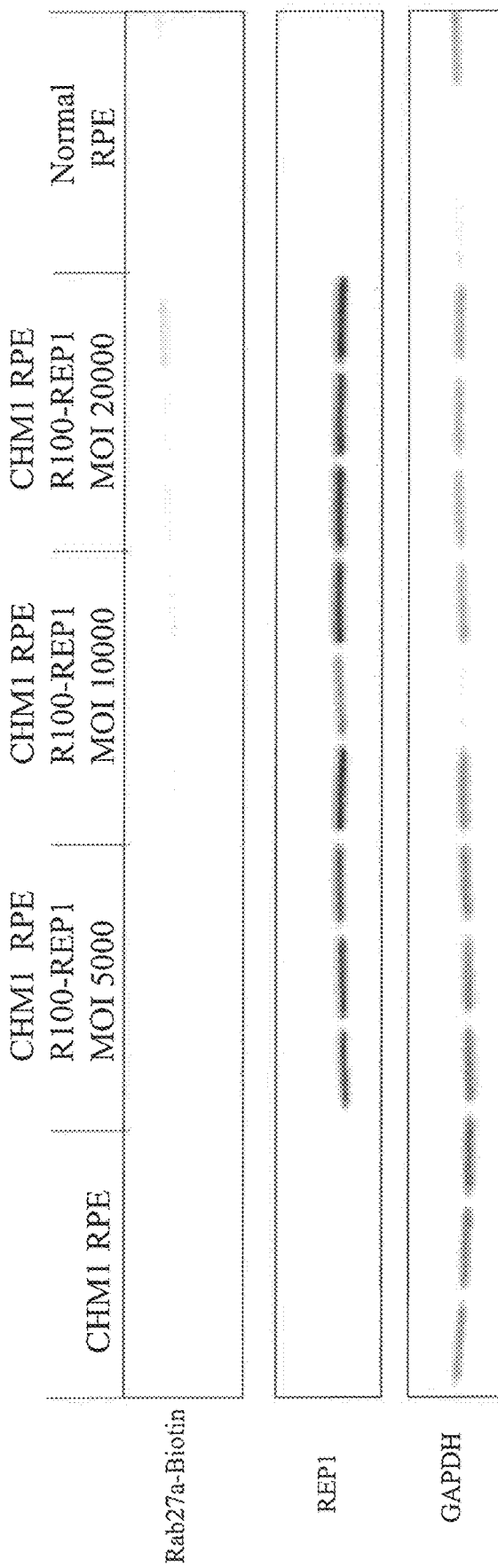
Figure 5B:
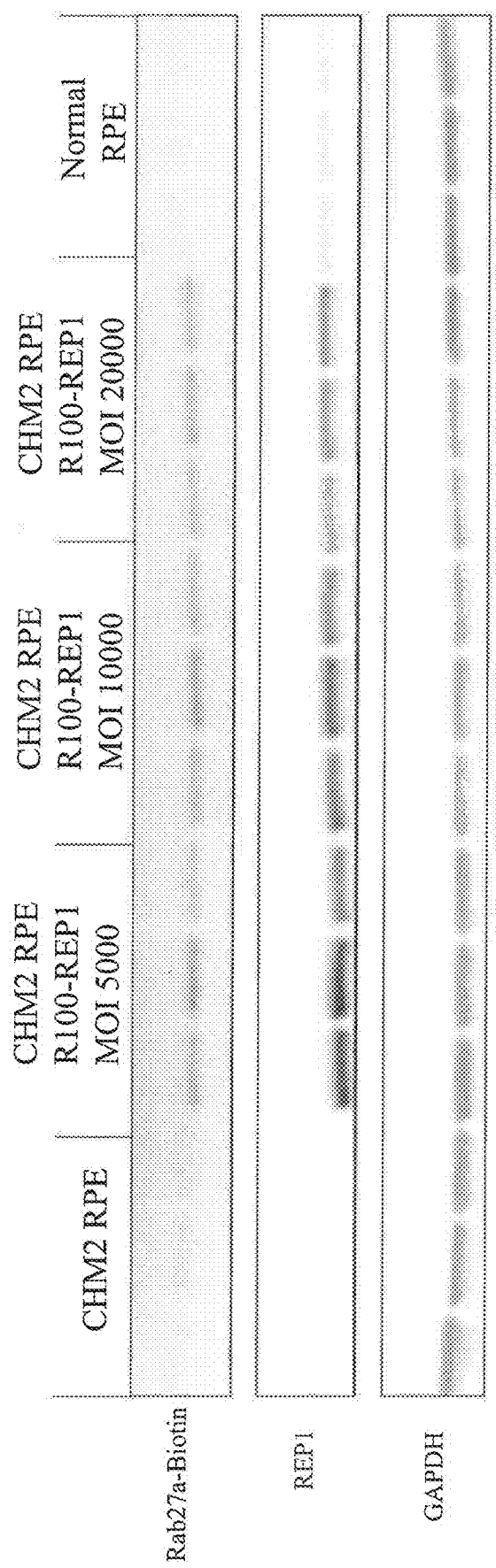
Figure 5C:
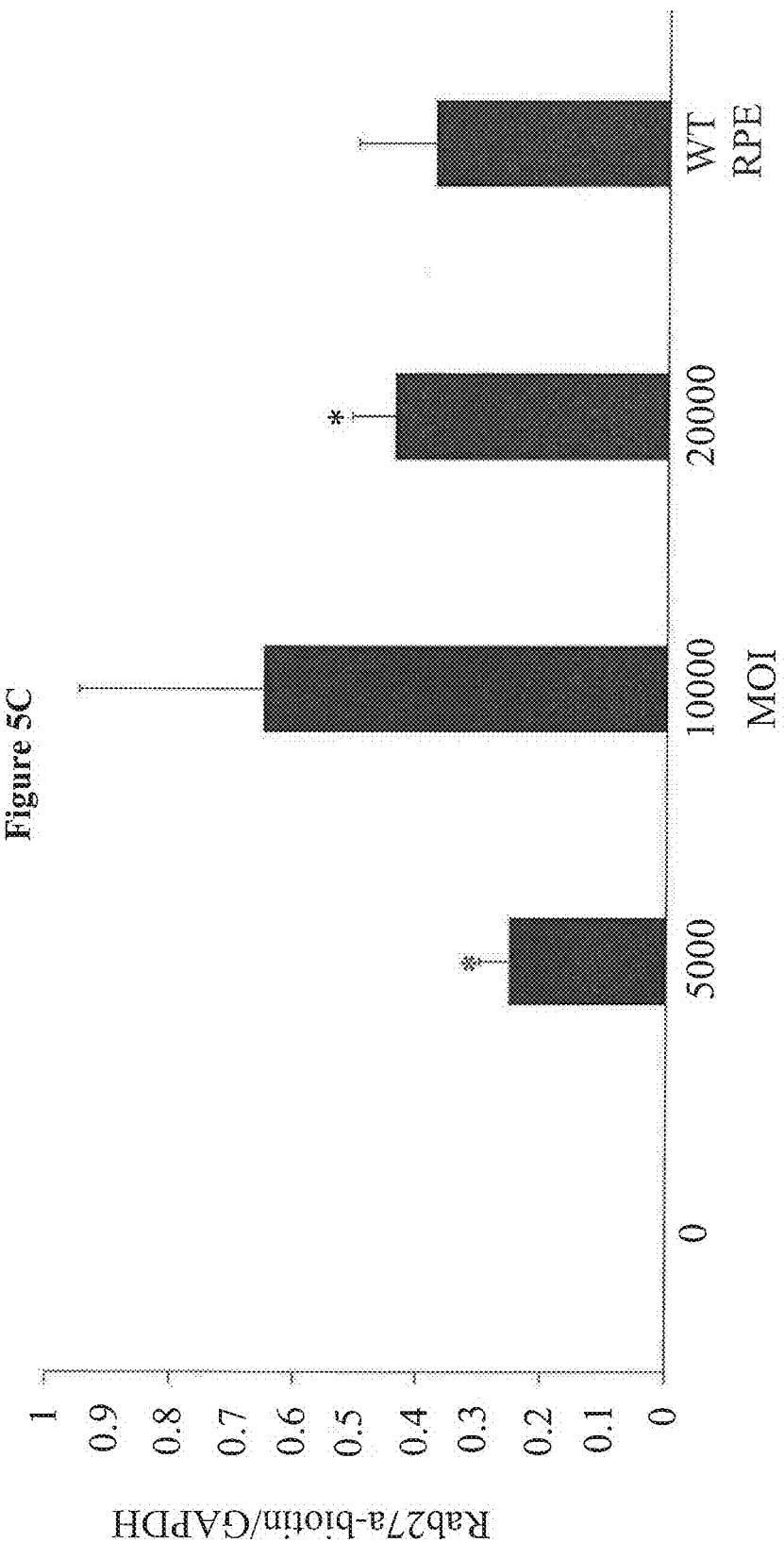
Figure 8:
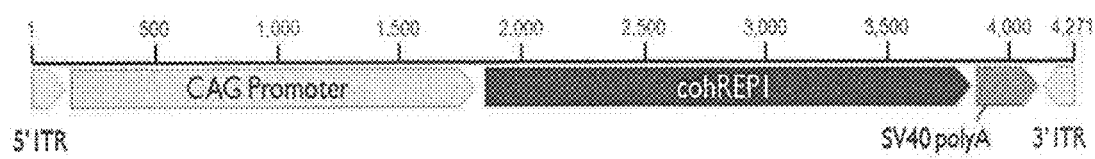
FIG. 8 is a schematic of the transgene cassette contained within the rAAV described in Example 2 below. The transgene cassette comprises a 5'AAV2 ITR, a CAG Promoter, a Codon Optimized Human CHM cDNA of SEQ ID NO:1, an SV40 Polyadenylation Signal, and a 3' AAV2 ITR and has the nucleotide sequence of SEQ ID NO:5.

A functional assay was developed to assess the ability of delivered REP1 protein to prenylate Rab27a GTPase (FIG. 4). CHM RPE cells were transduced with rAAV comprising (i) a transgene expression cassette having the sequence of SEQ ID NO:5 and (ii) a modified AAV2 capsid protein having the amino acid sequence of SEQ ID NO:9. Cell lysates from transduced or control CHM1 and CHM2 RPE cells were collected 14 days post infection. Wild type RPE cells were used as a positive control. Prenylation of Rab27a GTPase will only occur in the presence of REP1 and, the prenyl donor, RabGGTase. To visualize the prenyl transfer from RabGGTase to Rab27a GTPase, the prenyl groups were labeled with biotin. The cell lysates, following transduction, were combined with Rab27a GTPase, RabGGTase and biotinylated prenyl groups. The in vitro reaction was incubated for 5 hours to optimize prenyl group transfer. Following the reaction, the lysates were subjected to SDS-PAGE and Western blotting analysis. A SA-HRP conjugate revealed the level of prenylation in each reaction (FIGS. 5a-d). RPE cells derived from a normal fibroblast cell-derived iPSC line were used as a positive control in this experiment.

A second functional experiment was done to confirm that prenylation of Rab27a GTPases, following delivery of the rAAV results in proper trafficking of Rab27a to the target membrane. CHM RPE cells were cultivated at low density ($2.5 \times 10^4$ cells/cm$^2$) and then transduced with rAAV comprising (i) a transgene expression cassette having the sequence of SEQ ID NO:5 and (ii) a modified AAV2 capsid protein having the amino acid sequence of SEQ ID NO:9 at a MOI of 5000 vg/cell. After 14 days, cultures were immunostained with anti-REP1 and anti-RAB27A antibodies and imaged to visualize the subcellular localization of RAB27A in transduced versus untreated cultures. Treatment of CHM RPE cells (FIG. 6a) with the rAAV caused trafficking of RAB27A from the cytoplasmic regions to target membranes (FIG. 6b) analogous to normal FB-iPSC-derived RPE cells (FIG. 6c). These data demonstrate that two weeks after delivery of codon optimized REP1 of SEQ ID NO:1, RAB27A trafficking from the cytoplasmic regions to target membranes was normalized and this correction was associated with restitution of the normal cellular RPE phenotype.

Conclusion

The studies described above demonstrate that codon optimized REP1 of SEQ ID NO:1 is expressed at significantly higher levels in disease-relevant (REP1 deficient) human RPE cells compared to the native (unmodified) REP1 gene. The studies also demonstrate that REP1 expressed from codon optimized REP1 of SEQ ID NO:1 is functional, rescues the prenylation defect (Rab27) and corrects the intracellular trafficking defect in RAb proteins, thus restoring the normal cellular RPE phenotype in the diseased RPE cells. In vitro pharmacology indicates that cohREP1 shows superior correction of REP1 protein deficiency in Retinal Pigment Epithelial (RPE) cells derived from choroideremia patients when compared with the normal gene.

Example 3—Assessment of Safety and Biodistribution of Codon Optimized REP1 cDNA Sequence Delivered by R100 Via Intravitreal Administration in Non-Human Primates Materials and Methods GLP Toxicology and Biodistribution Studies Male cynomolgus macaques (*Macaca fascicularis*) aged 2-14 years were dosed via two 50 µL intravitreal injections into each eye through the sclera for a total dose volume of 100 µL/eye. Doses of 1×10$^{11}$ vg/eye (unilateral administration), 3×10$^{11}$ vg/eye (bilateral administration only), and 1×10$^{12}$ vg/eye (unilateral & bilateral administration) were evaluated. The animals were anesthetized with Ketamine IM and given topical ophthalmic solutions to eliminate pain. 20-80 mg of methylprednisolone was administered by IM injection weekly post-injection. Euthanasia was performed by trained veterinary staff at Week 3, Week 13, and Week 26 post-administration.

4D-110 (rAAV comprising a capsid protein of SEQ ID NO:9 and a heterologous nucleic acid comprising the nucleotide sequence of SEQ ID NO:5) genome biodistribution was assessed in all major ocular compartments (retina, optic nerve, ciliary body, iris, trabecular meshwork), and major systemic organs (including the testes) using validated, GLP-compliant qPCR assay. In tissues where genomes were detected, transgene expression was assessed by a qualified, GLP-compliant RT-qPCR assay.

Serial toxicology assessments performed in the study were: clinical ocular evaluations (complete ophthalmic examinations, including SD-OCT imaging and ERG), systemic evaluations, clinical pathology, gross pathology and microscopic pathology. Assays were validated to determine the anti-capsid and anti-transgene antibody responses. ELISpot assays were validated to detect cellular responses to the R100 capsid (comprising a variant capsid protein of SEQ ID NO:9) and expressed proteins.

Neutralizing Antibody Assay

2v6.11 cells were plated at a density of 3×10$^4$ cells/well 24 hours prior to infection. rAAV vectors encoding firefly luciferase driven by the CAG promoter were incubated at 37° C. for 1 hour with individual serum samples prior to infection, and cells were then infected at a genomic MOI of 1,000. Luciferase activity was assessed 48 hours post infection using the Luc-Screen Extended-Glow Luciferase Reporter Gene Assay System (Invitrogen) or the ONE-Glo Luciferase Assay System (Promega) and quantified using the BioTek Cytation 3 Cell Imaging Multi-Mode Reader and Gen5 software.

Prior to enrollment in studies, non-human primates (NHP) serum was screened for the presence of neutralizing antibodies against R100. NHPs were enrolled in studies when samples resulted in less than 50% neutralization of AAV transduction at a 1:10 serum dilution.

AAV Manufacturing

Recombinant R100 viral vectors were produced by transient transfection in HEK293 cells. Cells were cultured in DMEM supplemented with FBS and were maintained at 37° C. in a 5% CO$_2$ environment. Cells were triply transfected (payload, capsid, and helper plasmids) using polyethylenimine (PEI). 48-96 hours post-transfection, viral particles were harvested from cells and/or supernatant and cells lysed via microfluidization. Cell lysate and/or supernatant was enzymatically treated to degrade plasmid and host-cell DNA, then clarified and concentrated by tangential flow filtration (TFF). The TFF retentate was then loaded onto an affinity resin column for purification. Following pH-gradient elution, post-affinity material was buffer exchanged, then further purified (if needed) by anion-exchange chromatography. Purified rAAV was then formulated into DPBS with 0.001% polysorbate-20, sterile filtered, and filled to yield rAAV Drug Product.

Results 4D-110 Delivery is Safe and Results in Expression of Therapeutic Transgene in NHP 4D-110 (R100.CAG-cohRep1) has been advanced into a Phase 1-2 clinical trial. Investigational New Drug (IND)-enabling data for this product includes evaluation in two separate 6-month Good Laboratory Practices (GLP) toxicology and biodistribution studies (Table 4). A total of 61 eyes of 44 NHPs were injected by intravitreal injection with either a single eye administration, sequential bilateral administration, or simultaneous bilateral administration.

TABLE 4

Good Laboratory Practices (GLP) Toxicology and Biodistribution Studies

| 4DMT Study Number | Lot Number | Number | Gender | Eye(s) | Dose | In-Life |
|---|---|---|---|---|---|---|
| 4D17-02 | N/A | 1 | Male | OD | vehicle | 3 weeks |
| | 4DEP000003.01 | 4 | Male | OD | 1E+11 vg/eye | |
| | 4DEP000004.01 | 5 | Male | OD | 1E+12 vg/eye | |
| | N/A | 1 | Male | OD | vehicle | 13 weeks |
| | 4DEP000003.01 | 4 | Male | OD | 1E+11 vg/eye | |
| | 4DEP000004.01 | 5 | Male | OD | 1E+12 vg/eye | |
| | N/A | 1 | Male | OD | vehicle | 26 weeks |
| | 4DEP000003.01 | 4 | Male | OD | 1E+11 vg/eye | |
| | 4DE1000004.01 | 5 | Male | OD | 1E+12 vg/eye | |
| 4D18-13 | N/A | 3 | Male | OU | vehicle | 26 weeks |
| | | 3 | Male | OU | 1E+11 vg/eye | |
| | | 3 | Male | OD + OS | 1E+11 vg/eye | |
| | 4DEP000011.01 | 4 | Male | OU | 1E+12 vg/eye | |
| | | 4 | Male | OD + OS | 1E+12 vg/eye | |
| | | 3 | Male | OU | 1E+12 vg/eye | 13 weeks |

Figure 9:
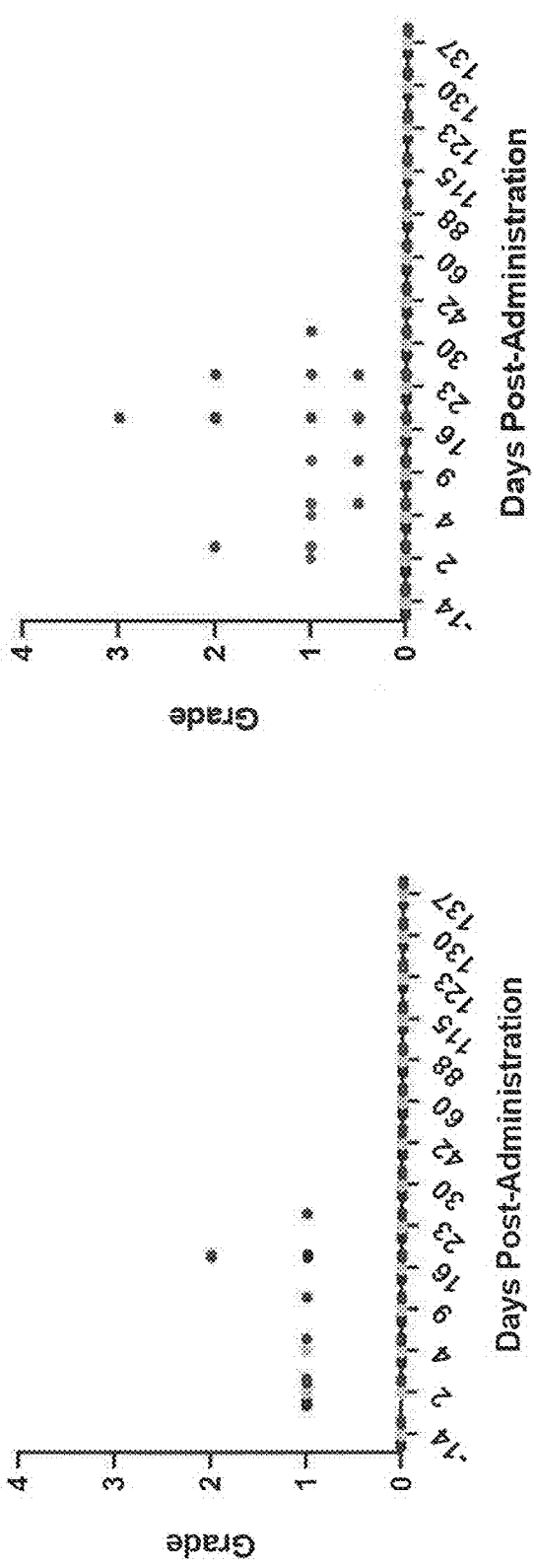
FIG. 9 illustrates safety of 4D-110 (comprising the transgene cassette shown in FIG. 8 and a capsid protein of SEQ ID NO:9) following intravitreal administration to non-human primates through quantification of ocular inflammation, as assessed by aqueous flare, aqueous cells, and vitreous cells. Ophthalmoscopic signs of transient mild ocular inflammation were observed at the high dose. These changes responded to an increase in the systemic steroid treatment. There were no adverse findings considered related to 4D-110. IOP values were within normal limits for all animals at the different examination intervals. ERG values and OCT images including macular morphology were also within normal limits.
Figure 9:
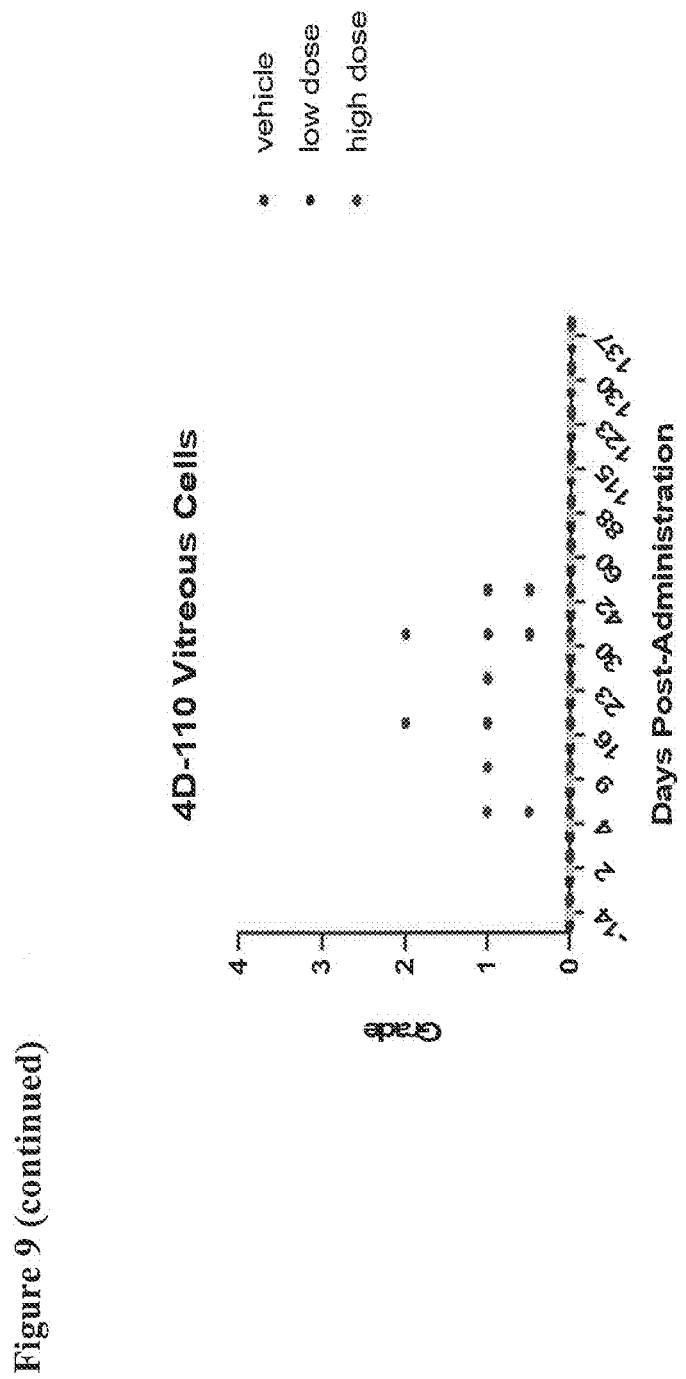

No significant toxicities were observed with 4D-110 at either dose level, as determined by clinical observations, histopathology, OCT, or ERG. Administration of 4D-110 into a single eye resulted in only minimal to mild anterior uveitis that was restricted to the immediate post-administration period and resolved by Week 3 (FIG. 9); in some cases systemic steroid doses were transiently increased. Bilateral administration of 4D-110 resulted in transient minimal to moderate anterior uveitis in both low and high dose groups; this finding resolved within two weeks generally, coincident with an increase in systemic steroid treatment.

Figure 10:
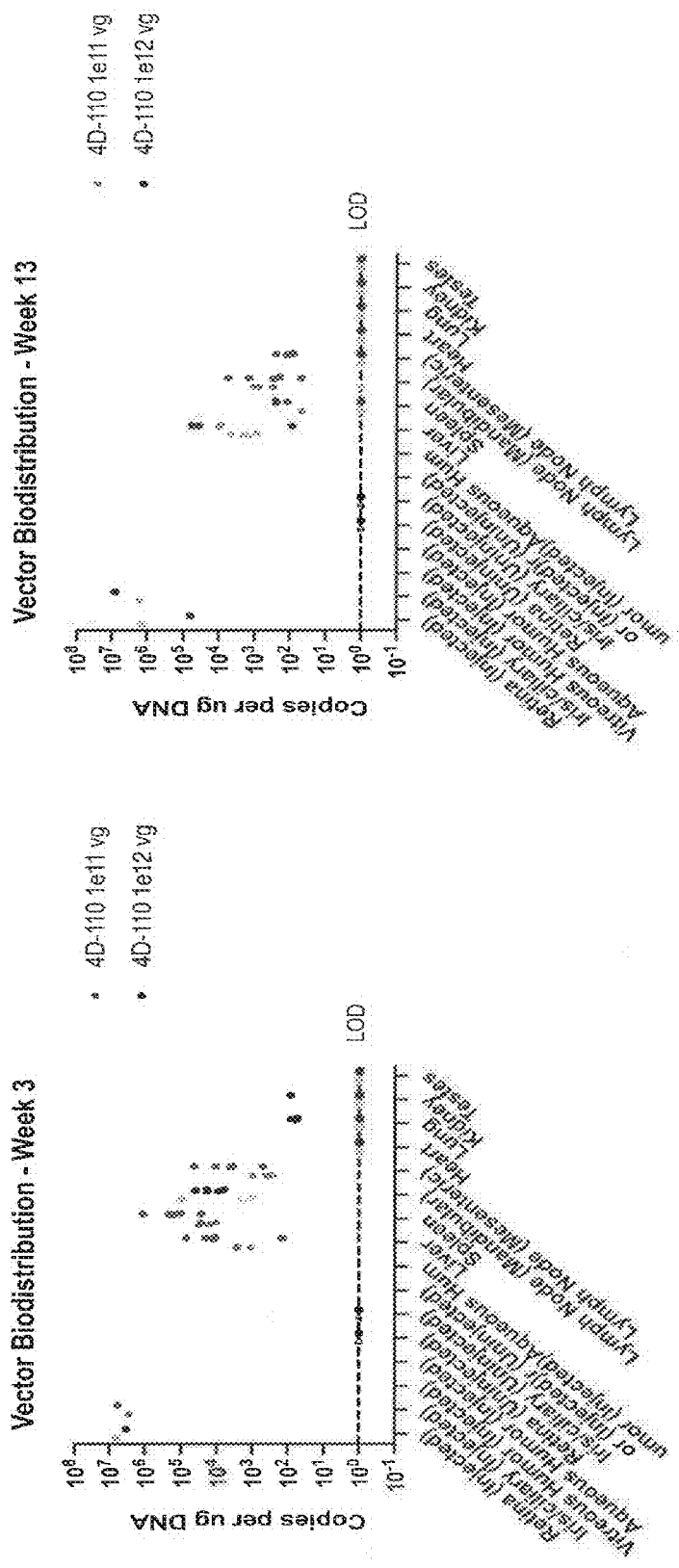
FIG. 10 illustrates vector genome biodistribution in selected retinal, ocular, and non-ocular tissues, as measured by qPCR at 3 necropsy timepoints in NHPs intravitreally administered 4D-110. LOD=lower limit of detection; all samples "BLOD" graphed at LOD value for visualization purposes.
Figure 10:
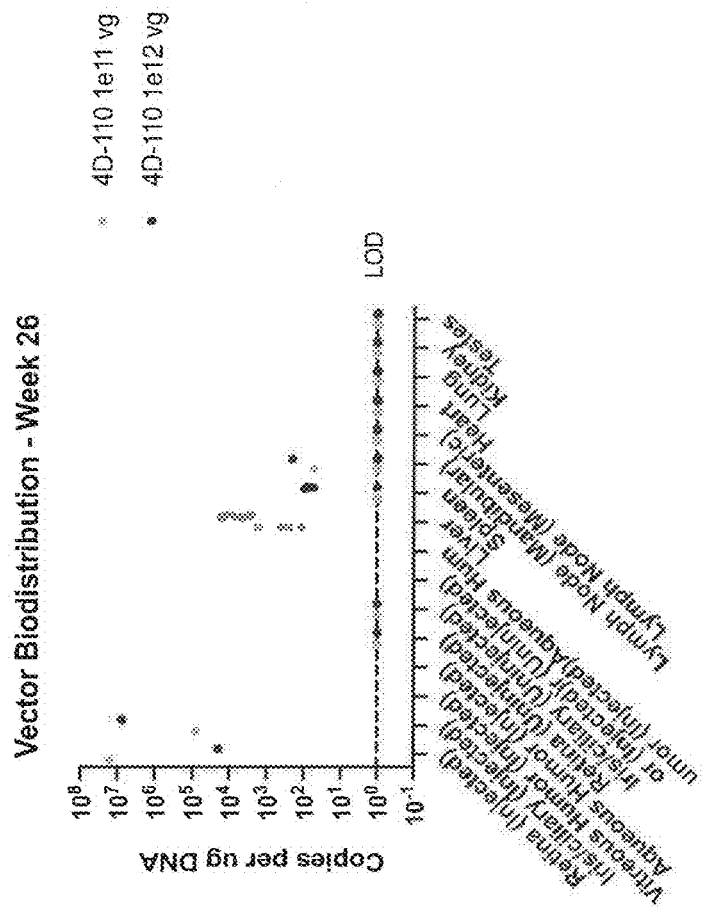
Figure 11:
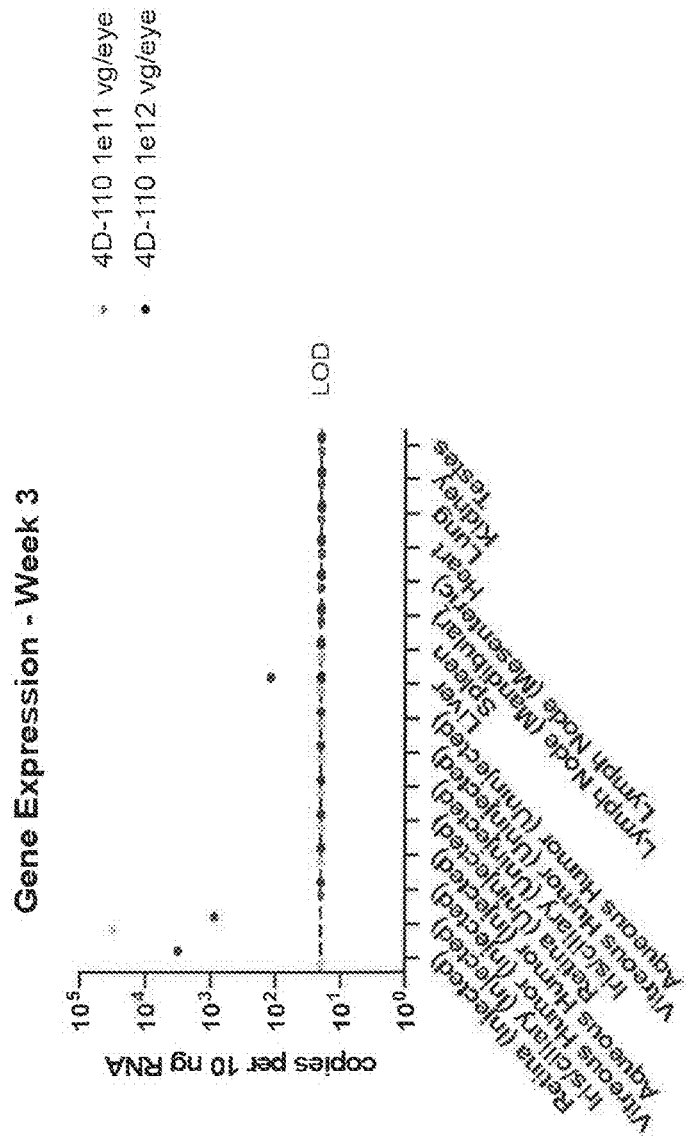
FIG. 11 illustrates REP1 transgene mRNA expression in selected retinal, ocular, and non-ocular tissues, as measured by RT-qPCR at 3 necropsy timepoints in NHPs intravitreally administered 4D-110. LOD=lower limit of detection; all samples "BLOD" graphed at LOD value for visualization purposes.
Figure 11:
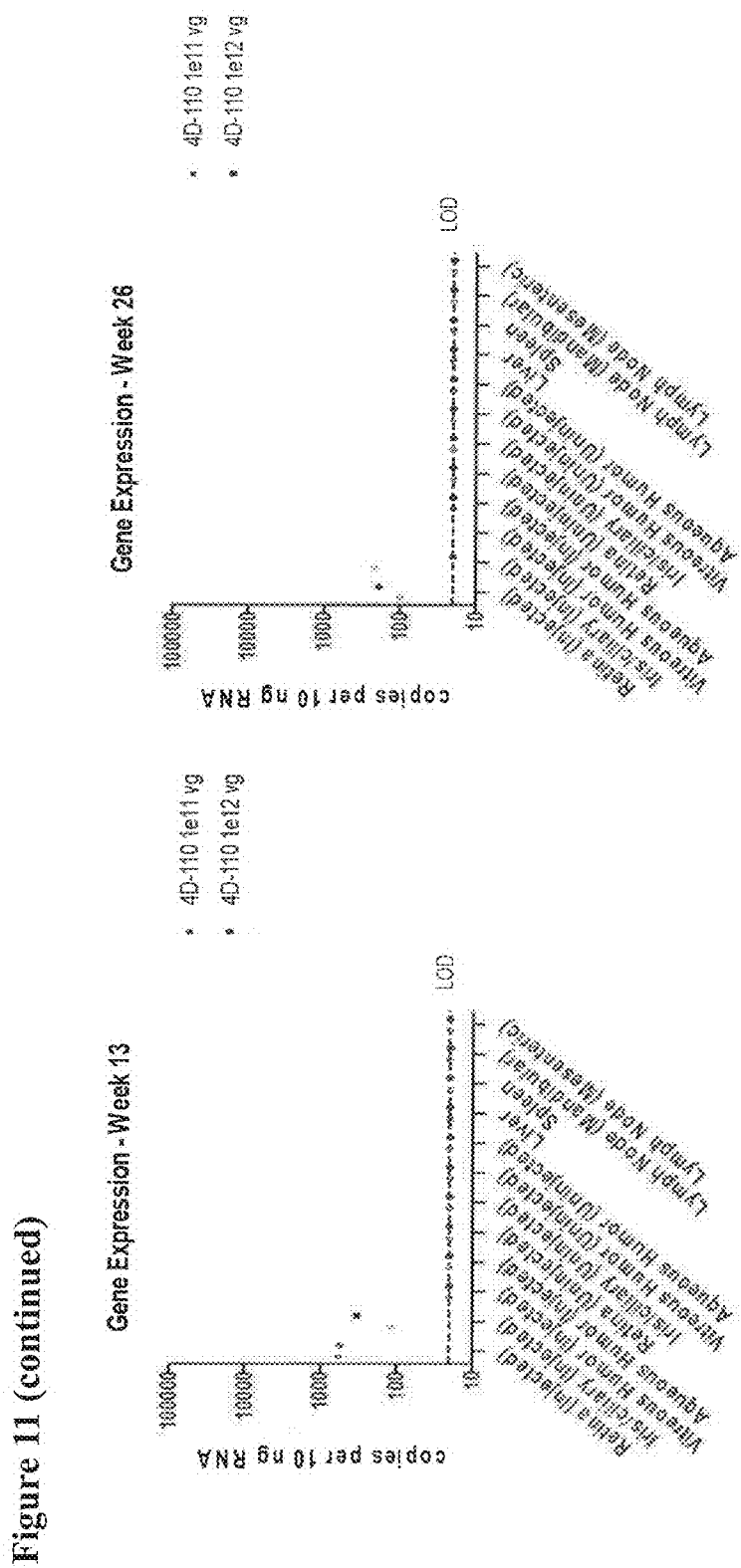

Very high levels of vector genomes were present in the retina of the treated eye at all timepoints (week 3, left panel; week 13, middle panel; week 26, right panel) indicating persistence of the vector in ocular tissue (FIG. 10). In addition to the retina, vector genomes were detected in the treated eye within samples from the aqueous humor, vitreous humor, iris/ciliary body, and the optic nerve at all timepoints. Non-ocular tissues generally had no detectable vector genomes with the exception of low levels in liver, spleen, and the lymph nodes (FIG. 10). R100 vector-derived transgene expression was detected in the treated retina and iris/ciliary body from both low and high dose groups (FIG. 11). Gene expression was dose-dependent and increased from Week 3 to Week 13 and remained stable at Week 26 (FIG. 11, left, middle and right panel respectively). No non-ocular vector expression was detected at Week 26 in any study (FIG. 11).

Using an ELISpot assay to evaluate cellular immune responses, no animals developed significant responses to R100 capsid peptides or transgene peptides (data not shown). A majority of animals dosed with 4D-110 generated an anti-capsid antibody response post-administration (data not shown).

Summary 4D-110 (R100.CAG-cohRep1) has recently been translated into a clinical trial for the inherited retinal disease choroideremia (NCT04483440). This therapeutic product has been evaluated in two separate GLP toxicology and biodistribution studies (Table 4). A total of 44 NHPs were injected with a single eye administration, sequential bilateral administration, or simultaneous bilateral administration; a total of 61 NHP eyes were injected. No significant test-article-related adverse events or T-cell responses were reported. Mild to moderate, transient corticosteroid-responsive anterior uveitis was observed. Transgene expression was localized to the retina, and expression was not detected in any of the systemic organs evaluated. Human clinical trials are underway in order to determine the safety, pharmacodynamics, and efficacy (including through serial visual field testing and optical coherence tomography scans) of this product by intravitreal injection.

Example 4—Assessment of Safety of Codon Optimized REP1 eDNA Sequence Delivered by R100 Via Intravitreal Administration in Human Choroideremia Patients Initial Phase 1 Dose Escalation Safety and Tolerability Data Summary Clinical Trial Designs and Enrollment The clinical trial employed a standard "3+3" dose-escalation designed to assess the safety, tolerability and biologic activity of a single intravitreal injection of 4D-110 at two dose levels (3E11 or 1E12 vg/eye). A total of six patients were enrolled across dose escalation cohorts, with three at each dose level. Patients received a standard immunosuppression regimen with taper; adjustments were determined by investigators. The results described are based on data cut-offs between 1-9 months post-administration.

Initial Tolerability and Adverse Event Profile 4D-110 was well-tolerated throughout the assessment period as outlined in the treatment-emergent adverse event (AE) summary table (Table 5):

TABLE 5

| Adverse Event Summary | |
|---|---|
| Patient # enrolled | 6 |
| Doses | 3E11 or 1E12 vg/eye |
| Follow-up data cut-off (months) | 1-9 months |
| Dose-Limiting Toxicities (DLTs) | 0 (0%) |
| Serious AE | 0 (0%) |
| Any CTCAE Grade ≥ 3 | 0 (0%) |
| Retinal AE (Any Grade) | 0 (0%) |
| Uveitis CTCAE Grade 2 (moderate) | 1/6 (17%) |
| Uveitis CTCAE Grade 1 (mild) | 4/6 (67%) |

Clinical Assessments

Patients' ocular and systemic status is closely monitored including detailed ophthalmic evaluations and retinal imaging together with blood testing and systemic examinations, as necessary. A variety of visual function and anatomical assessments is performed to detect any preliminary efficacy signal. These assessments include, but are not limited to, measurements of ellipsoid zone (EZ) area, fundus autofluorescence, microperimetry, static automated perimetry, and best corrected visual acuity (BCVA).

While the materials and methods of this invention have been described in terms of preferred embodiments, it will be apparent to those of skill in the art that variations may be applied to the method described herein without departing from the concept, spirit and scope of the invention. All such similar substitutes and modifications apparent to those skilled in the art are deemed to be within the spirit, scope and concept of the invention.

The invention claimed is:

1. A nucleic acid encoding human Rab escort protein-1 (REP1) protein of SEQ ID NO:2 and codon optimized for expression in humans, the nucleic acid comprising the nucleotide sequence set forth as SEQ ID NO: 1 or comprising a nucleotide sequence at least 90% identical thereto.

2. The nucleic acid according to claim 1, wherein the nucleotide sequence has a codon adaptation index of at least 0.94.

3. An expression cassette comprising the nucleic acid according to claim 1, wherein said nucleotide sequence is operably linked to an expression control sequence.

4. The expression cassette of claim 3, wherein the expression control sequence comprises a constitutive promoter or comprises a promoter that directs cell-specific expression of the nucleic acid in rod and cone cells.

5. The expression cassette of claim 4, wherein the expression control sequence comprises a CAG promoter.

6. The expression cassette of claim 4, comprising from 5' to 3': (a) a 5' AAV2 terminal repeat (b) a CAG promoter (c) a nucleotide sequence at least 90% identical to the nucleotide sequence set forth in SEQ ID NO:1 (d) an SV40 polyadenylation sequence and (e) a 3' AAV2 terminal repeat.

7. The expression cassette of claim 6, wherein the 5' AAV2 terminal repeat has the nucleotide sequence set forth as SEQ ID NO:6 and/or wherein the CAG promoter has the nucleotide sequence set forth as SEQ ID NO:4 and/or wherein the SV40 polyadenylation sequence has the nucleotide sequence set forth as SEQ ID NO:8 and/or wherein the 3' AAV2 terminal repeat has the nucleotide sequence set forth as SEQ ID NO:7.

8. A recombinant adeno-associated virus (rAAV) vector comprising a heterologous nucleic acid comprising the expression cassette according to claim 3.

9. The rAAV vector of claim 8, wherein the rAAV vector comprises an AAV capsid of serotype 2, 4, 5 or 8 or a variant thereof.

10. The rAAV vector of claim 9, wherein the rAAV vector comprises a variant AAV capsid protein comprising the amino acid sequence of SEQ ID NO:9.

11. The rAAV vector of claim 10, wherein the rAAV vector comprises a nucleic acid comprising from 5' to 3': (a) a 5' AAV2 terminal repeat (b) a CAG promoter (c) a nucleotide sequence at least 90% identical to the nucleotide sequence set forth in SEQ ID NO:1 (d) an SV40 polyadenylation sequence and (e) a 3' AAV2 terminal repeat.

12. The rAAV vector of claim 11, wherein the 5' AAV2 terminal repeat has the nucleotide sequence set forth as SEQ ID NO:6 and/or wherein the CAG promoter has the nucleotide sequence set forth as SEQ ID NO:4 and/or wherein the SV40 polyadenylation sequence has the nucleotide sequence set forth as SEQ ID NO:8 and/or wherein the 3' AAV2 terminal repeat has the nucleotide sequence set forth as SEQ ID NO:7.

13. A method for treating choroideremia in a human subject in need thereof, comprising administering to the subject a therapeutically effective amount of pharmaceutical composition comprising an rAAV vector according to claim 8 and a pharmaceutically acceptable excipient, whereby the choroideremia is treated in the human subject.

14. The method according to claim 13, wherein the rAAV vector comprises a nucleic acid comprising from 5' to 3': (a) a 5' AAV2 terminal repeat (b) a CAG promoter (c) a nucleotide sequence at least 90% identical to the nucleotide sequence set forth in SEQ ID NO:1 (d) an SV40 polyadenylation sequence and (e) a 3' AAV2 terminal repeat.

15. The method according to claim 14, wherein the 5' AAV2 terminal repeat has the nucleotide sequence set forth as SEQ ID NO:6 and/or wherein the CAG promoter has the nucleotide sequence set forth as SEQ ID NO:4 and/or wherein the SV40 polyadenylation sequence has the nucleotide sequence set forth as SEQ ID NO:8 and/or wherein the 3' AAV2 terminal repeat has the nucleotide sequence set forth as SEQ ID NO:7.

16. The method according to claim 13, wherein the rAAV vector comprises an AAV capsid of serotype 2, 4, 5 or 8 or a variant thereof.

17. The method according to claim 16, wherein the rAAV vector comprises a variant AAV capsid protein comprising the amino acid sequence of SEQ ID NO:9.

18. The method according to claim 13, wherein the pharmaceutical composition is administered to the subject by periocular, intravitreal, suprachoroidal or subretinal injection.

19. The method according to claim 18, wherein the vector is administered to the subject at a dosage from about $10^{10}$ vector genomes (vg)/eye to about $10^{13}$ vg/eye.

20. A pharmaceutical composition comprising the rAAV vector according to claim 8 and at least one pharmaceutically acceptable excipient.

* * * * *

SEQUENCE LISTING

```
<160> NUMBER OF SEQ ID NOS: 9

<210> SEQ ID NO 1
<211> LENGTH: 1962
<212> TYPE: DNA
<213> ORGANISM: Artificial Sequence
<220> FEATURE:
<223> OTHER INFORMATION: codon optimized human REP1

<400> SEQUENCE: 1
atggctgata cactgccttc tgagtttgat gtgatcgtga ttggaactgg actgcctgag      60
agtattattg ctgctgcttg tagtagaagc ggccggagag tgctgcacgt ggacagcaga     120
```

```
tcctactatg cggcaactg ggcctctttc agcttttccg gcctgctgag ctggctgaag    180
gagtaccagg agaactccga catcgtgtct gatagcccg tgtggcagga ccagatcctg    240
gagaatgagg aggccatcgc cctgtccagg aaggataaga ccatccagca cgtggaggtg    300
ttctgctatg ccagccagga cctgcacgag gatgtggagg aggcaggcgc cctgcagaag    360
aaccacgccc tggtgacctc cgccaattct acagaggccg ccgactccgc ctttctgcct    420
accgaggatg agtccctgtc tacaatgtct tgtgagatgc tgaccgagca gacacctagc    480
tccgatccag agaacgccct ggaggtcaat ggcgccgagg tgaccggcga aggagaaac    540
cactgcgaca taagacctg cgtgccaagc acatccgccg aggacatgtc cgagaacgtg    600
cctatcgccg aggataccac agagcagcca agaagaatc gcatcacata cagccagatc    660
atcaaggagg gcaggcgctt caatatcgac ctggtgtcta agctgctgta cagccgggc    720
ctgctgatcg atctgctgat caagagcaac gtgtcccgct atgccgagtt caagaatatc    780
accagaatcc tggcctttcg ggagggaaga gtggagcagg tgccctgcag cagagccgac    840
gtgttcaact ccaagcagct gacaatggtg gagaagagga tgctgatgaa gttcctgaca    900
ttttgtatgg agtacgagaa gtatccagat gagtacaagg ctatgaggga gatcaccttt    960
tacgagtatc tgaagaccca gaagctgaca cccaatctgc agtacatcgt gatgcactcc   1020
atcgccatga cctctgagac agcctctagc accatcgacg gcctgaaggc cacaaagaac   1080
ttcctgcact gcctgggccg gtacggcaat acacccttcc tgtttcctct gtatggccag   1140
ggcgagctgc cccagtgctt ctgtagaatg tgcgccgtgt ttggcggcat ctattgcctg   1200
aggcactctg tgcagtgtct ggtggtggac aaggagagcc gcaagtgtaa ggccatcatc   1260
gatcagtttg ccagcggat catctctgag cacttcctgg tggaggacag ctactttcct   1320
gagaacatgt gctccagggt gcagtatcgc cagatcagcc gggccgtgct gatcaccgat   1380
agatccgtgc tgaagacaga cagcgatcag cagatcagca tcctgaccgt gccagcagag   1440
gagccaggca ccttcgccgt gagagtgatc gagctgtgct cctctaccat gacatgtatg   1500
aagggcaccct acctggtgca cctgacctgc acaagctcca agacagcccg cgaggacctg   1560
gagagcgtgg tgcagaagct gttcgtgccc tacaccgaga tggagatcga aacgagcag   1620
gtggagaagc ctagaatcct gtgggccctg tacttcaaca tgagagactc tagcgatatc   1680
tctaggagct gttacaacga tctgccctct aacgtgtacg tgtgcagcgg acctgactgt   1740
ggcctgggaa acgataatgc cgtgaagcag gccgagacac tgttccagga gatttgccct   1800
aacgaggact tttgtccccc tccacccaat ccagaggata tcatcctgga cggcgattcc   1860
ctgcagccag aggcctctga gtcctctgcc atccccgagg ccaatagcga aacattcaaa   1920
gaaagcacaa atctgggaaa cctggaagaa agtagtgagt aa                      1962
```

<210> SEQ ID NO 2
<211> LENGTH: 653
<212> TYPE: PRT
<213> ORGANISM: Homo sapiens

<400> SEQUENCE: 2

Met Ala Asp Thr Leu Pro Ser Glu Phe Asp Val Ile Val Ile Gly Thr
1               5                   10                  15

Gly Leu Pro Glu Ser Ile Ile Ala Ala Ala Cys Ser Arg Ser Gly Arg
            20                  25                  30

Arg Val Leu His Val Asp Ser Arg Ser Tyr Tyr Gly Gly Asn Trp Ala
        35                  40                  45

```
Ser Phe Ser Phe Ser Gly Leu Leu Ser Trp Leu Lys Glu Tyr Gln Glu
 50                  55                  60
Asn Ser Asp Ile Val Ser Asp Ser Pro Val Trp Gln Asp Gln Ile Leu
 65                  70                  75                  80
Glu Asn Glu Glu Ala Ile Ala Leu Ser Arg Lys Asp Lys Thr Ile Gln
                     85                  90                  95
His Val Glu Val Phe Cys Tyr Ala Ser Gln Asp Leu His Glu Asp Val
                100                 105                 110
Glu Glu Ala Gly Ala Leu Gln Lys Asn His Ala Leu Val Thr Ser Ala
                115                 120                 125
Asn Ser Thr Glu Ala Ala Asp Ser Ala Phe Leu Pro Thr Glu Asp Glu
130                 135                 140
Ser Leu Ser Thr Met Ser Cys Glu Met Leu Thr Glu Gln Thr Pro Ser
145                 150                 155                 160
Ser Asp Pro Glu Asn Ala Leu Glu Val Asn Gly Ala Glu Val Thr Gly
                165                 170                 175
Glu Lys Glu Asn His Cys Asp Asp Lys Thr Cys Val Pro Ser Thr Ser
                180                 185                 190
Ala Glu Asp Met Ser Glu Asn Val Pro Ile Ala Glu Asp Thr Thr Glu
                195                 200                 205
Gln Pro Lys Lys Asn Arg Ile Thr Tyr Ser Gln Ile Ile Lys Glu Gly
210                 215                 220
Arg Arg Phe Asn Ile Asp Leu Val Ser Lys Leu Leu Tyr Ser Arg Gly
225                 230                 235                 240
Leu Leu Ile Asp Leu Leu Ile Lys Ser Asn Val Ser Arg Tyr Ala Glu
                245                 250                 255
Phe Lys Asn Ile Thr Arg Ile Leu Ala Phe Arg Glu Gly Arg Val Glu
                260                 265                 270
Gln Val Pro Cys Ser Arg Ala Asp Val Phe Asn Ser Lys Gln Leu Thr
                275                 280                 285
Met Val Glu Lys Arg Met Leu Met Lys Phe Leu Thr Phe Cys Met Glu
290                 295                 300
Tyr Glu Lys Tyr Pro Asp Glu Tyr Lys Gly Tyr Glu Glu Ile Thr Phe
305                 310                 315                 320
Tyr Glu Tyr Leu Lys Thr Gln Lys Leu Thr Pro Asn Leu Gln Tyr Ile
                325                 330                 335
Val Met His Ser Ile Ala Met Thr Ser Glu Thr Ala Ser Ser Thr Ile
                340                 345                 350
Asp Gly Leu Lys Ala Thr Lys Asn Phe Leu His Cys Leu Gly Arg Tyr
                355                 360                 365
Gly Asn Thr Pro Phe Leu Phe Pro Leu Tyr Gly Gln Gly Glu Leu Pro
370                 375                 380
Gln Cys Phe Cys Arg Met Cys Ala Val Phe Gly Gly Ile Tyr Cys Leu
385                 390                 395                 400
Arg His Ser Val Gln Cys Leu Val Val Asp Lys Glu Ser Arg Lys Cys
                405                 410                 415
Lys Ala Ile Ile Asp Gln Phe Gly Gln Arg Ile Ile Ser Glu His Phe
                420                 425                 430
Leu Val Glu Asp Ser Tyr Phe Pro Glu Asn Met Cys Ser Arg Val Gln
                435                 440                 445
Tyr Arg Gln Ile Ser Arg Ala Val Leu Ile Thr Asp Arg Ser Val Leu
450                 455                 460
```

Lys Thr Asp Ser Asp Gln Gln Ile Ser Ile Leu Thr Val Pro Ala Glu
465                 470                 475                 480

Glu Pro Gly Thr Phe Ala Val Arg Val Ile Glu Leu Cys Ser Ser Thr
            485                 490                 495

Met Thr Cys Met Lys Gly Thr Tyr Leu Val His Leu Thr Cys Thr Ser
        500                 505                 510

Ser Lys Thr Ala Arg Glu Asp Leu Glu Ser Val Val Gln Lys Leu Phe
        515                 520                 525

Val Pro Tyr Thr Glu Met Glu Ile Glu Asn Glu Gln Val Glu Lys Pro
        530                 535                 540

Arg Ile Leu Trp Ala Leu Tyr Phe Asn Met Arg Asp Ser Ser Asp Ile
545                 550                 555                 560

Ser Arg Ser Cys Tyr Asn Asp Leu Pro Ser Asn Val Tyr Val Cys Ser
                565                 570                 575

Gly Pro Asp Cys Gly Leu Gly Asn Asp Asn Ala Val Lys Gln Ala Glu
            580                 585                 590

Thr Leu Phe Gln Glu Ile Cys Pro Asn Glu Asp Phe Cys Pro Pro Pro
        595                 600                 605

Pro Asn Pro Glu Asp Ile Ile Leu Asp Gly Asp Ser Leu Gln Pro Glu
        610                 615                 620

Ala Ser Glu Ser Ser Ala Ile Pro Glu Ala Asn Ser Glu Thr Phe Lys
625                 630                 635                 640

Glu Ser Thr Asn Leu Gly Asn Leu Glu Glu Ser Ser Glu
                645                 650

<210> SEQ ID NO 3
<211> LENGTH: 1962
<212> TYPE: DNA
<213> ORGANISM: Homo sapiens

<400> SEQUENCE: 3
atggcggata ctctcccttc ggagtttgat gtgatcgtaa tagggacggg tttgcctgaa      60
tccatcattg cagctgcatg ttcaagaagt ggccggagag ttctgcatgt tgattcaaga     120
agctactatg gaggaaactg gccagttttt agcttttcag gactattgtc ctggctaaag     180
gaataccagg aaaacagtga cattgtaagt gacagtccag tgtggcaaga ccagatcctt     240
gaaaatgaag aagccattgc tcttagcagg aaggacaaaa ctattcaaca tgtgaagta      300 ttttgttatg ccagtcagga tttgcatgaa gatgtcgaag aagctggtgc actgcagaaa     360
aatcatgctc ttgtgacatc tgcaaactcc acagaagctg cagattctgc cttcctgcct     420
acggaggatg agtcattaag cactatgagc tgtgaaatgc tcacagaaca aactccaagc     480
agcgatccag agaatgcgct agaagtaaat ggtgctgaag tgacagggga aaagaaaaac     540
cattgtgatg ataaaacttg tgtgccatca acttcagcag aagacatgag tgaaaatgtg     600
cctatagcag aagataccac agagcaacca agaaaaaaca gaattactta ctcacaaatt     660 attaagaag gcaggagatt taatattgat ttagtatcaa agctgctgta ttctcgagga     720
ttactaattg atcttctaat caaatctaat gttagtcgat atgcagagtt taaaaatatt     780
accaggattc ttgcatttcg agaaggacga gtggaacagg ttccgtgttc cagagcagat     840
gtctttaata gcaaacaact tactatggta gaaaagcgaa tgctaatgaa atttcttaca     900
ttttgtatgg aatatgagaa atatcctgat gaatataaag gatatgaaga gatcacattt     960
tatgaatatt taaagactca aaattaacc cccaacctcc aatatattgt catgcattca    1020
attgcaatga catcagagac agccagcagc accatagatg gtctcaaagc taccaaaaac    1080

```
tttcttcact gtcttgggcg gtatggcaac actccatttt tgtttcctt atatggccaa    1140 ggagaactcc cccagtgttt ctgcaggatg tgtgctgtgt tggtggaat ttattgtctt    1200 cgccattcag tacagtgcct tgtagtggaa aagaatcca gaaatgtaa agcaattata    1260 gatcagtttg gtcagagaat aatctctgag catttcctcg tggaggacag ttactttcct    1320
gagaacatgt gctcacgtgt gcaatacagg cagatctcca gggcagtgct gattacagat    1380
agatctgtcc taaaaacaga ttcagatcaa cagatttcca ttttgacagt gccagcagag    1440
gaaccaggaa cttttgctgt tcgggtcatt gagttatgtt cttcaacgat gacatgcatg    1500
aaaggcacct atttggttca tttgacttgc acatcttcta aaacagcaag agaagattta    1560
gaatcagttg tgcagaaatt gtttgttcca tatactgaaa tggagataga aatgaacaa    1620 gtagaaaagc caagaattct gtgggctctt tacttcaata tgagagattc gtcagacatc    1680
agcaggagct gttataatga tttaccatcc aacgtttatg tctgctctgg cccagattgt    1740
ggtttaggaa atgataatgc agtcaaacag gctgaaacac ttttccagga aatctgcccc    1800
aatgaagatt tctgtccccc tccaccaaat cctgaagaca ttatccttga tggagacagt    1860
ttacagccag aggcttcaga atccagtgcc ataccagagg ctaactcgga gactttcaag    1920
gaaagcacaa accttggaaa cctagaggag tcctctgaat aa                       1962
```

<210> SEQ ID NO 4
<211> LENGTH: 1664
<212> TYPE: DNA
<213> ORGANISM: Artificial Sequence
<220> FEATURE:
<223> OTHER INFORMATION: CAG promoter

<400> SEQUENCE: 4

```
actagttatt aatagtaatc aattacgggg tcattagttc atagcccata tatggagttc     60
cgcgttacat aacttacggt aaatggcccg cctggctgac cgcccaacga ccccgccca    120 ttgacgtcaa taatgacgta tgttcccata gtaacgccaa tagggacttt ccattgacgt    180
caatgggtgg agtatttacg gtaaactgcc cacttggcag tacatcaagt gtatcatatg    240
ccaagtacgc cccctattga cgtcaatgac ggtaaatggc ccgcctggca ttatgcccag    300
tacatgacct tatgggactt tcctacttgg cagtacatct acgtattagt catcgctatt    360
accatggtcg aggtgagccc cacgttctgc ttcactctcc ccatctcccc ccctccccca    420
cccccaattt tgtatttatt tattttttaa ttattttgtg cagcgatggg ggcggggggg    480 ggggggggc gcgcgccagg cggggcgggg cgggggcgagg ggcggggcgg ggcgaggcgg    540
agaggtgcgg cggcagccaa tcagagcggc gcgctccgaa agtttccttt tatggcgagg    600 cggcggcgg ggcggcccta taaaagcga agcgcgcggc gggcggggag tcgctgcgac    660
gctgccttcg ccccgtgccc cgctccgccg ccgcctcgcg ccgcccgccc cggctctgac    720
tgaccgcgtt actcccacag gtgagcgggc gggacggccc ttctcctccg ggctgtaatt    780
agcgcttggt ttaatgacgg cttgtttctt ttctgtggct gcgtgaaagc cttgaggggc    840
tccgggaggg ccctttgtgc ggggggagcg ggctcggggg tgcgtgcgtg tgtgtgtgcg    900
tggggagcgc gcgcgtgcggc tccgcgctgc ccggcggctg tgagcgctgc gggcgcggcg    960 cggggcttg tgcgctccgc agtgtgcgcg aggggagcgc ggccgggggc ggtgccccgc    1020
ggtgcggggg gggctgcgag gggaacaaag gctgcgtgcg gggtgtgtgc gtgggggggt    1080 gagcagggg tgtgggcgcg tcggtcgggc tgcaacccccc cctgcacccc cctccccgag    1140
```

```
ttgctgagca cggcccggct tcgggtgcgg ggctccgtac ggggcgtggc gcggggctcg    1200
ccgtgccggg cggggggtgg cggcaggtgg gggtgccggg cggggcgggg ccgcctcggg    1260
ccggggaggg ctcgggggag gggcgcggcg gcccccggag cgccggcggc tgtcgaggcg    1320
cggcgagccg cagccattgc cttttatggt aatcgtgcga gagggcgcag ggacttcctt    1380
tgtcccaaat ctgtgcggag ccgaaatctg ggaggcgccg ccgcaccccc tctagcgggc    1440
gcggggcgaa gcggtgcggc gccggcagga aggaaatggg cggggagggc cttcgtgcgt    1500
cgccgcgccg ccgtccccTT ctccctctcc agcctcgggg ctgtccgcgg gggacggct    1560 gccttcgggg gggacgggc agggcggggt tcggcttctg gcgtgtgacc ggcggctcta    1620
gagcctctgc taaccatgtt catgccttct tcttttTcct acag    1664

<210> SEQ ID NO 5
<211> LENGTH: 4271
<212> TYPE: DNA
<213> ORGANISM: Artificial Sequence
<220> FEATURE:
<223> OTHER INFORMATION: REP1 transgene cassette

<400> SEQUENCE: 5
ttggccactc cctctctgcg cgctcgctcg ctcactgagg ccgggcgacc aaaggtcgcc      60
cgacgcccgg gctttgcccg gcggcctca gtgagcgagc gagcgcgcag agagggagtg     120
gccaactcca tcactagggg ttcctatcga ttgaattccc cggggatcca ctagttatta    180
atagtaatca attacgggt cattagttca tagcccatat atggagttcc gcgttacata     240
acttacggta aatggcccgc ctggctgacc gcccaacgac ccccgcccat tgacgtcaat    300
aatgacgtat gttcccatag taacgccaat agggactttc cattgacgtc aatgggtgga    360
gtatttacgg taaactgccc acttggcagt acatcaagtg tatcatatgc caagtacgcc    420
ccctattgac gtcaatgacg gtaaatggcc cgcctggcat tatgcccagt acatgacctt    480
atgggacttt cctacttggc agtacatcta cgtattagtc atcgctatta ccatggtcga    540
ggtgagcccc acgttctgct tcactctccc catctccccc cctccccac ccccaatttt    600 gtatttattt attttttaat tattttgtgc agcgatgggg gcggggggg ggggggggcg    660 cgcgccaggc ggggcggggc ggggcgaggg gcgggggcggg gcgaggcgga gaggtgcggc    720
ggcagccaat cagagcggcg cgctccgaaa gtttcctttt atggcgaggc ggcggcggcg    780
gcggccctat aaaaagcgaa gcgcgcggcg ggcggggagt cgctgcgacg ctgccttcgc    840
cccgtgcccc gctccgccgc cgcctcgcgc cgcccgcccc ggctctgact gaccgcgtta    900
ctcccacagg tgagcgggcg ggacggcccT tctcctccgg gctgtaatta gcgcttggtt    960
taatgacggc ttgtttcttt tctgtggctg cgtgaaagcc ttgaggggct ccgggagggc    1020
cctttgtgcg gggggagcgg ctcggggggt gcgtgcgtgt gtgtgtgcgt ggggagcgcc    1080
gcgtgcggct ccgcgctgcc cggcggctgt gagcgctgcg ggcgcggcgc ggggctttgt    1140
gcgctccgca gtgtgcgcga ggggagcgcg gccggggggcg tgcccccgcg gtgcgggggg    1200
ggctgcgagg ggaacaaagg ctgcgtgcgg ggtgtgtgcg tggggggtg agcaggggt     1260 gtgggcgcgt cggtcgggct gcaacccccc ctgcacccc ctccccgagt tgctgagcac    1320
ggcccggctt cgggtgcggg gctccgtacg ggggcgtggc cggggctcgc cgtgccgggc    1380 gggggggtggc ggcaggtggg ggtgccgggc ggggcgggc cgcctcgggc cggggagggc    1440 tcggggggagg ggcgcggcgg cccccggagc gccggcggct gtcgaggcgc ggcgagccgc    1500
agccattgcc ttttatggta atcgtgcgag agggcgcagg gacttccttt gtcccaaatc    1560
```

-continued

| | |
|---|---|
| tgtgcggagc cgaaatctgg gaggcgccgc cgcacccct ctagcgggcg cggggcgaag | 1620 |
| cggtgcggcg ccggcaggaa ggaaatgggc ggggagggcc ttcgtgcgtc gccgcgccgc | 1680 |
| cgtcccttc tccctctcca gcctcggggc tgtccgcggg gggacggctg ccttcggggg | 1740 |
| ggacggggca gggcggggtt cggcttctgg cgtgtgaccg gcggctctag agcctctgct | 1800 |
| aaccatgttc atgccttctt cttttccta cagtctagag tcgacctgca gaagcttcca | 1860 |
| ccatggctga tacactgcct tctgagtttg atgtgatcgt gattgaact ggactgcctg | 1920 |
| agagtattat tgctgctgct tgtagtagaa gcggccggag agtgctgcac gtggacagca | 1980 |
| gatcctacta tggcggcaac tgggcctctt tcagcttttc cggcctgctg agctggctga | 2040 |
| aggagtacca ggagaactcc gacatcgtgt ctgatagccc cgtgtggcag accagatcc | 2100 |
| tggagaatga ggaggccatc gccctgtcca ggaaggataa gaccatccag cacgtggagg | 2160 |
| tgttctgcta tgccagccag gacctgcacg aggatgtgga ggaggcaggc gccctgcaga | 2220 |
| agaaccacgc cctggtgacc tccgccaatt ctacagaggc cgccgactcc gcctttctgc | 2280 |
| ctaccgagga tgagtccctg tctacaatgt cttgtgagat gctgaccgag cagacaccta | 2340 |
| gctccgatcc agagaacgcc ctggaggtca tggcgccga ggtgaccggc gagaaggaga | 2400 |
| accactgcga cgataagacc tgcgtgccaa gcacatccgc cgaggacatg tccgagaacg | 2460 |
| tgcctatcgc cgaggatacc acagagcagc caaagaagaa tcgcatcaca tacagccaga | 2520 |
| tcatcaagga gggcaggcgc ttcaatatcg acctggtgtc taagctgctg tacagccggg | 2580 |
| gcctgctgat cgatctgctg atcaagagca acgtgtcccg ctatgccgag ttcaagaata | 2640 |
| tcaccagaat cctggccttt cgggagggaa gagtggagca ggtgccctgc agcagagccg | 2700 |
| acgtgttcaa ctccaagcag ctgacaatgg tggagaagag gatgctgatg aagttcctga | 2760 |
| cattttgtat ggagtacgag aagtatccag atgagtacaa gggctatgag gagatcacct | 2820 |
| tttacgagta tctgaagacc cagaagctga cacccaatct gcagtacatc gtgatgcact | 2880 |
| ccatcgccat gacctctgag acagcctcta gcaccatcga cggcctgaag gccacaaaga | 2940 |
| acttcctgca ctgcctgggc cggtacggca atacacccett cctgttcct ctgtatggcc | 3000 |
| agggcgagct gcccagtgc ttctgtagaa tgtgcgccgt gtttggcggc atctattgcc | 3060 |
| tgaggcactc tgtgcagtgt ctggtggtgg acaaggagag ccgcaagtgt aaggccatca | 3120 |
| tcgatcagtt tggccagcgg atcatctctg agcacttcct ggtggaggac agctactttc | 3180 |
| ctgagaacat gtgctccagg gtgcagtatc gccagatcag ccgggccgtg ctgatcaccg | 3240 |
| atagatccgt gctgaagaca gacagcgatc agcagatcag catcctgacc gtgccagcag | 3300 |
| aggagccagg caccttcgcc gtgagagtga tcgagctgtg ctcctctacc atgacatgta | 3360 |
| tgaagggcac ctacctggtg cacctgacct gcacaagctc caagacagcc cgcgaggacc | 3420 |
| tggagagcgt ggtgcagaag ctgttcgtgc cctacaccga tggagatc gagaacgagc | 3480 |
| aggtggagaa gctagaatc ctgtgggccc tgtacttcaa catgagagac tctagcgata | 3540 |
| tctctaggag ctgttacaac gatctgccct ctaacgtgta cgtgtgcagc ggacctgact | 3600 |
| gtggcctggg aaacgataat gccgtgaagc aggccgagac actgttccag gagatttgcc | 3660 |
| ctaacgagga ctttttgtccc cctccaccca atccagagga tatcatcctg gacggcgatt | 3720 |
| ccctgcagcc agaggcctct gagtcctctg ccatcccga ggccaatagc gaaacattca | 3780 |
| aagaaagcac aaatctggga aacctggaag aaagtagtga gtaagcctcg agcagcgctg | 3840 |
| ctcgagagat ctgcggccgc gagctcgggg atccagacat gataagatac attgatgagt | 3900 |

```
ttggacaaac cacaactaga atgcagtgaa aaaaatgctt tatttgtgaa atttgtgatg    3960
ctattgcttt atttgtaacc attataagct gcaataaaca agttaacaac aacaattgca    4020
ttcattttat gtttcaggtt caggggagg tgtgggaggt ttttaaagc aagtaaaacc     4080 tctacaaatg tggtatggct gattatgatc aatgcatcct agccggagga accctagtg    4140 atggagttgg ccactccctc tctgcgcgct cgctcgctca ctgaggccgc ccgggcaaag    4200
cccgggcgtc gggcgacctt tggtcgcccg gcctcagtga gcgagcgagc gcgcagagag    4260
ggagtggcca a                                                         4271

<210> SEQ ID NO 6
<211> LENGTH: 145
<212> TYPE: DNA
<213> ORGANISM: Artificial Sequence
<220> FEATURE:
<223> OTHER INFORMATION: 5' ITR

<400> SEQUENCE: 6
ttggccactc cctctctgcg cgctcgctcg ctcactgagg ccgggcgacc aaaggtcgcc      60
cgacgcccgg gctttgcccg gcggcctca gtgagcgagc gagcgcgcag agagggagtg     120
gccaactcca tcactagggg ttcct                                           145

<210> SEQ ID NO 7
<211> LENGTH: 151
<212> TYPE: DNA
<213> ORGANISM: Artificial Sequence
<220> FEATURE:
<223> OTHER INFORMATION: 3' ITR

<400> SEQUENCE: 7
agccggagga accctagtg atggagttgg ccactccctc tctgcgcgct cgctcgctca      60
ctgaggccgc ccgggcaaag cccgggcgtc gggcgacctt tggtcgcccg gcctcagtga    120
gcgagcgagc gcgcagagag ggagtggcca a                                   151

<210> SEQ ID NO 8
<211> LENGTH: 260
<212> TYPE: DNA
<213> ORGANISM: Artificial Sequence
<220> FEATURE:
<223> OTHER INFORMATION: Polyadenylation signal

<400> SEQUENCE: 8
gagctcgggg atccagacat gataagatac attgatgagt ttggacaaac cacaactaga     60
atgcagtgaa aaaaatgctt tatttgtgaa atttgtgatg ctattgcttt atttgtaacc    120
attataagct gcaataaaca agttaacaac aacaattgca ttcattttat gtttcaggtt    180 caggggagg tgtgggaggt ttttaaagc aagtaaaacc tctacaaatg tggtatggct      240
gattatgatc aatgcatcct                                                260

<210> SEQ ID NO 9
<211> LENGTH: 745
<212> TYPE: PRT
<213> ORGANISM: Artificial Sequence
<220> FEATURE:
<223> OTHER INFORMATION: variant AAV capsid protein

<400> SEQUENCE: 9

Met Ala Ala Asp Gly Tyr Leu Pro Asp Trp Leu Glu Asp Thr Leu Ser
1               5                   10                  15
```

-continued

```
Glu Gly Ile Arg Gln Trp Trp Lys Leu Lys Pro Gly Pro Pro Pro
            20                  25                  30
Lys Ala Ala Glu Arg His Lys Asp Asp Ser Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Glu Ala Asp Ala Ala Leu Glu His Asp Lys Ala Tyr Asp
65                  70                  75                  80
Arg Gln Leu Asp Ser Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Pro Val Lys Thr Ala Pro Gly Lys Lys Arg
    130                 135                 140
Pro Val Glu His Ser Pro Val Glu Pro Asp Ser Ser Gly Thr Gly
145                 150                 155                 160
Lys Ala Gly Gln Gln Pro Ala Arg Lys Arg Leu Asn Phe Gly Gln Thr
                165                 170                 175
Gly Asp Ala Asp Ser Val Pro Asp Pro Gln Pro Leu Gly Gln Pro Pro
            180                 185                 190
Ala Ala Pro Ser Gly Leu Gly Thr Asn Thr Met Ala Thr Gly Ser Gly
        195                 200                 205
Ala Pro Met Ala Asp Asn Asn Glu Gly Ala Asp Gly Val Gly Asn Ser
    210                 215                 220
Ser Gly Asn Trp His Cys Asp Ser Thr Trp Met Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
            260                 265                 270
Phe Gly Tyr Ser Thr Pro Trp Gly Tyr Phe Asp Phe Asn Arg Phe His
        275                 280                 285
Cys His Phe Ser Pro Arg Asp Trp Gln Arg Leu Ile Asn Asn Asn Trp
    290                 295                 300
Gly Phe Arg Pro Lys Arg Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
        355                 360                 365
Val Phe Met Val Pro Gln Tyr Gly Tyr Leu Thr Leu Asn Asn Gly Ser
    370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Ser Arg Thr
```

```
                    435                 440                 445
Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Leu Ala Ile Ser Asp
            580                 585                 590

Gln Thr Lys His Ala Arg Gln Ala Thr Ala Asp Val Asn Thr Gln
        595                 600                 605

Gly Val Leu Pro Gly Met Val Trp Gln Asp Arg Asp Val Tyr Leu Gln
    610                 615                 620

Gly Pro Ile Trp Ala Lys Ile Pro His Thr Asp Gly His Phe His Pro
625                 630                 635                 640

Ser Pro Leu Met Gly Gly Phe Gly Leu Lys His Pro Pro Pro Gln Ile
                645                 650                 655

Leu Ile Lys Asn Thr Pro Val Pro Ala Asn Pro Ser Thr Thr Phe Ser
            660                 665                 670

Ala Ala Lys Phe Ala Ser Phe Ile Thr Gln Tyr Ser Thr Gly Gln Val
        675                 680                 685

Ser Val Glu Ile Glu Trp Glu Leu Gln Lys Glu Asn Ser Lys Arg Trp
    690                 695                 700

Asn Pro Glu Ile Gln Tyr Thr Ser Asn Tyr Asn Lys Ser Val Asn Val
705                 710                 715                 720

Asp Phe Thr Val Asp Thr Asn Gly Val Tyr Ser Glu Pro Arg Pro Ile
                725                 730                 735

Gly Thr Arg Tyr Leu Thr Arg Asn Leu
            740                 745
```